US009683022B2

(12) United States Patent
Carfi et al.

(10) Patent No.: US 9,683,022 B2
(45) Date of Patent: Jun. 20, 2017

(54) COMPLEXES OF CYTOMEGALOVIRUS PROTEINS

(71) Applicant: GlaxoSmithKline Biologicals SA, Rixensart (BE)

(72) Inventors: Andrea Carfi, Cambridge, MA (US); Yingxia Wen, Acton, MA (US)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 14/410,461

(22) PCT Filed: Jun. 29, 2013

(86) PCT No.: PCT/EP2013/063750
§ 371 (c)(1),
(2) Date: Dec. 22, 2014

(87) PCT Pub. No.: WO2014/005959
PCT Pub. Date: Jan. 9, 2014

(65) Prior Publication Data
US 2016/0159864 A1    Jun. 9, 2016

Related U.S. Application Data

(60) Provisional application No. 61/668,975, filed on Jul. 6, 2012, provisional application No. 61/770,257, filed on Feb. 27, 2013.

(51) Int. Cl.
*C07K 14/005* (2006.01)
*A61K 39/12* (2006.01)
*A61K 39/245* (2006.01)
*C12N 7/00* (2006.01)
*A61K 39/00* (2006.01)

(52) U.S. Cl.
CPC ............ *C07K 14/005* (2013.01); *A61K 39/12* (2013.01); *A61K 39/245* (2013.01); *C12N 7/00* (2013.01); *A61K 2039/53* (2013.01); *A61K 2039/545* (2013.01); *A61K 2039/55555* (2013.01); *A61K 2039/55566* (2013.01); *A61K 2039/55588* (2013.01); *A61K 2039/572* (2013.01); *C12N 2710/16122* (2013.01); *C12N 2710/16134* (2013.01); *C12N 2710/16151* (2013.01)

(58) Field of Classification Search
CPC ............ C12N 7/00; C12N 2710/16134; C12N 15/86; C12N 2710/16111; C12N 15/869; A61K 39/12; A61K 39/245; A61K 2039/53; A61K 39/39; A61K 2300/00; A61K 39/42; A61K 2039/6075; C07K 14/005; C07K 16/088; C07K 14/045; C07K 16/085
See application file for complete search history.

(56) References Cited

U.S. PATENT DOCUMENTS

| | | | |
|---|---|---|---|
| 5,608,143 A | 3/1997 | Hershey et al. | 800/205 |
| 5,659,122 A | 8/1997 | Austin | 800/205 |
| 5,693,506 A | 12/1997 | Rodriguez et al. | 435/172.3 |
| 5,767,250 A | 6/1998 | Spaete | |
| 7,704,510 B2* | 4/2010 | Shenk | A61K 39/245 424/192.1 |
| 8,173,362 B2 | 5/2012 | Shenk et al. | 435/5 |
| 8,828,399 B2 | 9/2014 | Shenk et al. | 424/159.1 |
| 2009/0081230 A1* | 3/2009 | Lanzavecchia | C07K 5/0815 424/142.1 |
| 2013/0164289 A1* | 6/2013 | McVoy | A61K 39/245 424/134.1 |
| 2013/0171234 A1* | 7/2013 | Fairman | A61K 39/12 424/450 |
| 2014/0242152 A1 | 8/2014 | Geall et al. | 424/450 |
| 2014/0370026 A1 | 12/2014 | Shenk et al. | 424/139.1 |

FOREIGN PATENT DOCUMENTS

| | | |
|---|---|---|
| WO | WO 2007/146024 | 12/2007 |
| WO | WO 2011/027222 A2 | 3/2011 |
| WO | WO 2012/006380 A2 | 1/2012 |
| WO | WO 2012/015211 A2 | 4/2012 |
| WO | WO 2012/051211 A2 | 4/2012 |
| WO | WO 2012034025 A3 * | 5/2012 ........... A61K 39/245 |
| WO | WO 2013/006842 | 1/2013 |
| WO | WO 2016/067239 A1 | 5/2016 |

OTHER PUBLICATIONS

Davison AJ. UL131 [Human herpesvirus 5]. NCBI Reference Sequence: YP_081566.1. Dep. Sep. 16, 2004.*
Davison AJ. UL130 [Human herpesvirus 5]. NCBI Reference Sequence: YP_081565.1. Dep. Sep. 16, 2004.*
Davison AJ. UL128 [Human herpesvirus 5]. NCBI Reference Sequence: AAR31335.1. Dep. Dec. 20, 2003.*
Davison AJ. UL115; gL [Human herpesvirus 5]. NCBI Reference Sequence: YP_081555.1. Dep. Sep. 16, 2004.*
Davison AJ. UL75; gH [Human herpesvirus 5]. NCBI Reference Sequence: YP_081523.1. Dep. Sep. 16, 2004.*
Dolan A, Cunningham C, Hector RD, Hassan-Walker AF, Lee L, Addison C, Dargan DJ, McGeoch DJ, Gatherer D, Emery VC, Griffiths PD, Sinzger C, McSharry BP, Wilkinson GW, Davison AJ. Genetic content of wild-type human cytomegalovirus. J Gen Virol. May 2004;85(Pt 5):1301-12.*
Genini E, Percivalle E, Sarasini A, Revello MG, Baldanti F, Gerna G. Serum antibody response to the gH/gL/pUL128-131 five-protein complex of human cytomegalovirus (HCMV) in primary and reactivated HCMV infections. J Clin Virol. Oct. 2011;52(2):113-8. Epub Aug. 4, 2011.*

(Continued)

*Primary Examiner* — Rachel B Gill

(57) ABSTRACT

An isolated human cytomegalovirus (HCMV) membrane protein complex that comprises gH, gL and at least one more HCMV glycoprotein is provided. In some embodiments the complex consists of gH, gL and gO. In other embodiments the complex consists of gH, gL, pUL128, pUL130 and pUL131A. Processes for expressing and purifying such complexes, and subsequent uses of such complexes in immunogenic compositions and vaccines, are also provided.

54 Claims, 15 Drawing Sheets

(56) References Cited

OTHER PUBLICATIONS

Macagno A, Bernasconi NL, Vanzetta F, Dander E, Sarasini A, Revello MG, Gerna G, Sallusto F, Lanzavecchia A. Isolation of human monoclonal antibodies that potently neutralize human cytomegalovirus infection by targeting different epitopes on the gH/gL/UL128-131A complex. J Virol. Jan. 2010;84(2):1005-13. Epub Nov. 4, 2009.*
Schleiss MR. Cytomegalovirus vaccines and methods of production (WO20009049138): the emerging recognition of the importance of virus neutralization at the epithelial/endothelial interface. Expert Opin Ther Pat. Apr. 2010;20(4):597-602.*
Ryckman, et al. "Characterization of the Human Cytomegalovirus gH/gL/UL128-131 Complex that Mediates Entry into Epithelial and Endothelial Cells" *Journal of Virology*, 82(1): 60-70 (2008).
Wang, et al. "Human Cytomegalovirus UL131 Open Reading Frame is Required for Epithelial Cell Tropism" *Journal of Virology*, 79(16): 10330-10338 (2005).
Akter, et al. "Two Novel Spliced Genes in Human Cytomegalovirus" *Journal of General Virology*, 84: 1117-1122 (2003).
Boehme, et al. "Human Cytomegalovirus Envelope Glycoproteins B and H Are Necessary for TLR2 Activation in Permissive Cells" *Journal of Immunology*, 177(10): 7094-7102 (2006).
Genini, et al. "Serum Antibody Response to the gH/gL/pUL128-131 Five-Protein Complex of Human Cytomegalovirus (HCMV) in Primary and Reactivated HCMV Infections" *Journal of Clinical Virology*, 52: 113-118 (2011).
Huber, et al. "Intracellular Formation and Processing of the Heterotrimeric gH-gL-gO (gCIII) Glycoprotein Envelope Complex of Human Cytomegalovirus" *Journal of Virology*, 73(5): 3886-3892 (1999).
Kinzler, et al. "Expression and Reconstitution of the gH/gL/gO Complex of Human Cytomegalovirus" *Journal of Clinical Virology*, 25: S87-S95 (2002).
Loignon, et al. "Stable High Volumetric Production of Glycosylated Human Recombinant IFNalpha2b in HEK293 Cells" *BMC Biotechnology*, 8: 65 (2008), 16 pages.
Macagno, et al. "Isolation of Human Monoclonal Antibodies That Potently Neutralize Human Cytomegalovirus Infection by Targeting Different Epitopes on the gH/gL/UL128-131A Complex" *Journal of Virology*, 84(2): 1005-1013 (2010).
Melnick, et al. "Human Cytomegalovirus and Mucoepidermoid Carcinoma of Salivary Glands: Cell-specific Localization of Active Viral and Oncogenic Signaling Proteins is Confirmatory of a Causal Relationship" *Experimental and Molecular Pathology*, 92: 118-125 (2012).
Murthy, et al. "Detection of a Single Identical Cytomegalovirus (CMV) Strain in Recently Seroconverted Young Women" *PLoS One*, 6(1): e15949 (2011), 9 pages.
Patrone, et al. "Human Cytomegalovirus UL130 Protein Promotes Endothelial Cell Infection through a Producer Cell Modification of the Virion" *Journal of Virology*, 79: 8361-8373 (2005).
Rasmussen, et al. "The Genes Encoding the gCIII Complex of Human Cytomegalovirus Exist in Highly Diverse Combinations in Clinical Isolates" *Journal of Virology*, 76(21): 10841-10848 (2002).
Rigoutsos, et al. "In Silico Pattern-Based Analysis of the Human Cytomegalovirus Genome" *Journal of Virology*, 77: 4326-4344 (2003).
Ryckman, et al. "Human Cytomegalovirus TR Strain Glycoprotein O Acts as a Chaperone Promoting gH/gL Incorporation into Virions but Is Not Present in Virions" *Journal of Virology*, 84(5): 2597-2609 (2010).
Lilleri, et al. "Fetal Human Cytomegalovirus Transmission Correlates with Delayed Maternal Antibodies to gH/gL/pUL128-130-131 Complex during Primary Infection" *PLos One*, 8(3): e59863 (2013), 13 pages.
Adler, "Immunization to Prevent Congenital Cytomegalovirus Infection" *British Medical Bulletin*, 107: 57-68 (2013).
Saccoccio, et al. "Peptides from Cytomegalovirus UL130 and UL131 Proteins Induce High Titer Antibodies that Block Viral Entry into Mucosal Epithelial Cells" *Vaccine*, 29(15): 2705-2711 (2011).
Pass, et al. "Vaccine Prevention of Maternal Cytomegalovirus Infection" *The New England Journal of Medicine*, 360(12): 1191-1199 (2009).
Griffiths, et al. "Cytomegalovirus Glycoprotein-B Vaccine with MF59 Adjuvant in Transplant Recipients: A Phase 2 Randomised Placebo-Controlled Trial" *Lancet*, 377: 1256-1263 (2011).
Kharfan-Dabaja, et al. "Novel Therapeutic Cytomegalovirus DNA Vaccine in Allogeneic Haemopoietic Stem-Cell Transplantation: A Randomised, Double-Blind, Placebo-Controlled, Phase 2 Trial" *Lancet Infectious Disease*, 12: 290-299 (2012).
Fouts, et al. "Antibodies against the gH/gL/UL128/UL130/UL131 Complex Comprise the Majority of the Anti-Cytomegalovirus (Anti-CMV) Neutralizing Antibody Response in CMV Hyperimmune Globulin" *Journal of Virology*, 86(13): 7444-7447 (2012).
Freed, et al. "Pentameric Complex of Viral Glycoprotein H is the Primary Target for Potent Neutralization by a Human Cytomegalovirus Vaccine" PNAS 110(51): E4997-E5005 (published online Dec. 2, 2013).
The sequence available as NCBI GenInfo Identifier GI:52139248, entitled *Envelope Glycoprotein H [Human herpesvirus 5]*, submitted Sep. 16, 2004, available at https://www.ncbi.nlm.nih.gov/protein/52139248.
The sequence available as NCBI GenInfo Identifier GI:138314, entitled *Envelope Glycoprotein H*, submitted Apr. 24, 1993, available at https://www.ncbi.nlm.nih.gov/protein/138314.
The sequence available as NCBI GenInfo Identifier GI:138313, entitled *Envelope glycoprotein H*, submitted Apr. 24, 1993, available at https://www.ncbi.nlm.nih.gov/protein/138313.
The sequence available as NCBI GenInfo Identifier GI:39842115, now AAR31659.1, entitled *envelope glycoprotein L [Human herpesvirus 5]*, submitted Dec. 21, 2003, available at https://www.ncbi.nlm.nih.gov/protein/39842115.
The sequence available as NCBI GenInfo Identifier GI:239909463, entitled *Envelope glycoprotein L [Human herpesvirus 5]*, submitted Jun. 17, 2009, available at https://www.ncbi.nlm.nih.gov/protein/239909463.
The sequence available as NCBI GenInfo Identifier GI:2506510, entitled *Envelope glycoprotein L*, submitted Apr. 24, 1993, available at https://www.ncbi.nlm.nih.gov/protein/GI:2506510.
The sequence available as NCBI GenInfo Identifier GI:39842082, entitled *Envelope glycoprotein O [Human herpesvirus 5]*, submitted Dec. 21, 2003, available at https://www.ncbi.nlm.nih.gov/protein/39842082.
The sequence available as NCBI GenInfo Identifier GI:136968, entitled *Glycoprotein O*, submitted Apr. 24, 1993, available at https://www.ncbi.nlm.nih.gov/protein/136968.
The sequence available as NCBI GenInfo Identifier GI:239909431, entitled *Envelope glycoprotein O [Human herpesvirus 5]*, submitted Jun. 17, 2009, available at https://www.ncbi.nlm.nih.gov/protein/239909431.
The sequence available as NCBI GenInfo Identifier GI:39842124, now GenBank Accession No. AAR31668.1, entitled *Truncated envelope protein UL128 [Human herpesvirus 5]*, submitted Dec. 21, 2003, available at https://www.ncbi.nlm.nih.gov/protein/AAR31668.1?report=genpept.
The sequence available as NCBI GenInfo Identified GI:39841882, entitled *Envelope protein UL128 [Human herpesvirus 5]*, submitted Dec. 20, 2003, available at https://www.ncbi.nlm.nih.gov/protein/39841882.
The sequence available as NCBI GenInfo Identifier GI:59803078, entitled *Uncharacterized protein UL128*, submitted Apr. 24, 1993, available at https://www.ncbi.nlm.nih.gov/protein/59803078.
The sequence available as NCBI GenInfo Identifier GI:39842125, entitled *Envelope glycoprotein UL130 [Human herpesvirus 5]*, submitted Dec. 21, 2003, available at https://www.ncbi.nlm.nih.gov/protein/39842125.
The sequence available as NCBI GenInfo Identifier GI:239909473, now GenBank Accession No. ACS32420.1, entitled *Truncated*

(56) References Cited

OTHER PUBLICATIONS

*envelope glycoprotein UL130 [Human herpesvirus 5]*, submitted Jun. 17, 2009, available at https://www.ncbi.nlm.nih.gov/protein/ACS32420.1?report=genpept.

The sequence available as NCBI GenInfo Identifier GI:39842126, entitled *Envelope protein UL131A [Human herpesvirus 5]*, submitted Dec. 21, 2003, available at https://www.ncbi.nlm.nih.gov/protein/39842126.

The sequence available as NCBI GenInfo Identifier GI:239909474, entitled *Envelope protein UL131A [Human herpesvirus 5]*, submitted Jun. 17, 2009, available at https://www.ncbi.nlm.nih.gov/protein/239909474.

The sequence available as NCBI GenInfo Identifier GI:219879712, now GenBank Accession No. ACL51187.1, entitled *TPA: truncated envelope protein UL131A [Human herpesvirus 5]*, submitted Jan. 14, 2009, available at https://www.ncbi.nlm.nih.gov/protein/223657721?report=genbank&log$=protalign&blast_rank=1&RID=1PTUBK6A015.

The sequence available as NCBI GenInfo Identifier GI:39842076, entitled *Envelope glycoprotein B [Human herpesvirus 5]*, submitted Dec. 21, 2003, available at https://www.ncbi.nlm.nih.gov/protein/39842076.

The sequence available as NCBI GenInfo Identifier GI:138193, entitled *Envelope glycoprotein B*, submitted Apr. 24, 1993, available at https://www.ncbi.nlm.nih.gov/protein/138193.

The sequence available as NCBI GenInfo Identifier GI:138192, entitled *Envelope glycoprotein B*, submitted Apr. 24, 1993, available at https://www.ncbi.nlm.nih.gov/protein/138192.

International Search Report and Written Opinion of the International Searching Authority for International application No. PCT/EP2013/063750.

Ryckman Brent J. et al., "Characterization of the human cytomegalovirus gH/gL/UL128-131 complex that mediates entry into epithelial and endothelial cells", Journal of Virology, American Society for Microbiology, US, vol. 82, No. 1, 2008, pp. 60-70.

Eric R. Kinzler et al., "Expression and reconstitution of the gH/gL/g0 complex of human cytomegalovirus", Journal of Clinical Virology, vol. 25, No. Supp. 2, 2002, pp. S87-S95.

Chowdary et al., *Crystal Structure of the Conserved Herpesvirus Fusion Regulator Complex gH-gL*, 2010 Nature Structural & Molecular Biology 17(7): 882-888, online methods page, and Supplemental Information (18 total pages).

Cairns et al., *Epitope Mapping of Herpes Simplex Virus Type 2 gH/gL Defines Distinct Antigenic Sites, Including Some Associated with Biological Function*, 2006 Journal of Virology 80(6): 2596-2608.

* cited by examiner

SEQUENCE LISTING

<160> NUMBER OF SEQ ID NOS: 36

<210> SEQ ID NO 1
<211> LENGTH: 742
<212> TYPE: PRT
<213> ORGANISM: Human cytomegalovirus

<400> SEQUENCE: 1

Met Arg Pro Gly Leu Pro Ser Tyr Leu Ile Ile Leu Ala Val Cys Leu
1               5                   10                  15

-continued

```
Phe Ser His Leu Leu Ser Ser Arg Tyr Gly Ala Glu Ala Val Ser Glu
            20                  25                  30
Pro Leu Asp Lys Ala Phe His Leu Leu Asn Thr Tyr Gly Arg Pro
        35                  40                  45
Ile Arg Phe Leu Arg Glu Asn Thr Thr Gln Cys Thr Tyr Asn Ser Ser
50                  55                  60
Leu Arg Asn Ser Thr Val Val Arg Glu Asn Ala Ile Ser Phe Asn Phe
65                  70                  75                  80
Phe Gln Ser Tyr Asn Gln Tyr Val Phe His Met Pro Arg Cys Leu
                85                  90                  95
Phe Ala Gly Pro Leu Ala Glu Gln Phe Leu Asn Gln Val Asp Leu Thr
            100                 105                 110
Glu Thr Leu Glu Arg Tyr Gln Gln Arg Leu Asn Thr Tyr Ala Leu Val
            115                 120                 125
Ser Lys Asp Leu Ala Ser Tyr Arg Ser Phe Ser Gln Gln Leu Lys Ala
        130                 135                 140
Gln Asp Ser Leu Gly Glu Gln Pro Thr Thr Val Pro Pro Ile Asp
145                 150                 155                 160
Leu Ser Ile Pro His Val Trp Met Pro Pro Gln Thr Thr Pro His Gly
                165                 170                 175
Trp Thr Glu Ser His Thr Thr Ser Gly Leu His Arg Pro His Phe Asn
            180                 185                 190
Gln Thr Cys Ile Leu Phe Asp Gly His Asp Leu Leu Phe Ser Thr Val
        195                 200                 205
Thr Pro Cys Leu His Gln Gly Phe Tyr Leu Ile Asp Glu Leu Arg Tyr
210                 215                 220
Val Lys Ile Thr Leu Thr Glu Asp Phe Phe Val Val Thr Val Ser Ile
225                 230                 235                 240
Asp Asp Asp Thr Pro Met Leu Leu Ile Phe Gly His Leu Pro Arg Val
                245                 250                 255
Leu Phe Lys Ala Pro Tyr Gln Arg Asp Asn Phe Ile Leu Arg Gln Thr
            260                 265                 270
Glu Lys His Glu Leu Leu Val Leu Val Lys Lys Asp Gln Leu Asn Arg
        275                 280                 285
His Ser Tyr Leu Lys Asp Pro Asp Phe Leu Asp Ala Ala Leu Asp Phe
290                 295                 300
Asn Tyr Leu Asp Leu Ser Ala Leu Leu Arg Asn Ser Phe His Arg Tyr
305                 310                 315                 320
Ala Val Asp Val Leu Lys Ser Gly Arg Cys Gln Met Leu Asp Arg Arg
                325                 330                 335
Thr Val Glu Met Ala Phe Ala Tyr Ala Leu Ala Leu Phe Ala Ala Ala
            340                 345                 350
Arg Gln Glu Glu Ala Gly Ala Gln Val Ser Val Pro Arg Ala Leu Asp
        355                 360                 365
Arg Gln Ala Ala Leu Leu Gln Ile Gln Glu Phe Met Ile Thr Cys Leu
        370                 375                 380
Ser Gln Thr Pro Pro Arg Thr Thr Leu Leu Leu Tyr Pro Thr Ala Val
385                 390                 395                 400
Asp Leu Ala Lys Arg Ala Leu Trp Thr Pro Asn Gln Ile Thr Asp Ile
                405                 410                 415
Thr Ser Leu Val Arg Leu Val Tyr Ile Leu Ser Lys Gln Asn Gln Gln
            420                 425                 430
His Leu Ile Pro Gln Trp Ala Leu Arg Gln Ile Ala Asp Phe Ala Leu
```

```
            435                 440                 445
Lys Leu His Lys Thr His Leu Ala Ser Phe Leu Ser Ala Phe Ala Arg
450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
                500                 505                 510

Glu Tyr Leu Ser Asp Leu Tyr Thr Pro Cys Ser Ser Gly Arg Arg
                515                 520                 525

Asp His Ser Leu Glu Arg Leu Thr Arg Leu Phe Pro Asp Ala Thr Val
530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
                580                 585                 590

Asn Gln Tyr Leu Ile Lys Gly Ile Ser Tyr Pro Val Ser Thr Thr Val
                595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Ser
                675                 680                 685

Ser Pro Arg Thr His Tyr Leu Met Leu Leu Lys Asn Gly Thr Val Leu
                690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740

<210> SEQ ID NO 2
<211> LENGTH: 742
<212> TYPE: PRT
<213> ORGANISM: Human cytomegalovirus

<400> SEQUENCE: 2

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
        50                  55                  60
```

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
            85                  90                  95

Phe Ala Gly Pro Leu Ala Glu Gln Phe Leu Asn Gln Val Asp Leu Thr
                100                 105                 110

Glu Thr Leu Glu Arg Tyr Gln Gln Arg Leu Asn Thr Tyr Ala Leu Val
            115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
                180                 185                 190

Gln Thr Cys Ile Leu Phe Asp Gly His Asp Leu Leu Phe Ser Thr Val
            195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
                260                 265                 270

Glu Lys His Glu Leu Leu Val Leu Val Lys Lys Asp Gln Leu Asn Arg
            275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
                340                 345                 350

Arg Gln Glu Glu Ala Gly Ala Gln Val Ser Val Pro Arg Ala Leu Asp
            355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
                420                 425                 430

His Leu Ile Pro Gln Trp Ala Leu Arg Gln Ile Ala Asp Phe Ala Leu
            435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser

```
                    485                 490                 495
Leu Ala Glu Leu Ser His Phe Thr Gln Leu Ala His Pro His His
                500                 505                 510

Glu Tyr Leu Ser Asp Leu Tyr Thr Pro Cys Ser Ser Gly Arg Arg
            515                 520                 525

Asp His Ser Leu Glu Arg Leu Thr Arg Leu Phe Pro Asp Ala Thr Val
        530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
                580                 585                 590

Asn Gln Tyr Leu Ile Lys Gly Ile Ser Tyr Pro Val Ser Thr Thr Val
            595                 600                 605

Val Gly Gln Ser Leu Ile Ile Thr Gln Thr Asp Ser Gln Thr Lys Cys
        610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
                660                 665                 670

Asp Asp Val Leu Phe Ala Leu Asp Pro Tyr Asn Glu Val Val Val Ser
            675                 680                 685

Ser Pro Arg Thr His Tyr Leu Met Leu Leu Lys Asn Gly Thr Val Leu
        690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740

<210> SEQ ID NO 3
<211> LENGTH: 743
<212> TYPE: PRT
<213> ORGANISM: Human cytomegalovirus

<400> SEQUENCE: 3

Met Arg Pro Gly Leu Pro Pro Tyr Leu Thr Val Phe Thr Val Tyr Leu
1               5                   10                  15

Leu Ser His Leu Pro Ser Gln Arg Tyr Gly Ala Asp Ala Ala Ser Glu
            20                  25                  30

Ala Leu Asp Pro His Ala Phe His Leu Leu Leu Asn Thr Tyr Gly Arg
        35                  40                  45

Pro Ile Arg Phe Leu Arg Glu Asn Thr Thr Gln Cys Thr Tyr Asn Ser
    50                  55                  60

Ser Leu Arg Asn Ser Thr Val Val Arg Glu Asn Ala Ile Ser Phe Asn
65                  70                  75                  80

Phe Phe Gln Ser Tyr Asn Gln Tyr Tyr Val Phe His Met Pro Arg Cys
                85                  90                  95

Leu Phe Ala Gly Pro Leu Ala Glu Gln Phe Leu Asn Gln Val Asp Leu
            100                 105                 110
```

-continued

```
Thr Glu Thr Leu Glu Arg Tyr Gln Gln Arg Leu Asn Thr Tyr Ala Leu
            115                 120                 125
Val Ser Lys Asp Leu Ala Ser Tyr Arg Ser Phe Ser Gln Gln Leu Lys
        130                 135                 140
Ala Gln Asp Ser Leu Gly Gln Gln Pro Thr Thr Val Pro Pro Pro Ile
145                 150                 155                 160
Asp Leu Ser Ile Pro His Val Trp Met Pro Pro Gln Thr Thr Pro His
                165                 170                 175
Asp Trp Lys Gly Ser His Thr Thr Ser Gly Leu His Arg Pro His Phe
            180                 185                 190
Asn Gln Thr Cys Ile Leu Phe Asp Gly His Asp Leu Leu Phe Ser Thr
        195                 200                 205
Val Thr Pro Cys Leu His Gln Gly Phe Tyr Leu Met Asp Glu Leu Arg
    210                 215                 220
Tyr Val Lys Ile Thr Leu Thr Glu Asp Phe Phe Val Val Thr Val Ser
225                 230                 235                 240
Ile Asp Asp Thr Pro Met Leu Leu Ile Phe Gly His Leu Pro Arg
                245                 250                 255
Val Leu Phe Lys Ala Pro Tyr Gln Arg Asp Asn Phe Ile Leu Arg Gln
            260                 265                 270
Thr Glu Lys His Glu Leu Leu Val Leu Val Lys Lys Ala Gln Leu Asn
        275                 280                 285
Arg His Ser Tyr Leu Lys Asp Ser Asp Phe Leu Asp Ala Ala Leu Asp
    290                 295                 300
Phe Asn Tyr Leu Asp Leu Ser Ala Leu Leu Arg Asn Ser Phe His Arg
305                 310                 315                 320
Tyr Ala Val Asp Val Leu Lys Ser Gly Arg Cys Gln Met Leu Asp Arg
                325                 330                 335
Arg Thr Val Glu Met Ala Phe Ala Tyr Ala Leu Ala Leu Phe Ala Ala
            340                 345                 350
Ala Arg Gln Glu Glu Ala Gly Thr Glu Ile Ser Ile Pro Arg Ala Leu
        355                 360                 365
Asp Arg Gln Ala Ala Leu Leu Gln Ile Gln Glu Phe Met Ile Thr Cys
    370                 375                 380
Leu Ser Gln Thr Pro Pro Arg Thr Thr Leu Leu Leu Tyr Pro Thr Ala
385                 390                 395                 400
Val Asp Leu Ala Lys Arg Ala Leu Trp Thr Pro Asp Gln Ile Thr Asp
                405                 410                 415
Ile Thr Ser Leu Val Arg Leu Val Tyr Ile Leu Ser Lys Gln Asn Gln
            420                 425                 430
Gln His Leu Ile Pro Gln Trp Ala Leu Arg Gln Ile Ala Asp Phe Ala
        435                 440                 445
Leu Gln Leu His Lys Thr His Leu Ala Ser Phe Leu Ser Ala Phe Ala
    450                 455                 460
Arg Gln Glu Leu Tyr Leu Met Gly Ser Leu Val His Ser Met Leu Val
465                 470                 475                 480
His Thr Thr Glu Arg Arg Glu Ile Phe Ile Val Glu Thr Gly Leu Cys
                485                 490                 495
Ser Leu Ala Glu Leu Ser His Phe Thr Gln Leu Leu Ala His Pro His
            500                 505                 510
His Glu Tyr Leu Ser Asp Leu Tyr Thr Pro Cys Ser Ser Ser Gly Arg
        515                 520                 525
Arg Asp His Ser Leu Glu Arg Leu Thr Arg Leu Phe Pro Asp Ala Thr
```

```
                530                 535                 540
Val Pro Ala Thr Val Pro Ala Leu Ser Ile Leu Ser Thr Met Gln
545                 550                 555                 560

Pro Ser Thr Leu Glu Thr Phe Pro Asp Leu Phe Cys Leu Pro Leu Gly
                565                 570                 575

Glu Ser Phe Ser Ala Leu Thr Val Ser Glu His Val Ser Tyr Val Val
                580                 585                 590

Thr Asn Gln Tyr Leu Ile Lys Gly Ile Ser Tyr Pro Val Ser Thr Thr
                595                 600                 605

Val Val Gly Gln Ser Leu Ile Ile Thr Gln Thr Asp Ser Gln Thr Lys
610                 615                 620

Cys Glu Leu Thr Arg Asn Met His Thr Thr His Ser Ile Thr Ala Ala
625                 630                 635                 640

Leu Asn Ile Ser Leu Glu Asn Cys Ala Phe Cys Gln Ser Ala Leu Leu
                645                 650                 655

Glu Tyr Asp Asp Thr Gln Gly Val Ile Asn Ile Met Tyr Met His Asp
                660                 665                 670

Ser Asp Asp Val Leu Phe Ala Leu Asp Pro Tyr Asn Glu Val Val Val
                675                 680                 685

Ser Ser Pro Arg Thr His Tyr Leu Met Leu Leu Lys Asn Gly Thr Val
                690                 695                 700

Leu Glu Val Thr Asp Val Val Asp Ala Thr Asp Ser Arg Leu Leu
705                 710                 715                 720

Met Met Ser Val Tyr Ala Leu Ser Ala Ile Ile Gly Ile Tyr Leu Leu
                725                 730                 735

Tyr Arg Met Leu Lys Thr Cys
                740

<210> SEQ ID NO 4
<211> LENGTH: 715
<212> TYPE: PRT
<213> ORGANISM: Human cytomegalovirus

<400> SEQUENCE: 4

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
        50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160
```

```
Leu Ser Ile Pro His Val Trp Met Pro Pro Gln Thr Thr Pro His Gly
            165                 170                 175

Trp Thr Glu Ser His Thr Thr Ser Gly Leu His Arg Pro His Phe Asn
        180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
        210                 215                 220

Val Lys Ile Thr Leu Thr Glu Asp Phe Phe Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
        290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
        370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
        450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Gly Arg Arg
        515                 520                 525

Asp His Ser Leu Glu Arg Leu Thr Arg Leu Phe Pro Asp Ala Thr Val
        530                 535                 540

Pro Ala Thr Val Pro Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
```

```
                    580                 585                 590
Asn Gln Tyr Leu Ile Lys Gly Ile Ser Tyr Pro Val Ser Thr Thr Val
                595                 600                 605
Val Gly Gln Ser Leu Ile Ile Thr Gln Thr Asp Ser Gln Thr Lys Cys
            610                 615                 620
Glu Leu Thr Arg Asn Met His Thr Thr His Ser Ile Thr Val Ala Leu
625                 630                 635                 640
Asn Ile Ser Leu Glu Asn Cys Ala Phe Cys Gln Ser Ala Leu Leu Glu
                645                 650                 655
Tyr Asp Asp Thr Gln Gly Val Ile Asn Ile Met Tyr Met His Asp Ser
            660                 665                 670
Asp Asp Val Leu Phe Ala Leu Asp Pro Tyr Asn Glu Val Val Val Ser
        675                 680                 685
Ser Pro Arg Thr His Tyr Leu Met Leu Leu Lys Asn Gly Thr Val Leu
        690                 695                 700
Glu Val Thr Asp Val Val Val Asp Ala Thr Asp
705                 710                 715

<210> SEQ ID NO 5
<211> LENGTH: 27
<212> TYPE: PRT
<213> ORGANISM: Artificial Sequence
<220> FEATURE:
<223> OTHER INFORMATION: C-terminal extension including myc-tag and
      his-tag

<400> SEQUENCE: 5

Gly Thr Lys Leu Gly Pro Glu Gln Lys Leu Ile Ser Glu Glu Asp Leu
1               5                  10                  15
Asn Ser Ala Val Asp His His His His His
            20                  25

<210> SEQ ID NO 6
<211> LENGTH: 742
<212> TYPE: PRT
<213> ORGANISM: Human cytomegalovirus

<400> SEQUENCE: 6

Met Arg Pro Gly Leu Pro Ser Tyr Leu Ile Ile Leu Ala Val Cys Leu
1               5                  10                  15
Phe Ser His Leu Leu Ser Ser Arg Tyr Gly Ala Glu Ala Val Ser Glu
                20                  25                  30
Pro Leu Asp Lys Ala Phe His Leu Leu Leu Asn Thr Tyr Gly Arg Pro
            35                  40                  45
Ile Arg Phe Leu Arg Glu Asn Thr Thr Gln Cys Thr Tyr Asn Ser Ser
        50                  55                  60
Leu Arg Asn Ser Thr Val Val Arg Glu Asn Ala Ile Ser Phe Asn Phe
65                  70                  75                  80
Phe Gln Ser Tyr Asn Gln Tyr Tyr Val Phe His Met Pro Arg Cys Leu
                85                  90                  95
Phe Ala Gly Pro Leu Ala Glu Gln Phe Leu Asn Gln Val Asp Leu Thr
            100                 105                 110
Glu Thr Leu Glu Arg Tyr Gln Gln Arg Leu Asn Thr Tyr Ala Leu Val
        115                 120                 125
Ser Lys Asp Leu Ala Ser Tyr Arg Ser Phe Ser Gln Gln Leu Lys Ala
        130                 135                 140
Gln Asp Ser Leu Gly Glu Gln Pro Thr Thr Val Pro Pro Pro Ile Asp
```

```
            145                 150                 155                 160
Leu Ser Ile Pro His Val Trp Met Pro Gln Thr Thr Pro His Gly
                165                 170                 175
Trp Thr Glu Ser His Thr Thr Ser Gly Leu His Arg Pro His Phe Asn
                180                 185                 190
Gln Thr Cys Ile Leu Phe Asp Gly His Asp Leu Leu Phe Ser Thr Val
                195                 200                 205
Thr Pro Cys Leu His Gln Gly Phe Tyr Leu Ile Asp Glu Leu Arg Tyr
    210                 215                 220
Val Lys Ile Thr Leu Thr Glu Asp Phe Phe Val Val Thr Val Ser Ile
225                 230                 235                 240
Asp Asp Asp Thr Pro Met Leu Leu Ile Phe Gly His Leu Pro Arg Val
                245                 250                 255
Leu Phe Lys Ala Pro Tyr Gln Arg Asp Asn Phe Ile Leu Arg Gln Thr
                260                 265                 270
Glu Lys His Glu Leu Leu Val Leu Val Lys Lys Asp Gln Leu Asn Arg
            275                 280                 285
His Ser Tyr Leu Lys Asp Pro Asp Phe Leu Asp Ala Ala Leu Asp Phe
    290                 295                 300
Asn Tyr Leu Asp Leu Ser Ala Leu Leu Arg Asn Ser Phe His Arg Tyr
305                 310                 315                 320
Ala Val Asp Val Leu Lys Ser Gly Arg Cys Gln Met Leu Asp Arg Arg
                325                 330                 335
Thr Val Glu Met Ala Phe Ala Tyr Ala Leu Ala Leu Phe Ala Ala Ala
                340                 345                 350
Arg Gln Glu Glu Ala Gly Ala Gln Val Ser Val Pro Arg Ala Leu Asp
            355                 360                 365
Arg Gln Ala Ala Leu Leu Gln Ile Gln Glu Phe Met Ile Thr Cys Leu
            370                 375                 380
Ser Gln Thr Pro Pro Arg Thr Thr Leu Leu Tyr Pro Thr Ala Val
385                 390                 395                 400
Asp Leu Ala Lys Arg Ala Leu Trp Thr Pro Asn Gln Ile Thr Asp Ile
                405                 410                 415
Thr Ser Leu Val Arg Leu Val Tyr Ile Leu Ser Lys Gln Asn Gln Gln
                420                 425                 430
His Leu Ile Pro Gln Trp Ala Leu Arg Gln Ile Ala Asp Phe Ala Leu
            435                 440                 445
Lys Leu His Lys Thr His Leu Ala Ser Phe Leu Ser Ala Phe Ala Arg
450                 455                 460
Gln Glu Leu Tyr Leu Met Gly Ser Leu Val His Ser Met Leu Val His
465                 470                 475                 480
Thr Thr Glu Arg Arg Glu Ile Phe Ile Val Glu Thr Gly Leu Cys Ser
                485                 490                 495
Leu Ala Glu Leu Ser His Phe Thr Gln Leu Leu Ala His Pro His His
                500                 505                 510
Glu Tyr Leu Ser Asp Leu Tyr Thr Pro Cys Ser Ser Ser Gly Arg Arg
            515                 520                 525
Asp His Ser Leu Glu Arg Leu Thr Arg Leu Phe Pro Asp Ala Thr Val
    530                 535                 540
Pro Ala Thr Val Pro Ala Ala Leu Ser Ile Leu Ser Thr Met Gln Pro
545                 550                 555                 560
Ser Thr Leu Glu Thr Phe Pro Asp Leu Phe Cys Leu Pro Leu Gly Glu
                565                 570                 575
```

-continued

```
Ser Phe Ser Ala Leu Thr Val Ser Glu His Val Ser Tyr Ile Val Thr
                580                 585                 590

Asn Gln Tyr Leu Ile Lys Gly Ile Ser Tyr Pro Val Ser Thr Thr Val
            595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp Gly Thr Lys Leu Gly
705                 710                 715                 720

Pro Glu Gln Lys Leu Ile Ser Glu Glu Asp Leu Asn Ser Ala Val Asp
                725                 730                 735

His His His His His His
            740

<210> SEQ ID NO 7
<211> LENGTH: 278
<212> TYPE: PRT
<213> ORGANISM: Human cytomegalovirus

<400> SEQUENCE: 7

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
```

```
              195                 200                 205
Pro Val Ser Thr Ala Ala Pro Glu Gly Ile Thr Leu Phe Tyr Gly
    210                 215                 220
Leu Tyr Asn Ala Val Lys Glu Phe Cys Leu Arg His Gln Leu Asp Pro
225                 230                 235                 240
Pro Leu Leu Arg His Leu Asp Lys Tyr Tyr Ala Gly Leu Pro Pro Glu
                245                 250                 255
Leu Lys Gln Thr Arg Val Asn Leu Pro Ala His Ser Arg Tyr Gly Pro
                260                 265                 270
Gln Ala Val Asp Ala Arg
        275

<210> SEQ ID NO 8
<211> LENGTH: 278
<212> TYPE: PRT
<213> ORGANISM: Human cytomegalovirus

<400> SEQUENCE: 8

Met Cys Arg Arg Pro Asp Cys Gly Phe Ser Phe Ser Pro Gly Pro Val
1               5                   10                  15
Ala Leu Leu Trp Cys Cys Leu Leu Pro Ile Val Ser Ser Ala Thr
            20                  25                  30
Val Ser Val Ala Pro Thr Val Ala Glu Lys Val Pro Ala Glu Cys Pro
        35                  40                  45
Glu Leu Thr Arg Arg Cys Leu Leu Gly Glu Val Phe Gln Gly Asp Lys
    50                  55                  60
Tyr Glu Ser Trp Leu Arg Pro Leu Val Asn Val Thr Arg Arg Asp Gly
65                  70                  75                  80
Pro Leu Ser Gln Leu Ile Arg Tyr Arg Pro Val Thr Pro Glu Ala Ala
                85                  90                  95
Asn Ser Val Leu Leu Asp Asp Ala Phe Leu Asp Thr Leu Ala Leu Leu
            100                 105                 110
Tyr Asn Asn Pro Asp Gln Leu Arg Ala Leu Leu Thr Leu Leu Ser Ser
        115                 120                 125
Asp Thr Ala Pro Arg Trp Met Thr Val Met Arg Gly Tyr Ser Glu Cys
    130                 135                 140
Gly Asp Gly Ser Pro Ala Val Tyr Thr Cys Val Asp Asp Leu Cys Arg
145                 150                 155                 160
Gly Tyr Asp Leu Thr Arg Leu Ser Tyr Gly Arg Ser Ile Phe Thr Glu
                165                 170                 175
His Val Leu Gly Phe Glu Leu Val Pro Pro Ser Leu Phe Asn Val Val
            180                 185                 190
Val Ala Ile Arg Asn Glu Ala Thr Arg Thr Asn Arg Ala Val Arg Leu
        195                 200                 205
Pro Val Ser Thr Ala Ala Pro Glu Gly Ile Thr Leu Phe Tyr Gly
    210                 215                 220
Leu Tyr Asn Ala Val Lys Glu Phe Cys Leu Arg His Gln Leu Asp Pro
225                 230                 235                 240
Pro Leu Leu Arg His Leu Asp Lys Tyr Tyr Ala Gly Leu Pro Pro Glu
                245                 250                 255
Leu Lys Gln Thr Arg Val Asn Leu Pro Ala His Ser Arg Tyr Gly Pro
                260                 265                 270
Gln Ala Val Asp Ala Arg
        275
```

<210> SEQ ID NO 9
<211> LENGTH: 278
<212> TYPE: PRT
<213> ORGANISM: Human cytomegalovirus

<400> SEQUENCE: 9

Met Cys Arg Arg Pro Asp Cys Gly Phe Ser Phe Ser Pro Gly Pro Val
1               5                   10                  15

Val Leu Leu Trp Cys Cys Leu Leu Pro Ile Val Ser Ser Val Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Gln Gly Asp Lys
    50                  55                  60

Tyr Glu Ser Trp Leu Arg Pro Leu Val Asn Val Thr Arg Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 10
<211> LENGTH: 472
<212> TYPE: PRT
<213> ORGANISM: Human cytomegalovirus

<400> SEQUENCE: 10

Met Gly Lys Lys Glu Met Ile Met Val Lys Gly Ile Pro Lys Ile Met
1               5                   10                  15

Leu Leu Ile Ser Ile Thr Phe Leu Leu Leu Ser Leu Ile Asn Cys Asn
            20                  25                  30

Val Leu Val Asn Ser Arg Gly Thr Arg Arg Ser Trp Pro Tyr Thr Val
        35                  40                  45

```
Leu Ser Tyr Arg Gly Lys Glu Ile Leu Lys Lys Gln Lys Glu Asp Ile
    50              55                  60

Leu Lys Arg Leu Met Ser Thr Ser Ser Asp Gly Tyr Arg Phe Leu Met
 65              70                  75                      80

Tyr Pro Ser Gln Gln Lys Phe His Ala Ile Val Ile Ser Met Asp Lys
                 85                  90                  95

Phe Pro Gln Asp Tyr Ile Leu Ala Gly Pro Ile Arg Asn Asp Ser Ile
            100                 105                 110

Thr His Met Trp Phe Asp Phe Tyr Ser Thr Gln Leu Arg Lys Pro Ala
            115                 120                 125

Lys Tyr Val Tyr Ser Glu Tyr Asn His Thr Ala His Lys Ile Thr Leu
    130                 135                 140

Arg Pro Pro Cys Gly Thr Val Pro Ser Met Asn Cys Leu Ser Glu
145             150                 155                     160

Met Leu Asn Val Ser Lys Arg Asn Asp Thr Gly Glu Lys Gly Cys Gly
                165                 170                 175

Asn Phe Thr Thr Phe Asn Pro Met Phe Phe Asn Val Pro Arg Trp Asn
                180                 185                 190

Thr Lys Leu Tyr Ile Gly Ser Asn Lys Val Asn Val Asp Ser Gln Thr
                195                 200                 205

Ile Tyr Phe Leu Gly Leu Thr Ala Leu Leu Leu Arg Tyr Ala Gln Arg
    210                 215                 220

Asn Cys Thr Arg Ser Phe Tyr Leu Val Asn Ala Met Ser Arg Asn Leu
225             230                 235                     240

Phe Arg Val Pro Lys Tyr Ile Asn Gly Thr Lys Leu Lys Asn Thr Met
                245                 250                 255

Arg Lys Leu Lys Arg Lys Gln Ala Leu Val Lys Glu Gln Pro Gln Lys
                260                 265                 270

Lys Asn Lys Lys Ser Gln Ser Thr Thr Thr Pro Tyr Leu Ser Tyr Thr
    275                 280                 285

Thr Ser Thr Ala Phe Asn Val Thr Thr Asn Val Thr Tyr Ser Ala Thr
    290                 295                 300

Ala Ala Val Thr Arg Val Ala Thr Ser Thr Thr Gly Tyr Arg Pro Asp
305             310                 315                     320

Ser Asn Phe Met Lys Ser Ile Met Ala Thr Gln Leu Arg Asp Leu Ala
                325                 330                 335

Thr Trp Val Tyr Thr Thr Leu Arg Tyr Arg Asn Glu Pro Phe Cys Lys
                340                 345                 350

Pro Asp Arg Asn Arg Thr Ala Val Ser Glu Phe Met Lys Asn Thr His
            355                 360                 365

Val Leu Ile Arg Asn Glu Thr Pro Tyr Thr Ile Tyr Gly Thr Leu Asp
    370                 375                 380

Met Ser Ser Leu Tyr Tyr Asn Glu Thr Met Ser Val Glu Asn Glu Thr
385             390                 395                     400

Ala Ser Asp Asn Asn Glu Thr Thr Pro Thr Ser Pro Ser Thr Arg Phe
                405                 410                 415

Gln Arg Thr Phe Ile Asp Pro Leu Trp Asp Tyr Leu Asp Ser Leu Leu
            420                 425                 430

Phe Leu Asp Lys Ile Arg Asn Phe Ser Leu Gln Leu Pro Ala Tyr Gly
            435                 440                 445

Asn Leu Thr Pro Pro Glu His Arg Arg Ala Ala Asn Leu Ser Thr Leu
    450                 455                 460

Asn Ser Leu Trp Trp Trp Ser Gln
```

465            470

<210> SEQ ID NO 11
<211> LENGTH: 466
<212> TYPE: PRT
<213> ORGANISM: Human cytomegalovirus

<400> SEQUENCE: 11

Met Gly Arg Lys Glu Met Met Val Arg Asp Val Pro Lys Met Val Phe
1               5                   10                  15

Leu Ile Ser Ile Ser Phe Leu Leu Val Ser Phe Ile Asn Cys Lys Val
            20                  25                  30

Met Ser Lys Ala Leu Tyr Asn Arg Pro Trp Arg Gly Leu Val Leu Ser
        35                  40                  45

Lys Ile Gly Lys Tyr Lys Leu Asp Gln Leu Lys Leu Glu Ile Leu Arg
    50                  55                  60

Gln Leu Glu Thr Thr Ile Ser Thr Lys Tyr Asn Val Ser Lys Gln Pro
65                  70                  75                  80

Val Lys Asn Leu Thr Met Asn Met Thr Glu Phe Pro Gln Tyr Tyr Ile
                85                  90                  95

Leu Ala Gly Pro Ile Gln Asn Tyr Ser Ile Thr Tyr Leu Trp Phe Asp
            100                 105                 110

Phe Tyr Ser Thr Gln Leu Arg Lys Pro Ala Lys Tyr Val Tyr Ser Gln
        115                 120                 125

Tyr Asn His Thr Ala Lys Thr Ile Thr Phe Arg Pro Pro Cys Gly
    130                 135                 140

Thr Val Pro Ser Met Thr Cys Leu Ser Glu Met Leu Asn Val Ser Lys
145                 150                 155                 160

Arg Asn Asp Thr Gly Glu Gln Gly Cys Gly Asn Phe Thr Thr Phe Asn
                165                 170                 175

Pro Met Phe Phe Asn Val Pro Arg Trp Asn Thr Lys Leu Tyr Val Gly
            180                 185                 190

Pro Thr Lys Val Asn Val Asp Ser Gln Thr Ile Tyr Phe Leu Gly Leu
        195                 200                 205

Thr Ala Leu Leu Leu Arg Tyr Ala Gln Arg Asn Cys Thr His Ser Phe
    210                 215                 220

Tyr Leu Val Asn Ala Met Ser Arg Asn Leu Phe Arg Val Pro Lys Tyr
225                 230                 235                 240

Ile Asn Gly Thr Lys Leu Lys Asn Thr Met Arg Lys Leu Lys Arg Lys
                245                 250                 255

Gln Ala Pro Val Lys Glu Gln Phe Glu Lys Ala Lys Lys Thr Gln
            260                 265                 270

Ser Thr Thr Thr Pro Tyr Phe Ser Tyr Thr Thr Ser Ala Ala Leu Asn
    275                 280                 285

Val Thr Thr Asn Val Thr Tyr Ser Ile Thr Thr Ala Ala Arg Arg Val
        290                 295                 300

Ser Thr Ser Thr Ile Ala Tyr Arg Pro Asp Ser Ser Phe Met Lys Ser
305                 310                 315                 320

Ile Met Ala Thr Gln Leu Arg Asp Leu Ala Thr Trp Val Tyr Thr Thr
                325                 330                 335

Leu Arg Tyr Arg Gln Asn Pro Phe Cys Glu Pro Ser Arg Asn Arg Thr
            340                 345                 350

Ala Val Ser Glu Phe Met Lys Asn Thr His Val Leu Ile Arg Asn Glu
        355                 360                 365

-continued

Thr Pro Tyr Thr Ile Tyr Gly Thr Leu Asp Met Ser Ser Leu Tyr Tyr
        370                 375                 380

Asn Glu Thr Met Phe Val Glu Asn Lys Thr Ala Ser Asp Ser Asn Lys
385                 390                 395                 400

Thr Thr Pro Thr Ser Pro Ser Met Gly Phe Gln Arg Thr Phe Ile Asp
                405                 410                 415

Pro Leu Trp Asp Tyr Leu Asp Ser Leu Leu Phe Leu Asp Glu Ile Arg
                420                 425                 430

Asn Phe Ser Leu Arg Ser Pro Thr Tyr Val Asn Leu Thr Pro Pro Glu
            435                 440                 445

His Arg Arg Ala Val Asn Leu Ser Thr Leu Asn Ser Leu Trp Trp Trp
450                 455                 460

Leu Gln
465

<210> SEQ ID NO 12
<211> LENGTH: 457
<212> TYPE: PRT
<213> ORGANISM: Human cytomegalovirus

<400> SEQUENCE: 12

Met Gly Arg Lys Gly Glu Met Arg Gly Val Phe Asn Leu Phe Phe Leu
1               5                   10                  15

Met Ser Leu Thr Phe Leu Leu Phe Ser Phe Ile Asn Cys Lys Ile Ala
                20                  25                  30

Val Ala Arg Phe Arg Val Lys Ser Gln Lys Ala Lys Glu Glu Glu Arg
            35                  40                  45

Gln Leu Lys Leu Arg Ile Leu Gln Glu Leu Ala Ser Lys Thr Gly Asp
        50                  55                  60

Tyr Tyr Lys Phe Phe Thr Phe Pro Ser Gln Gln Lys Leu Tyr Asn Ile
65                  70                  75                  80

Thr Val Glu Met Lys Gln Phe Pro Pro Asn Ser Ile Leu Ala Gly Pro
                85                  90                  95

Ile Arg Asn His Ser Ile Thr His Leu Trp Phe Asp Phe His Thr Thr
            100                 105                 110

Gln Leu Arg Lys Pro Ala Lys Tyr Val Tyr Ser Glu Tyr Asn His Thr
        115                 120                 125

Gly Gln Lys Ile Thr Phe Arg Pro Pro Ser Cys Gly Thr Ile Pro Ser
    130                 135                 140

Met Thr Cys Leu Ser Glu Met Leu Asn Val Ser Arg Arg Asn Asn Thr
145                 150                 155                 160

Gly Glu Glu Asn Cys Gly Asn Phe Thr Thr Phe Asn Pro Met Phe Phe
                165                 170                 175

Asn Val Pro Arg Trp Asn Thr Lys Leu Tyr Val Gly Pro Ser Lys Val
            180                 185                 190

Asn Val Asp Ser Gln Thr Ile Tyr Phe Leu Gly Leu Ala Ala Leu Leu
        195                 200                 205

Leu Arg Tyr Ala Gln Arg Asn Cys Thr Arg Ser Phe Tyr Leu Val Asn
    210                 215                 220

Ala Met Ser Arg Asn Ile Phe Arg Val Pro Lys Tyr Ile Asn Ser Thr
225                 230                 235                 240

Lys Leu Lys Asn Thr Met Arg Lys Leu Lys Arg Lys Gln Ala Pro Val
                245                 250                 255

Lys Ser Ile Ser Lys Lys Ser Arg Val Ser Thr Thr Thr Pro Tyr Ser
            260                 265                 270

```
Ser Tyr Thr Ser Thr Ile Phe Asn Val Ser Thr Asn Val Thr Tyr Ser
        275                 280                 285

Pro Ile Val Pro Thr Arg Ile Pro Thr Ser Thr Ile Gly Tyr Arg Pro
    290                 295                 300

Asp Glu Asn Phe Met Lys Ser Ile Leu Thr Thr Gln Leu Lys Asp Leu
305                 310                 315                 320

Ala Thr Trp Val Tyr Thr Thr Leu Arg Tyr Arg Asp Glu Pro Phe Cys
                325                 330                 335

Lys Pro Asn Arg Asn Arg Thr Ala Val Ser Glu Phe Met Lys Asn Thr
                340                 345                 350

His Val Leu Ile Arg Asn Glu Thr Pro Tyr Thr Ile Tyr Gly Thr Leu
                355                 360                 365

Asp Met Ser Ser Leu Tyr Tyr Asn Asp Thr Met Pro Val Glu Asn Glu
370                 375                 380

Thr Ala Ser Asp Asn Asn Lys Thr Thr Pro Thr Ser Pro Ser Thr Arg
385                 390                 395                 400

Phe Gln Arg Thr Phe Ile Asp Pro Met Trp Asp Tyr Leu Asp Ser Leu
                405                 410                 415

Leu Phe Leu Ser Glu Ile Arg Asn Phe Ser Leu Gln Ser Ser Thr Tyr
                420                 425                 430

Gly Asn Leu Thr Pro Pro Glu His Arg Arg Ala Val Asn Leu Ser Thr
                435                 440                 445

Leu Asn Ser Leu Trp Trp Trp Leu Gln
                450                 455

<210> SEQ ID NO 13
<211> LENGTH: 130
<212> TYPE: PRT
<213> ORGANISM: Human cytomegalovirus

<400> SEQUENCE: 13

Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
            35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
                100                 105                 110

Lys Val Asn Asp Lys Ala Gln Tyr Leu Leu Gly Ala Ala Gly Ser Val
            115                 120                 125

Pro Tyr
    130

<210> SEQ ID NO 14
<211> LENGTH: 171
<212> TYPE: PRT
<213> ORGANISM: Human cytomegalovirus, strain Towne

<400> SEQUENCE: 14
```

Met Ser Pro Lys Asn Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 15
<211> LENGTH: 171
<212> TYPE: PRT
<213> ORGANISM: Human cytomegalovirus

<400> SEQUENCE: 15

Met Ser Pro Lys Asp Leu Thr Pro Phe Leu Thr Thr Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 16
<211> LENGTH: 214
<212> TYPE: PRT

<213> ORGANISM: Human cytomegalovirus

<400> SEQUENCE: 16

Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Val Ile Trp
            100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala
        130                 135                 140

Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
            195                 200                 205

His Pro Asn Leu Ile Val
        210

<210> SEQ ID NO 17
<211> LENGTH: 229
<212> TYPE: PRT
<213> ORGANISM: Human cytomegalovirus

<400> SEQUENCE: 17

Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
            20                  25                  30

Ala Asn Gln Asn Pro Ser Pro Pro Trp Ser Lys Leu Thr Tyr Ser Lys
        35                  40                  45

Pro His Asp Ala Ala Thr Phe Tyr Cys Pro Phe Leu Tyr Pro Ser Pro
    50                  55                  60

Pro Arg Ser Pro Leu Gln Phe Ser Gly Phe Gln Arg Val Leu Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
            115                 120                 125

Ala Ser Lys Pro Ser Asp Gly Asn Val Gln Ile Ser Val Glu Asp Ala

```
                 130                 135                 140
Lys Ile Phe Gly Ala His Met Val Pro Lys Gln Thr Lys Leu Leu Arg
145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Phe Thr Pro Ser Ala
            195                 200                 205

Pro Ile Pro Ile Ser Ser Phe Glu Pro Val Ala Arg Ala Gly Asn Phe
210                 215                 220

Glu Asn Arg Ala Ser
225

<210> SEQ ID NO 18
<211> LENGTH: 129
<212> TYPE: PRT
<213> ORGANISM: Human cytomegalovirus

<400> SEQUENCE: 18

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
                20                  25                  30

Val Pro His Tyr Trp Asp Ala Cys Ser Arg Ala Leu Pro Asp Gln Thr
            35                  40                  45

Arg Tyr Lys Tyr Val Glu Gln Leu Val Asp Leu Thr Leu Asn Tyr His
        50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 19
<211> LENGTH: 129
<212> TYPE: PRT
<213> ORGANISM: Human cytomegalovirus

<400> SEQUENCE: 19

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
                20                  25                  30

Val Pro His Tyr Trp Asp Ala Cys Ser Arg Ala Leu Pro Asp Gln Thr
            35                  40                  45

Arg Tyr Lys Tyr Val Glu Gln Leu Val Asp Leu Thr Leu Asn Tyr His
        50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95
```

```
Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
            115                 120                 125

Asn

<210> SEQ ID NO 20
<211> LENGTH: 74
<212> TYPE: PRT
<213> ORGANISM: Human cytomegalovirus

<400> SEQUENCE: 20

Met Arg Leu Cys Arg Val Trp Leu Ser Val Cys Leu Cys Ala Val Val
1               5                   10                  15

Leu Gly Gln Cys Gln Arg Glu Thr Ala Glu Lys Lys Arg Leu Leu Pro
            20                  25                  30

Ser Thr Ala Leu Leu Gly Arg Val Leu Ser Arg Ala Ala Arg Pro Asn
        35                  40                  45

Pro Leu Gln Val Cys Gly Thr Ala Arg Gly Pro His Val Glu Leu Pro
50                  55                  60

Leu Arg Cys Glu Pro Arg Leu Gly Gln Leu
65                  70

<210> SEQ ID NO 21
<211> LENGTH: 907
<212> TYPE: PRT
<213> ORGANISM: Human cytomegalovirus

<400> SEQUENCE: 21

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205
```

-continued

Lys Thr Met Gln Leu Met Pro Asp Asp Tyr Ser Asn Thr His Ser Thr
210                     215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
            245                 250                 255

Ala Arg Ser Lys Tyr Pro Tyr His Phe Phe Ala Thr Ser Thr Gly Asp
                260             265             270

Val Val Asp Ile Ser Pro Phe Tyr Asn Gly Thr Asn Arg Asn Ala Ser
            275             280             285

Tyr Phe Gly Glu Asn Ala Asp Lys Phe Phe Ile Phe Pro Asn Tyr Thr
290             295             300

Ile Val Ser Asp Phe Gly Arg Pro Asn Ser Ala Leu Glu Thr His Arg
305             310             315             320

Leu Val Ala Phe Leu Glu Arg Ala Asp Ser Val Ile Ser Trp Asp Ile
                325             330             335

Gln Asp Glu Lys Asn Val Thr Cys Gln Leu Thr Phe Trp Glu Ala Ser
            340             345             350

Glu Arg Thr Ile Arg Ser Glu Ala Glu Asp Ser Tyr His Phe Ser Ser
            355             360             365

Ala Lys Met Thr Ala Thr Phe Leu Ser Lys Lys Gln Glu Val Asn Met
370                 375             380

Ser Asp Ser Ala Leu Asp Cys Val Arg Asp Glu Ala Ile Asn Lys Leu
385                 390             395                 400

Gln Gln Ile Phe Asn Thr Ser Tyr Asn Gln Thr Tyr Glu Lys Tyr Gly
                405             410             415

Asn Val Ser Val Phe Glu Thr Thr Gly Gly Leu Val Val Phe Trp Gln
            420             425             430

Gly Ile Lys Gln Lys Ser Leu Val Glu Leu Glu Arg Leu Ala Asn Arg
        435             440             445

Ser Ser Leu Asn Leu Thr His Asn Arg Thr Lys Arg Ser Thr Asp Gly
450                 455             460

Asn Asn Ala Thr His Leu Ser Asn Met Glu Ser Val His Asn Leu Val
465                 470             475                 480

Tyr Ala Gln Leu Gln Phe Thr Tyr Asp Thr Leu Arg Gly Tyr Ile Asn
                485             490             495

Arg Ala Leu Ala Gln Ile Ala Glu Ala Trp Cys Val Asp Gln Arg Arg
            500             505             510

Thr Leu Glu Val Phe Lys Glu Leu Ser Lys Ile Asn Pro Ser Ala Ile
            515             520             525

Leu Ser Ala Ile Tyr Asn Lys Pro Ile Ala Ala Arg Phe Met Gly Asp
530                 535             540

Val Leu Gly Leu Ala Ser Cys Val Thr Ile Asn Gln Thr Ser Val Lys
545             550             555             560

Val Leu Arg Asp Met Asn Val Lys Glu Ser Pro Gly Arg Cys Tyr Ser
            565             570             575

Arg Pro Val Val Ile Phe Asn Phe Ala Asn Ser Ser Tyr Val Gln Tyr
        580             585             590

Gly Gln Leu Gly Glu Asp Asn Glu Ile Leu Leu Gly Asn His Arg Thr
            595             600             605

Glu Glu Cys Gln Leu Pro Ser Leu Lys Ile Phe Ile Ala Gly Asn Ser
610             615             620

Ala Tyr Glu Tyr Val Asp Tyr Leu Phe Lys Arg Met Ile Asp Leu Ser

```
            625                 630                 635                 640
Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
                675                 680                 685

Ser Tyr Lys Gln Arg Val Lys Tyr Val Glu Asp Lys Val Val Asp Pro
                690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
                740                 745                 750

Gly Ala Phe Thr Ile Ile Leu Val Ala Ile Ala Val Val Ile Ile Thr
                755                 760                 765

Tyr Leu Ile Tyr Thr Arg Gln Arg Arg Leu Cys Thr Gln Pro Leu Gln
                770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
                820                 825                 830

Ala Ser Thr Ala Ala Pro Pro Tyr Thr Asn Glu Gln Ala Tyr Gln Met
                835                 840                 845

Leu Leu Ala Leu Ala Arg Leu Asp Ala Glu Gln Arg Ala Gln Gln Asn
                850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Asn Val
                900                 905

<210> SEQ ID NO 22
<211> LENGTH: 907
<212> TYPE: PRT
<213> ORGANISM: Human cytomegalovirus

<400> SEQUENCE: 22

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
                20                  25                  30

Ala Thr His Ser His His Ser Ser His Thr Thr Ser Ala Ala His Ser
                35                  40                  45

Arg Ser Gly Ser Val Ser Gln Arg Val Thr Ser Ser Gln Thr Val Ser
                50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95
```

-continued

Ala Gln Gly Thr Asp Leu Ile Arg Phe Glu Arg Asn Ile Val Cys Thr
                100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile

```
                515                 520                 525
Leu Ser Ala Ile Tyr Asn Lys Pro Ile Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
                595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ser Asn Val Phe Asp Leu Glu Glu Ile Met Arg Glu Phe Asn
                675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
                740                 745                 750

Gly Ala Phe Thr Ile Ile Leu Val Ala Ile Ala Val Val Ile Ile Ile
                755                 760                 765

Tyr Leu Ile Tyr Thr Arg Gln Arg Arg Leu Cys Met Gln Pro Leu Gln
    770                 775                 780

Asn Leu Phe Pro Tyr Leu Val Ser Ala Asp Gly Thr Thr Val Thr Ser
785                 790                 795                 800

Gly Asn Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
                820                 825                 830

Ala Ser Thr Ala Ala Pro Pro Tyr Thr Asn Glu Gln Ala Tyr Gln Met
                835                 840                 845

Leu Leu Ala Leu Val Arg Leu Asp Ala Glu Gln Arg Ala Gln Gln Asn
    850                 855                 860

Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Asn Val
                900                 905

<210> SEQ ID NO 23
<211> LENGTH: 906
<212> TYPE: PRT
<213> ORGANISM: Human cytomegalovirus
```

-continued

```
<400> SEQUENCE: 23

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Ser Ala Gln
            35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
```

-continued

```
                405                 410                 415
Asn Val Ser Val Phe Glu Thr Ser Gly Gly Leu Val Val Phe Trp Gln
                420                 425                 430
Gly Ile Lys Gln Lys Ser Leu Val Glu Leu Glu Arg Leu Ala Asn Arg
                435                 440                 445
Ser Ser Leu Asn Ile Thr His Arg Thr Arg Arg Ser Thr Ser Asp Asn
    450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
                500                 505                 510
Leu Glu Val Phe Lys Glu Leu Ser Lys Ile Asn Pro Ser Ala Ile Leu
                515                 520                 525
Ser Ala Ile Tyr Asn Lys Pro Ile Ala Ala Arg Phe Met Gly Asp Val
    530                 535                 540
Leu Gly Leu Ala Ser Cys Val Thr Ile Asn Gln Thr Ser Val Lys Val
545                 550                 555                 560
Leu Arg Asp Met Asn Val Lys Glu Ser Pro Gly Arg Cys Tyr Ser Arg
                565                 570                 575
Pro Val Val Ile Phe Asn Phe Ala Asn Ser Ser Tyr Val Gln Tyr Gly
                580                 585                 590
Gln Leu Gly Glu Asp Asn Glu Ile Leu Leu Gly Asn His Arg Thr Glu
                595                 600                 605
Glu Cys Gln Leu Pro Ser Leu Lys Ile Phe Ile Ala Gly Asn Ser Ala
    610                 615                 620
Tyr Glu Tyr Val Asp Tyr Leu Phe Lys Arg Met Ile Asp Leu Ser Ser
625                 630                 635                 640
Ile Ser Thr Val Asp Ser Met Ile Ala Leu Asp Ile Asp Pro Leu Glu
                645                 650                 655
Asn Thr Asp Phe Arg Val Leu Glu Leu Tyr Ser Gln Lys Glu Leu Arg
                660                 665                 670
Ser Ser Asn Val Phe Asp Leu Glu Glu Ile Met Arg Glu Phe Asn Ser
    675                 680                 685
Tyr Lys Gln Arg Val Lys Tyr Val Glu Asp Lys Val Val Asp Pro Leu
    690                 695                 700
Pro Pro Tyr Leu Lys Gly Leu Asp Asp Leu Met Ser Gly Leu Gly Ala
705                 710                 715                 720
Ala Gly Lys Ala Val Gly Val Ala Ile Gly Ala Val Gly Gly Ala Val
                725                 730                 735
Ala Ser Val Val Glu Gly Val Ala Thr Phe Leu Lys Asn Pro Phe Gly
                740                 745                 750
Ala Phe Thr Ile Ile Leu Val Ala Ile Ala Val Ile Ile Thr Tyr
                755                 760                 765
Leu Ile Tyr Thr Arg Gln Arg Arg Leu Cys Thr Gln Pro Leu Gln Asn
                770                 775                 780
Leu Phe Pro Tyr Leu Val Ser Ala Asp Gly Thr Thr Val Thr Ser Gly
785                 790                 795                 800
Ser Thr Lys Asp Thr Ser Leu Gln Ala Pro Pro Ser Tyr Glu Glu Ser
                805                 810                 815
Val Tyr Asn Ser Gly Arg Lys Gly Pro Gly Pro Pro Ser Ser Asp Ala
                820                 825                 830
```

-continued

```
Ser Thr Ala Ala Pro Pro Tyr Thr Asn Glu Gln Ala Tyr Gln Met Leu
            835                 840                 845

Leu Ala Leu Ala Arg Leu Asp Ala Glu Gln Arg Ala Gln Gln Asn Gly
        850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
            900                 905
```

<210> SEQ ID NO 24
<211> LENGTH: 7585
<212> TYPE: DNA
<213> ORGANISM: Artificial Sequence
<220> FEATURE:
<223> OTHER INFORMATION: HCMV gH ecto domain fused to C-terminal myc-(his)6 tag

<400> SEQUENCE: 24

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gccaccatga | ggcctggcct | gcctcctac | ctgatcatcc | tggccgtgtg | cctgttcagc | 960 |
| cacctgctgt | ccagcagata | cggcgccgag | gccgtgagcg | agcccctgga | caaggctttc | 1020 |
| cacctgctgc | tgaacaccta | cggcagaccc | atccggtttc | tgcgggagaa | caccacccag | 1080 |
| tgcacctaca | acagcagcct | gcggaacagc | accgtcgtga | gagagaacgc | catcagcttc | 1140 |
| aacttttttcc | agagctacaa | ccagtactac | gtgttccaca | tgccagatg | cctgtttgcc | 1200 |
| ggccctctgg | ccgagcagtt | cctgaaccag | gtggacctga | ccgagacact | ggaaagatac | 1260 |
| cagcagcggc | tgaatacccta | cgccctggtg | tccaaggacc | tggccagcta | ccggtccttt | 1320 |
| agccagcagc | tcaaggctca | ggatagcctc | ggcgagcagc | ctaccaccgt | gcccectccc | 1380 |
| atcgacctga | gcatcccccca | cgtgtggatg | cctccccaga | ccacccctca | cggctggacc | 1440 |
| gagagccaca | ccacctccgg | cctgcacaga | ccccacttca | accagacctg | catcctgttc | 1500 |
| gacggccacg | acctgctgtt | tagcaccgtg | acccctgcc | tgcaccaggg | cttctacctg | 1560 |

```
atcgacgagc tgagatacgt gaagatcacc ctgaccgagg atttcttcgt ggtcaccgtg    1620
tccatcgacg acgacacccc catgctgctg atcttcggcc acctgcccag agtgctgttc    1680
aaggccccct accagcggga caacttcatc ctgcggcaga ccgagaagca cgagctgctg    1740
gtgctggtca agaaggacca gctgaaccgg cactcctacc tgaaggaccc cgacttcctg    1800
gacgccgccc tggacttcaa ctacctggac ctgagcgccc tgctgagaaa cagcttccac    1860
agatacgccg tggacgtgct gaagtccgga cggtgccaga tgctcgatcg gcggaccgtg    1920
gagatggcct tcgcctatgc cctcgccctg ttcgccgctg ccagacagga gaggctggc    1980 gcccaggtgt cagtgcccag agccctggat agacaggccg ccctgctgca gatccaggaa    2040
ttcatgatca cctgcctgag ccagaccccc cctagaacca ccctgctgct gtaccccaca    2100
gccgtggatc tggccaagag ggccctgtgg acccccaacc agatcaccga catcacaagc    2160
ctcgtgcggc tcgtgtacat cctgagcaag cagaaccagc agcacctgat ccccagtgg    2220 gccctgagac agatcgccga cttcgccctg aagctgcaca agacccatct ggccagcttt    2280
ctgagcgcct tcgccaggca ggaactgtac ctgatgggca gctggtcca cagcatgctg    2340 gtgcatacca ccgagcggcg ggagatcttc atcgtggaga caggcctgtg tagcctggcc    2400
gagctgtccc actttaccca gctgctggcc cacccctcacc acgagtacct gagcgacctg    2460 tacacccccct gcagcagcag cggcagacgg gaccacagcc tggaacggct gaccagactg    2520
ttccccgatg ccaccgtgcc tgctacagtg cctgccgccc tgtccatcct gtccaccatg    2580
cagcccagca ccctggaaac cttccccgac ctgttctgcc tgccctggg cgagagcttt    2640 agcgccctga ccgtgtccga gcacgtgtcc tacatcgtga ccaatcagta cctgatcaag    2700
ggcatcagct acccccgtgtc caccacagtc gtgggccaga gcctgatcat caccccagacc    2760 gacagccaga ccaagtgcga gctgacccgg aacatgcaca ccacacacag catcaccgtg    2820
gccctgaaca tcagcctgga aaactgcgct ttctgtcagt ctgccctgct ggaatacgac    2880
gatacccagg gcgtgatcaa catcatgtac atgcacgaca cgacgacgt gctgttcgcc    2940 ctggaccccct acaacgaggt ggtggtgtcc agccccggga cccactacct gatgctgctg    3000
aagaacggca ccgtgctgga agtgaccgac gtggtggtgg acgccaccga cggtaccaag    3060
cttgggcccg aacaaaaact catctcagaa gaggatctga atagcgccgt cgaccatcat    3120
catcatcatc attgagttta acggtctcc agcttaagtt taaaccgctg atcagcctcg    3180
actgtgcctt ctagttgcca gccatctgtt gtttgcccct ccccgtgcc ttccttgacc    3240 ctggaaggtg ccactcccac tgtcctttcc taataaaatg aggaaattgc atcgcattgt    3300
ctgagtaggt gtcattctat tctgggggt ggggtgggc aggacagcaa gggggaggat    3360
tgggaagaca atagcaggca tgctgggat gcggtgggct ctatggcttc tgaggcggaa    3420
agaaccagct ggggctctag ggggtatccc cacgcgccct gtagcggcgc attaagcgcg    3480
gcgggtgtgg tggttacgcg cagcgtgacc gctacacttg ccagcgccct agcgcccgct    3540
cctttcgctt tcttcccttc ctttctcgcc acgttcgccg ctttcccccg tcaagctcta    3600 aatcggggc tccctttagg gttccgattt agtgctttac ggcacctcga ccccaaaaaa    3660
cttgattagg gtgatggttc acgtagtggg ccatcgccct gatagacggt ttttcgccct    3720
ttgacgttgg agtccacgtt ctttaatagt ggactcttgt tccaaactgg aacaacactc    3780
aaccctatct cggtctattc ttttgattta agggatt tgccgatttc ggcctattgg    3840
ttaaaaaatg agctgattta acaaaaattt aacgcgaatt aattctgtgg aatgtgtgtc    3900
agttagggtg tggaaagtcc ccaggctccc cagcaggcag aagtatgcaa agcatgcatc    3960
```

```
tcaattagtc agcaaccagg tgtggaaagt ccccaggctc cccagcaggc agaagtatgc    4020
aaagcatgca tctcaattag tcagcaacca tagtcccgcc cctaactccg cccatcccgc    4080
ccctaactcc gcccagttcc gcccattctc cgccccatgg ctgactaatt ttttttattt    4140
atgcagaggc cgaggccgcc tctgcctctg agctattcca gaagtagtga ggaggctttt    4200
ttggaggcct aggcttttgc aaaaagctcc cgggagcttg tatatccatt ttcggatctg    4260
atcaagagac aggatgagga tcgtttcgca tgattgaaca agatggattg cacgcaggtt    4320
ctccggccgc ttgggtggag aggctattcg gctatgactg gcacaacaga caatcggct     4380 gctctgatgc cgccgtgttc cggctgtcag cgcaggggcg cccggttctt tttgtcaaga    4440
ccgacctgtc cggtgccctg aatgaactgc aggacgaggc agcgcggcta tcgtggctgg    4500
ccacgacggg cgttccttgc gcagctgtgc tcgacgttgt cactgaagcg ggaagggact    4560
ggctgctatt gggcgaagtg ccggggcagg atctcctgtc atctcacctt gctcctgccg    4620
agaaagtatc catcatggct gatgcaatgc ggcggctgca tacgcttgat ccggctacct    4680
gcccattcga ccaccaagcg aaacatcgca tcgagcgagc acgtactcgg atggaagccg    4740
gtcttgtcga tcaggatgat ctggacgaag agcatcaggg gctcgcgcca gccgaactgt    4800
tcgccaggct caaggcgcgc atgcccgacg gcgaggatct cgtcgtgacc catggcgatg    4860
cctgcttgcc gaatatcatg gtggaaaatg gccgcttttc tggattcatc gactgtggcc    4920
ggctgggtgt ggcggaccgc tatcaggaca tagcgttggc tacccgtgat attgctgaag    4980
agcttggcgg cgaatgggct gaccgcttcc tcgtgcttta cggtatcgcc gctcccgatt    5040
cgcagcgcat cgccttctat cgccttcttg acgagttctt ctgagcggga ctctgggtt     5100 cgaaatgacc gaccaagcga cgcccaacct gccatcacga atttcgatt ccaccgccgc     5160 cttctatgaa aggttgggct tcggaatcgt tttccgggac gccggctgga tgatcctcca    5220
gcgcggggat ctcatgctgg agttcttcgc ccaccccaac ttgtttattg cagcttataa    5280
tggttacaaa taaagcaata gcatcacaaa tttcacaaat aaagcatttt tttcactgca    5340
ttctagttgt ggtttgtcca aactcatcaa tgtatcttat catgtctgta taccgtcgac    5400
ctctagctag agcttggcgt aatcatggtc atagctgttt cctgtgtgaa attgttatcc    5460
gctcacaatt ccacacaaca tacgagccgg aagcataaag tgtaaagcct ggggtgccta    5520
atgagtgagc taactcacat taattgcgtt gcgctcactg cccgctttcc agtcgggaaa    5580
cctgtcgtgc cagctgcatt aatgaatcgg ccaacgcgcg gggagaggcg gtttgcgtat    5640
tgggcgctct tccgcttcct cgctcactga ctcgctgcgc tcggtcgttc ggctgcggcg    5700
agcggtatca gctcactcaa aggcggtaat acggttatcc acagaatcag gggataacgc    5760
aggaaagaac atgtgagcaa aaggccagca aaaggccagg aaccgtaaaa aggccgcgtt    5820
gctggcgttt ttccataggc tccgcccccc tgacgagcat cacaaaaatc gacgctcaag    5880
tcagaggtgg cgaaacccga caggactata aagataccag gcgtttcccc ctggaagctc    5940
cctcgtgcgc tctcctgttc cgaccctgcc gcttaccgga tacctgtccg cctttctccc    6000
ttcgggaagc gtggcgcttt ctcatagctc acgctgtagg tatctcagtt cggtgtaggt    6060
cgttcgctcc aagctgggct gtgtgcacga accccccgtt cagcccgacc gctgcgcctt    6120
atccggtaac tatcgtcttg agtccaaccc ggtaagacac gacttatcgc cactggcagc    6180
agccactggt aacaggatta gcagagcgag gtatgtaggc ggtgctacag agttcttgaa    6240
gtggtggcct aactacggct acactagaag aacagtattt ggtatctgcg ctctgctgaa    6300
```

```
gccagttacc ttcggaaaaa gagttggtag ctcttgatcc ggcaaacaaa ccaccgctgg    6360
tagcggtggt ttttttgttt gcaagcagca gattacgcgc agaaaaaaag gatctcaaga    6420
agatcctttg atcttttcta cggggtctga cgctcagtgg aacgaaaact cacgttaagg    6480
gattttggtc atgagattat caaaaaggat cttcacctag atcctttaa attaaaaatg     6540 aagttttaaa tcaatctaaa gtatatatga gtaaacttgg tctgacagtt accaatgctt    6600
aatcagtgag gcacctatct cagcgatctg tctatttcgt tcatccatag ttgcctgact    6660
ccccgtcgtg tagataacta cgatacggga gggcttacca tctggcccca gtgctgcaat    6720
gataccgcga gacccacgct caccggctcc agatttatca gcaataaacc agccagccgg    6780
aagggccgag cgcagaagtg gtcctgcaac tttatccgcc tccatccagt ctattaattg    6840
ttgccgggaa gctagagtaa gtagttcgcc agttaatagt ttgcgcaacg ttgttgccat    6900
tgctacaggc atcgtggtgt cacgctcgtc gtttggtatg gcttcattca gctccggttc    6960
ccaacgatca aggcgagtta catgatcccc catgttgtgc aaaaaagcgg ttagctcctt    7020
cggtcctccg atcgttgtca gaagtaagtt ggccgcagtg ttatcactca tggttatggc    7080
agcactgcat aattctctta ctgtcatgcc atccgtaaga tgcttttctg tgactggtga    7140
gtactcaacc aagtcattct gagaatagtg tatgcggcga ccgagttgct cttgcccggc    7200
gtcaatacgg gataataccg cgccacatag cagaacttta aaagtgctca tcattggaaa    7260
acgttcttcg gggcgaaaac tctcaaggat cttaccgctg ttgagatcca gttcgatgta    7320
acccactcgt gcacccaact gatcttcagc atcttttact ttcaccagcg tttctgggtg    7380
agcaaaaaca ggaaggcaaa atgccgcaaa aaagggaata agggcgacac ggaaatgttg    7440
aatactcata ctcttccttt ttcaatatta ttgaagcatt tatcagggtt attgtctcat    7500
gagcggatac atatttgaat gtatttagaa aaataaacaa ataggggttc cgcgcacatt    7560
tccccgaaaa gtgccacctg acgtc                                         7585
```

<210> SEQ ID NO 25
<211> LENGTH: 5156
<212> TYPE: DNA
<213> ORGANISM: Human cytomegalovirus

<400> SEQUENCE: 25

```
gccgcggaat tcgactcta ggccattgca tacgttgtat ctatatcata atatgtacat      60
ttatattggc tcatgtccaa tatgaccgcc atgttgacat tgattattga ctagttatta    120
atagtaatca attacggggt cattagttca tagcccatat atggagttcc gcgttacata    180
acttacggta aatggcccgc ctggctgacc gcccaacgac ccccgcccat tgacgtcaat    240
aatgacgtat gttcccatag taacgccaat agggactttc cattgacgtc aatgggtgga    300
gtatttacgg taaactgccc acttggcagt acatcaagtg tatcatatgc caagtccgcc    360
ccctattgac gtcaatgacg gtaaatggcc cgcctggcat tatgcccagt acatgacctt    420
acgggacttt cctacttggc agtacatcta cgtattagtc atcgctatta ccatggtgat    480
gcggttttgg cagtacacca atgggcgtgg atagcggttt gactcacggg atttccaag    540 tctccacccc attgacgtca atgggagttt gttttggcac caaaatcaac gggactttcc    600
aaaatgtcgt aataaccccg ccccgttgac gcaaatgggc ggtaggcgtg tacggtggga    660
ggtctatata agcagagctc gtttagtgaa ccgtcagatc gcctggagac gccatccacg    720
ctgttttgac ctccatagaa gacaccggga ccgatccagc ctccgcggcc gggaacggtg    780
cattggaacg cggattcccc gtgccaagag tgacgtaagt accgcctata gactctatag    840
```

```
gcacacccct ttggctctta tgcatgctat actgttttg gcttgggcc tatacacccc      900
cgcttcctta tgctataggt gatggtatag cttagcctat aggtgtgggt tattgaccat     960
tattgaccac tccctattg gtgacgatac tttccattac taatccataa catggctctt    1020
tgccacaact atctctattg gctatatgcc aatactctgt ccttcagaga ctgacacgga    1080
ctctgtattt ttacaggatg ggtcccatt tattatttac aaattcacat atacaacaac    1140
gccgtccccc gtgccgcag tttttattaa acatagcgtg ggatctccac gcgaatctcg    1200
ggtacgtgtt ccggacatgg gctcttctcc ggtagcggcg gagcttccac atccgagccc    1260
tggtcccatg cctccagcgg ctcatggtcg ctcggcagct ccttgctcct aacagtggag    1320
gccagactta ggcacagcac aatgcccacc accaccagtg tgccgcacaa ggccgtggcg    1380
gtagggtatg tgtctgaaaa tgagctcgga gattgggctc gcaccgctga cgcagatgga    1440
agacttaagg cagcggcaga agaagatgca ggcagctgag ttgttgtatt ctgataagag    1500
tcagaggtaa ctcccgttgc ggtgctgtta acggtggagg gcagtgtagt ctgagcagta    1560
ctcgttgctg ccgcgcgcgc caccagacat aatagctgac agactaacag actgttcctt    1620
tccatgggtc ttttctgcag tcaccgtcgt cgacgccacc atgtgcagaa ggcccgactg    1680
cggcttcagc ttcagccctg gacccgtgat cctgctgtgg tgctgcctgc tgctgcctat    1740
cgtgtcctct gccgccgtgt ctgtggcccc tacagccgcc gagaaggtgc agccgagtg    1800
ccccgagctg accagaagat gcctgctggg cgaggtgttc gagggcgaca gtacgagag    1860
ctggctgcgg cccctggtca acgtgaccgg cagagatggc cccctgagcc agctgatccg    1920
gtacagaccc gtgacccccg aggccgccaa tagcgtgctg ctggacgagg ccttcctgga    1980
taccctggcc ctgctgtaca acaacccga ccagctgaga gccctgctga ccctgctgtc    2040
cagcgacacc gccccagat ggatgaccgt gatgcgggc tacagcgagt gtggagatgg    2100
cagccctgcc gtgtacacct gcgtggacga cctgtgcaga ggctacgacc tgaccagact    2160
gagctacggc cggtccatct tcacagagca cgtgctgggc ttcgagctgg tgccccccag    2220
cctgttcaac gtggtggtgg ccatccggaa cgaggccacc agaaccaaca gagccgtgcg    2280
gctgcctgtg tctacagccg ctgcacctga gggcatcaca ctgttctacg gcctgtacaa    2340
cgccgtgaaa gagttctgcc tccggcacca gctggatccc cccctgctga cacctggaga    2400
caagtactac gccggcctgc ccccagagct gaagcagacc agagtgaacc tgcccgccca    2460
cagcagatat ggccctcagg ccgtggacgc cagatgataa tctagaaagc catggatatc    2520
ggatccacta cgcgttagag ctcgctgatc agcctcgact gtgccttcta gttgccagcc    2580
atctgttgtt tgcccctccc ccgtgccttc cttgaccctg gaaggtgcca ctcccactgt    2640
ccttcctaa taaatgagg aaattgcatc gcattgtctg agtaggtgtc attctattct    2700
ggggggtggg gtggcagg acagcaaggg ggaggattgg gaagacaata gcaggggt      2760
gggcgaagaa ctccagcatg agatcccgc gctggaggat catccagccg cgtcccgga    2820
aaacgattcc gaagcccaac cttcataga aggcggcggt ggaatcgaaa tctcgtgatg    2880
gcaggttggg cgtcgcttgg tcggtcattt cgaaccccag agtcccgctc agaagaactc    2940
gtcaagaagg cgatagaagg cgatgcgctg cgaatcggga gcggcgatac cgtaaagcac    3000
gaggaagcgg tcagcccatt cgccgccaag ctcttcagca atatcacggg tagccaacgc    3060
tatgtcctga tagcggtccg ccacacccag ccggccacag tcgatgaatc cagaaaagcg    3120
gccattttcc accatgatat tcggcaagca ggcatcgcca tgggtcacga cgagatcctc    3180
```

| | |
|---|---|
| gccgtcgggc atgcgcgcct tgagcctggc gaacagttcg gctggcgcga gcccctgatg | 3240 |
| ctcttcgtcc agatcatcct gatcgacaag accggcttcc atccgagtac gtgctcgctc | 3300 |
| gatgcgatgt ttcgcttggt ggtcgaatgg gcaggtagcc ggatcaagcg tatgcagccg | 3360 |
| ccgcattgca tcagccatga tggatacttt ctcggcagga gcaaggtgag atgacaggag | 3420 |
| atcctgcccc ggcacttcgc ccaatagcag ccagtcccct cccgcttcag tgacaacgtc | 3480 |
| gagcacagct gcgcaaggaa cgcccgtcgt ggccagccac gatagccgcg ctgcctcgtc | 3540 |
| ctgcagttca ttcagggcac cggacaggtc ggtcttgaca aaagaaccg gcgcccctg | 3600 |
| cgctgacagc cggaacacgg cggcatcaga gcagccgatt gtctgttgtg cccagtcata | 3660 |
| gccgaatagc ctctccaccc aagcggccgg agaacctgcg tgcaatccat cttgttcaat | 3720 |
| catgcgaaac gatcctcatc ctgtctcttg atcagatctt gatcccctgc gccatcagat | 3780 |
| ccttggcggc aagaaagcca tccagtttac tttgcagggc ttcccaacct taccagaggg | 3840 |
| cgccccagct ggcaattccg gttcgcttgc tgtccataaa accgccagt ctagctatcg | 3900 |
| ccatgtaagc ccactgcaag ctacctgctt tctctttgcg cttgcgtttt cccttgtcca | 3960 |
| gatagcccag tagctgacat tcatccgggg tcagcaccgt ttctgcggac tggctttcta | 4020 |
| cgtgttccgc ttcctttagc agcccttgcg ccctgagtgc ttgcggcagc gtgaagctaa | 4080 |
| ttcatggtta aattttgtt aaatcagctc attttttaac caataggccg aaatcggcaa | 4140 |
| aatcccttat aaatcaaaag aatagcccga atagggttg agtgttgttc cagtttggaa | 4200 |
| caagagtcca ctattaaaga acgtggactc caacgtcaaa gggcgaaaaa ccgtctatca | 4260 |
| gggcgatggc cggatcagct tatgcggtgt gaaataccgc acagatgcgt aaggagaaaa | 4320 |
| taccgcatca ggcgctcttc cgcttcctcg ctcactgact cgctgcgctc ggtcgttcgg | 4380 |
| ctgcggcgag cggtatcagc tcactcaaag gcggtaatac ggttatccac agaatcaggg | 4440 |
| gataacgcag gaaagaacat gtgagcaaaa ggccagcaaa aggccaggaa ccgtaaaaag | 4500 |
| gccgcgttgc tggcgttttt ccataggctc cgccccctg acgagcatca caaaatcga | 4560 |
| cgctcaagtc agaggtggcg aaacccgaca ggactataaa gataccaggc gtttccccct | 4620 |
| ggaagctccc tcgtgcgctc tcctgttccg accctgccgc ttaccggata cctgtccgcc | 4680 |
| tttctccctt cgggaagcgt ggcgctttct catagctcac gctgtaggta tctcagttcg | 4740 |
| gtgtaggtcg ttcgctccaa gctgggctgt gtgcacgaac cccccgttca gcccgaccgc | 4800 |
| tgcgccttat ccggtaacta tcgtcttgag tccaacccgg taagacacga cttatcgcca | 4860 |
| ctggcagcag ccactggtaa caggattagc agagcgaggt atgtaggcgg tgctacagag | 4920 |
| ttcttgaagt ggtggcctaa ctacggctac actagaagga cagtatttgg tatctgcgct | 4980 |
| ctgctgaagc cagttacctt cggaaaaaga gttggtagct cttgatccgg caaacaaacc | 5040 |
| accgctggta gcggtggttt ttttgtttgc aagcagcaga ttacgcgcag aaaaaaagga | 5100 |
| tctcaagaag atcctttgat ctttttctact gaacggtgat ccccaccgga attgcg | 5156 |

```
<210> SEQ ID NO 26
<211> LENGTH: 4835
<212> TYPE: DNA
<213> ORGANISM: Human cytomegalovirus

<400> SEQUENCE: 26
```

| | |
|---|---|
| gccgcggaat ttcgactcta ggccattgca tacgttgtat ctatatcata atatgtacat |   60 |
| ttatattggc tcatgtccaa tatgaccgcc atgttgacat tgattattga ctagttatta |  120 |
| atagtaatca attacggggt cattagttca tagcccatat atggagttcc gcgttacata |  180 |

```
acttacggta aatggcccgc ctggctgacc gcccaacgac ccccgcccat tgacgtcaat      240
aatgacgtat gttcccatag taacgccaat agggactttc cattgacgtc aatgggtgga      300
gtatttacgg taaactgccc acttggcagt acatcaagtg tatcatatgc caagtccgcc      360
ccctattgac gtcaatgacg gtaaatggcc cgcctggcat tatgcccagt acatgacctt      420
acgggacttt cctacttggc agtacatcta cgtattagtc atcgctatta ccatggtgat      480
gcggttttgg cagtacacca atgggcgtgg atagcggttt gactcacggg gatttccaag      540
tctccacccc attgacgtca atgggagttt gttttggcac caaaatcaac gggactttcc      600
aaaatgtcgt aataaccccg ccccgttgac gcaaatgggc ggtaggcgtg tacggtggga      660
ggtctatata agcagagctc gtttagtgaa ccgtcagatc gcctggagac gccatccacg      720
ctgttttgac ctccatagaa gacaccggga ccgatccagc ctccgcggcc gggaacggtg      780
cattggaacg cggattcccc gtgccaagag tgacgtaagt accgcctata gactctatag      840
gcacacccct ttggctctta tgcatgctat actgtttttg gcttgggcc tatacacccc       900 cgcttcctta tgctataggt gatggtatag cttagcctat aggtgtgggt tattgaccat      960
tattgaccac tcccctattg gtgacgatac tttccattac taatccataa catggctctt     1020
tgccacaact atctctattg gctatatgcc aatactctgt ccttcagaga ctgacacgga     1080
ctctgtattt ttacaggatg ggtcccatt tattatttac aaattcacat atacaacaac      1140
gccgtccccc gtgcccgcag ttttattaa acatagcgtg ggatctccac gcgaatctcg      1200
ggtacgtgtt ccggacatgg gctcttctcc ggtagcggcg gagcttccac atccgagccc     1260
tggtcccatg cctccagcgg ctcatggtcg ctcggcagct ccttgctcct aacagtggag     1320
gccagactta ggcacagcac aatgcccacc accaccagtg tgccgcacaa ggccgtggcg     1380
gtagggtatg tgtctgaaaa tgagctcgga gattgggctc gcaccgctga cgcagatgga     1440
agacttaagg cagcggcaga agaagatgca ggcagctgag ttgttgtatt ctgataagag     1500
tcagaggtaa ctcccgttgc ggtgctgtta acggtggagg gcagtgtagt ctgagcagta     1560
ctcgttgctg ccgcgcgcgc caccagacat aatagctgac agactaacag actgttcctt     1620
tccatgggtc tttctgcag tcaccgtcgt cgacgccacc atgagcccca aggacctgac      1680
ccccttcctg acaaccctgt ggctgctcct gggccatagc agagtgccta gagtgcgggc     1740
cgaggaatgc tgcgagttca tcaacgtgaa ccacccccc gagcggtgct acgacttcaa      1800
gatgtgcaac cggttcaccg tggccctgag atgccccgac ggcgaagtgt gctacagccc     1860
cgagaaaacc gccgagatcc ggggcatcgt gaccaccatg acccacagcc tgaccccgca     1920
ggtggtgcac aacaagctga ccagctgcaa ctacaaccc ctgtacctgg aagccgacgg      1980
ccggatcaga tgcggcaaag tgaacgacaa ggcccagtac ctgctgggag ccgcggaag     2040 cgtgccctac cggtggatca acctggaata cgacaagatc acccggatcg tgggcctgga     2100
ccagtacctg gaaagcgtga agaagcacaa gcggctggac gtgtgcagag ccaagatggg     2160
ctacatgctg cagtgataat ctagaaagcc atggatatcg gatccactac gcgttagagc     2220
tcgctgatca gcctcgactg tgccttctag ttgccagcca tctgttgttt gcccctcccc     2280
cgtgccttcc ttgaccctgg aaggtgccac tcccactgtc ctttcctaat aaaatgagga     2340
aattgcatcg cattgtctga gtaggtgtca ttctattctg gggggtgggg tggggcagga     2400
cagcaagggg gaggattggg aagacaatag caggggggtg ggcgaagaac tccagcatga     2460
gatccccgcg ctggaggatc atccagccgg cgtcccggaa aacgattccg aagcccaacc     2520
```

```
tttcatagaa ggcggcggtg gaatcgaaat ctcgtgatgg caggttgggc gtcgcttggt      2580
cggtcatttc gaaccccaga gtcccgctca aagaactcg tcaagaaggc gatagaaggc       2640
gatgcgctgc gaatcgggag cggcgatacc gtaaagcacg aggaagcggt cagcccattc      2700
gccgccaagc tcttcagcaa tatcacgggt agccaacgct atgtcctgat agcggtccgc      2760
cacacccagc cggccacagt cgatgaatcc agaaaagcgg ccattttcca ccatgatatt      2820
cggcaagcag gcatcgccat gggtcacgac gagatcctcg ccgtcgggca tgcgcgcctt      2880
gagcctggcg aacagttcgg ctggcgcgag ccctgatgc tcttcgtcca gatcatcctg       2940
atcgacaaga ccggcttcca tccgagtacg tgctcgctcg atgcgatgtt tcgcttggtg      3000
gtcgaatggg caggtagccg gatcaagcgt atgcagccgc cgcattgcat cagccatgat      3060
ggatactttc tcggcaggag caaggtgaga tgacaggaga tcctgccccg gcacttcgcc      3120
caatagcagc cagtcccttc ccgcttcagt gacaacgtcg agcacagctg cgcaaggaac      3180
gcccgtcgtg gccagccacg atagccgcg tgcctcgtcc tgcagttcat tcagggcacc      3240
ggacaggtcg gtcttgacaa aagaaccgg gcgcccctgc gctgacagcc ggaacacggc       3300
ggcatcagag cagccgattg tctgttgtgc ccagtcatag ccgaatagcc tctccaccca      3360
agcggccgga gaacctgcgt gcaatccatc ttgttcaatc atgcgaaacg atcctcatcc      3420
tgtctcttga tcagatcttg atccctgcg ccatcagatc cttggcggca agaaagccat       3480
ccagtttact ttgcagggct tcccaacctt accagagggc gccccagctg caattccgg       3540 ttcgcttgct gtccataaaa ccgcccagtc tagctatcgc catgtaagcc cactgcaagc      3600
tacctgcttt ctctttgcgc ttgcgttttc ccttgtccag atagcccagt agctgacatt      3660
catccggggt cagcaccgtt tctgcggact ggctttctac gtgttccgct tcctttagca      3720
gcccttgcgc cctgagtgct tgcggcagcg tgaagctaat tcatggttaa attttgtta      3780 aatcagctca ttttttaacc aataggccga aatcggcaaa atcccttata aatcaaaga      3840 atagcccgag atagggttga gtgttgttcc agtttggaac aagagtccac tattaaagaa      3900
cgtggactcc aacgtcaaag ggcgaaaaac cgtctatcag ggcgatggcc ggatcagctt      3960
atgcggtgtg aaataccgca cagatgcgta aggagaaaat accgcatcag gcgctcttcc      4020
gcttcctcgc tcactgactc gctgcgctcg gtcgttcggc tgcggcgagc ggtatcagct      4080
cactcaaagg cggtaatacg gttatccaca gaatcagggg ataacgcagg aaagaacatg      4140
tgagcaaaag gccagcaaaa ggccaggaac cgtaaaaagg ccgcgttgct ggcgtttttc      4200
cataggctcc gccccctga cgagcatcac aaaaatcgac gctcaagtca gaggtggcga       4260
aacccgacag gactataaag ataccaggcg tttccccctg gaagctccct cgtgcgctct      4320
cctgttccga ccctgccgct taccggatac ctgtccgcct ttctcccttc gggaagcgtg      4380
gcgctttctc atagctcacg ctgtaggtat ctcagttcgg tgtaggtcgt tcgctccaag      4440
ctgggctgtg tgcacgaacc cccgttcag cccgaccgct gcgccttatc cggtaactat       4500
cgtcttgagt ccaacccggt aagacacgac ttatcgccac tggcagcagc cactggtaac      4560
aggattagca gagcgaggta tgtaggcggt gctacagagt tcttgaagtg gtggcctaac      4620
tacggctaca ctagaaggac agtatttggt atctgcgctc tgctgaagcc agttaccttc      4680
ggaaaaagag ttggtagctc ttgatccggc aaacaaacca ccgctggtag cggtggtttt      4740
tttgtttgca agcagcagat tacgcgcaga aaaaaaggat ctcaagaaga tcctttgatc      4800
ttttctactg aacggtgatc cccaccggaa ttgcg                                 4835
```

```
<210> SEQ ID NO 27
<211> LENGTH: 4964
<212> TYPE: DNA
<213> ORGANISM: Human cytomegalovirus

<400> SEQUENCE: 27
gccgcggaat tcgactcta ggccattgca tacgttgtat ctatatcata atatgtacat      60
ttatattggc tcatgtccaa tatgaccgcc atgttgacat tgattattga ctagttatta    120
atagtaatca attacggggt cattagttca tagcccatat atggagttcc gcgttacata    180
acttacggta aatggcccgc ctggctgacc gcccaacgac ccccgcccat tgacgtcaat    240
aatgacgtat gttcccatag taacgccaat agggactttc cattgacgtc aatgggtgga    300
gtatttacgg taaactgccc acttggcagt acatcaagtg tatcatatgc caagtccgcc    360
ccctattgac gtcaatgacg gtaaatggcc cgcctggcat tatgcccagt acatgacctt    420
acgggacttt cctacttggc agtacatcta cgtattagtc atcgctatta ccatggtgat    480
gcggttttgg cagtacacca atgggcgtgg atagcggttt gactcacggg gatttccaag    540
tctccacccc attgacgtca atgggagttt gttttggcac caaaatcaac gggactttcc    600
aaaatgtcgt aataacccg ccccgttgac gcaaatgggc ggtaggcgtg tacggtggga    660
ggtctatata agcagagctc gtttagtgaa ccgtcagatc gcctggagac gccatccacg    720
ctgttttgac ctccatagaa gacaccggga ccgatccagc ctccgcggcc gggaacggtg    780
cattggaacg cggattcccc gtgccaagag tgacgtaagt accgcctata gactctatag    840
gcacacccct ttggctctta tgcatgctat actgttttg gcttgggcc tatacacccc      900 cgcttccta tgctataggt gatggtatag cttagcctat aggtgtgggt tattgaccat    960
tattgaccac tcccctattg gtgacgatac tttccattac taatccataa catggctctt   1020
tgccacaact atctctattg gctatatgcc aatactctgt ccttcagaga ctgacacgga   1080
ctctgtattt ttacaggatg ggtcccatt tattatttac aaattcacat atacaacaac   1140
gccgtccccc gtgcccgcag ttttattaa acatagcgtg ggatctccac gcgaatctcg   1200
ggtacgtgtt ccggacatgg gctcttctcc ggtagcggcg gagcttccac atccgagccc   1260
tggtcccatg cctccagcgg ctcatggtcg ctcggcagct ccttgctcct aacagtggag   1320
gccagactta ggcacagcac aatgcccacc accaccagtg tgccgcacaa ggccgtggcg   1380
gtagggtatg tgtctgaaaa tgagctcgga gattgggctc gcaccgctga cgcagatgga   1440
agacttaagg cagcggcaga agaagatgca ggcagctgag ttgttgtatt ctgataagag   1500
tcagaggtaa ctcccgttgc ggtgctgtta acggtggagg gcagtgtagt ctgagcagta   1560
ctcgttgctg ccgcgcgcgc caccagacat aatagctgac agactaacag actgttcctt   1620 tccatggtc ttttctgcag tcaccgtcgt cgacgccacc atgctgcggc tgctgctgag   1680 acaccactc cactgcctgc tgctgtgtgc cgtgtgggcc accccttgtc tggccagccc   1740
ttggagcacc ctgaccgcca accagaaccc tagccccct tggtccaagc tgacctacag   1800
caagccccac gacgccgcca ccttctactg cccctttctg taccccagcc ctcccagaag   1860 cccccctgcag ttcagcggct tccagagagt gtccaccggc cctgagtgcc ggaacgagac   1920
actgtacctg ctgtacaacc gggagggcca gacactggtg gagcggagca gcacctgggt   1980 gaaaaagtg atctggtatc tgagcggccg gaaccagacc atcctgcagc ggatgcccag   2040
aaccgccagc aagcccagcg acggcaacgt gcagatcagc gtggaggacg ccaaaatctt   2100
cggcgcccac atggtgccca gcagaccaa gctgctgaga ttcgtggtca acgacggcac   2160
```

```
cagatatcag atgtgcgtga tgaagctgga aagctgggcc cacgtgttcc gggactactc   2220
cgtgagcttc caggtccggc tgaccttcac cgaggccaac aaccagacct acaccttctg   2280
cacccacccc aacctgatcg tgtgataatc tagaaagcca tggatatcgg atccactacg   2340
cgttagagct cgctgatcag cctcgactgt gccttctagt tgccagccat ctgttgtttg   2400
cccctcccc gtgccttcct tgaccctgga aggtgccact cccactgtcc tttcctaata   2460
aaatgaggaa attgcatcgc attgtctgag taggtgtcat tctattctgg ggggtggggt   2520
ggggcaggac agcaagggg aggattggga agacaatagc aggggggtgg gcgaagaact   2580
ccagcatgag atccccgcgc tggaggatca tccagccggc gtcccggaaa acgattccga   2640
agcccaacct ttcatagaag gcggcggtgg aatcgaaatc tcgtgatggc aggttgggcg   2700
tcgcttggtc ggtcatttcg aaccccagag tcccgctcag aagaactcgt caagaaggcg   2760
atagaaggcg atgcgctgcg aatcgggagc ggcgataccg taaagcacga ggaagcggtc   2820
agcccattcg ccgccaagct cttcagcaat atcacgggta gccaacgcta tgtcctgata   2880
gcggtccgcc acacccagcc ggccacagtc gatgaatcca gaaaagcggc cattttccac   2940
catgatattc ggcaagcagg catcgccatg ggtcacgacg agatcctcgc cgtcgggcat   3000
gcgcgccttg agcctggcga acagttcggc tggcgcgagc cctgatgct cttcgtccag   3060
atcatcctga tcgacaagac cggcttccat ccgagtacgt gctcgctcga tgcgatgttt   3120
cgcttggtgg tcgaatgggc aggtagccgg atcaagcgta tgcagccgcc gcattgcatc   3180
agccatgatg gatactttct cggcaggagc aaggtgagat gacaggagat cctgccccgg   3240
cacttcgccc aatagcagcc agtcccttcc cgcttcagtg acaacgtcga gcacagctgc   3300
gcaaggaacg cccgtcgtgg ccagccacga tagccgcgct gcctcgtcct gcagttcatt   3360
cagggcaccg gacaggtcgg tcttgacaaa aagaaccggg cgcccctgcg ctgacagccg   3420
gaacacggcg gcatcagagc agccgattgt ctgttgtgcc cagtcatagc cgaatagcct   3480
ctccacccaa gcggccggag aacctgcgtg caatccatct tgttcaatca tgcgaaacga   3540
tcctcatcct gtctcttgat cagatcttga tccctgcgc catcagatcc ttggcggcaa   3600
gaaagccatc cagtttactt tgcagggctt cccaaccta ccagagggcg cccccagctgg   3660
caattccggt tcgcttgctg tccataaaac cgcccagtct agctatcgcc atgtaagccc   3720
actgcaagct acctgctttc tctttgcgct tgcgttttcc cttgtccaga tagcccagta   3780
gctgacattc atccggggtc agcaccgttt ctgcggactg gctttctacg tgttccgctt   3840
cctttagcag cccttgcgcc ctgagtgctt gcggcagcgt gaagctaatt catggttaaa   3900
tttttgttaa atcagctcat tttttaacca ataggccgaa atcggcaaaa tcccttataa   3960
atcaaaagaa tagcccgaga tagggttgag tgttgttcca gtttggaaca agagtccact   4020
attaaagaac gtggactcca acgtcaaagg gcgaaaaacc gtctatcagg gcgatggccg   4080
gatcagctta tgcggtgtga ataccgcac agatgcgtaa ggagaaaata ccgcatcagg   4140
cgctcttccg cttcctcgct cactgactcg ctgcgctcgg tcgttcggct gcggcgagcg   4200
gtatcagctc actcaaaggc ggtaatacgg ttatccacag aatcaggga taacgcagga   4260
aagaacatgt gagcaaaagg ccagcaaaag gccaggaacc gtaaaaaggc cgcgttgctg   4320
gcgtttttcc ataggctccg ccccctgac gagcatcaca aaaatcgacg ctcaagtcag   4380
aggtggcgaa acccgacagg actataaaga taccaggcgt ttccccctgg aagctccctc   4440
gtgcgctctc ctgttccgac cctgccgctt accggatacc tgtccgcctt tctcccttcg   4500
ggaagcgtgg cgctttctca tagctcacgc tgtaggtatc tcagttcggt gtaggtcgtt   4560
```

```
cgctccaagc tgggctgtgt gcacgaaccc ccgttcagc ccgaccgctg cgccttatcc    4620
ggtaactatc gtcttgagtc caacccggta agacacgact tatcgccact ggcagcagcc    4680
actggtaaca ggattagcag agcgaggtat gtaggcggtg ctacagagtt cttgaagtgg    4740
tggcctaact acggctacac tagaaggaca gtatttggta tctgcgctct gctgaagcca    4800
gttaccttcg aaaaagagt tggtagctct tgatccggca acaaaccac cgctggtagc    4860 ggtggttttt ttgtttgcaa gcagcagatt acgcgcagaa aaaaggatc tcaagaagat    4920 cctttgatct tttctactga acggtgatcc ccaccggaat tgcg                    4964
```

<210> SEQ ID NO 28
<211> LENGTH: 4709
<212> TYPE: DNA
<213> ORGANISM: Human cytomegalovirus

<400> SEQUENCE: 28

```
gccgcggaat tcgactcta ggccattgca tacgttgtat ctatatcata atatgtacat      60
ttatattggc tcatgtccaa tatgaccgcc atgttgacat tgattattga ctagttatta    120
atagtaatca attacggggt cattagttca tagcccatat atggagttcc gcgttacata    180
acttacggta aatggcccgc ctggctgacc gcccaacgac ccccgcccat tgacgtcaat    240
aatgacgtat gttcccatag taacgccaat agggactttc cattgacgtc aatgggtgga    300
gtatttacgg taaactgccc acttggcagt acatcaagtg tatcatatgc caagtccgcc    360
ccctattgac gtcaatgacg gtaaatggcc cgcctggcat tatgcccagt acatgacctt    420
acgggacttt cctacttggc agtacatcta cgtattagtc atcgctatta ccatggtgat    480
gcggttttgg cagtacacca tgggcgtgg atagcggttt gactcacggg gatttccaag    540
tctccacccc attgacgtca atgggagttt gttttggcac caaaatcaac gggactttcc    600
aaaatgtcgt aataacccccg ccccgttgac gcaaatgggc ggtaggcgtg tacggtggga    660
ggtctatata agcagagctc gtttagtgaa ccgtcagatc gcctggagac gccatccacg    720
ctgttttgac ctccatagaa gacaccggga ccgatccagc ctccgcgcc gggaacggtg    780 cattggaacg cggattcccc gtgccaagag tgacgtaagt accgcctata gactctatag    840
gcacacccct ttggctctta tgcatgctat actgttttg cttggggcc tatacacccc    900 cgcttcctta tgctataggt gatggtatag cttagcctat aggtgtgggt tattgaccat    960
tattgaccac tccctattg gtgacgatac tttccattac taatccataa catggctctt    1020
tgccacaact atctctattg gctatatgcc aatactctgt ccttcagaga ctgacacgga    1080
ctctgtattt ttacaggatg ggtcccatt tattatttac aaattcacat atacaacaac    1140
gccgtccccc gtgccgcag tttttattaa acatagcgtg gatctccac gcgaatctcg    1200 ggtacgtgtt ccggacatgg gctcttctcc ggtagcggcg gagcttccac atccgagccc    1260
tggtcccatg cctccagcgg ctcatggtcg ctcggcagct ccttgctcct aacagtggag    1320
gccagactta ggcacagcac aatgcccacc accaccagtg tgccgcacaa ggccgtggcg    1380
gtagggtatg tgtctgaaaa tgagctcgga gattgggctc gcaccgctga cgcagatgga    1440
agacttaagg cagcggcaga agaagatgca ggcagctgag ttgttgtatt ctgataagag    1500
tcagaggtaa ctcccgttgc ggtgctgtta acggtggagg gcagtgtagt ctgagcagta    1560
ctcgttgctg ccgcgcgcgc caccagacat aatagctgac agactaacag actgttcctt    1620
tccatgggtc tttctgcag tcaccgtcgt cgacgccacc atgcggctgt gcagagtgtg    1680
```

```
gctgtccgtg tgcctgtgtg ccgtggtgct gggccagtgc cagagagaga cagccgagaa    1740
gaacgactac taccgggtgc cccactactg ggatgcctgc agcagagccc tgcccgacca    1800
gacccggtac aaatacgtgg agcagctcgt ggacctgacc ctgaactacc actacgacgc    1860
cagccacggc ctggacaact tcgacgtgct gaagcggatc aacgtgaccg aggtgtccct    1920
gctgatcagc gacttccggc ggcagaacag aagaggcggc accaacaagc ggaccacctt    1980
caacgccgct ggctctctgg cccctcacgc cagatccctg gaattcagcg tgcggctgtt    2040
cgccaactga taatctagaa agccatggat atcggatcca ctacgcgtta gagctcgctg    2100
atcagcctcg actgtgcctt ctagttgcca gccatctgtt gtttgcccct cccccgtgcc    2160
ttccttgacc ctggaaggtg ccactcccac tgtccttttcc taataaaatg aggaaattgc    2220
atcgcattgt ctgagtaggt gtcattctat tctgggggt ggggtggggc aggacagcaa    2280
gggggaggat tgggaagaca atagcagggg ggtgggcgaa gaactccagc atgagatccc    2340
cgcgctggag gatcatccag ccggcgtccc ggaaaacgat tccgaagccc aacctttcat    2400
agaaggcggc ggtggaatcg aaatctcgtg atggcaggtt gggcgtcgct tggtcggtca    2460
tttcgaaccc cagagtcccg ctcagaagaa ctcgtcaaga aggcgataga aggcgatgcg    2520
ctgcgaatcg ggagcggcga taccgtaaag cacgaggaag cggtcagccc attcgccgcc    2580
aagctcttca gcaatatcac gggtagccaa cgctatgtcc tgatagcggt ccgccacacc    2640
cagccggcca cagtcgatga atccagaaaa gcggccattt tccaccatga tattcggcaa    2700
gcaggcatcg ccatgggtca cgacgagatc ctcgccgtcg gcatgcgcg ccttgagcct    2760 ggcgaacagt tcggctggcg cgagccctg atgctcttcg tccagatcat cctgatcgac    2820
aagaccggct tccatccgag tacgtgctcg ctcgatgcga tgtttcgctt ggtggtcgaa    2880
tgggcaggta gccggatcaa gcgtatgcag ccgccgcatt gcatcagcca tgatggatac    2940
tttctcggca ggagcaaggt gagatgacag gagatcctgc cccggcactt cgcccaatag    3000
cagccagtcc cttcccgctt cagtgacaac gtcgagcaca gctgcgcaag gaacgcccgt    3060
cgtggccagc cacgatagcc gcgctgcctc gtcctgcagt tcattcaggg caccggacag    3120
gtcggtcttg acaaaaagaa ccgggcgccc ctgcgctgac agccggaaca cggcggcatc    3180
agagcagccg attgtctgtt gtgcccagtc atagccgaat agcctctcca cccaagcggc    3240
cggagaacct gcgtgcaatc catcttgttc aatcatgcga aacgatcctc atcctgtctc    3300
ttgatcagat cttgatcccc tgcgccatca gatccttggc ggcaagaaag ccatccagtt    3360
tactttgcag ggcttcccaa ccttaccaga gggcgcccca gctggcaatt ccggttcgct    3420
tgctgtccat aaaaccgccc agtctagcta tcgccatgta agcccactgc aagctacctg    3480
ctttctcttt gcgcttgcgt tttcccttgt ccagatagcc cagtagctga cattcatccg    3540
gggtcagcac cgtttctgcg gactggcttt ctacgtgttc cgcttccttt agcagccctt    3600
gcgccctgag tgcttgcggc agcgtgaagc taattcatgg ttaaattttt gttaaatcag    3660
ctcatttttt aaccaatagg ccgaaatcgg caaaatccct tataaatcaa agaatagcc    3720 cgagataggg ttgagtgttg ttccagtttg gaacaagagt ccactattaa agaacgtgga    3780
ctccaacgtc aaagggcgaa aaaccgtcta tcagggcgat ggcccgatca gcttatgcgg    3840
tgtgaaatac cgcacagatg cgtaaggaga aaataccgca tcaggcgctc ttccgcttcc    3900
tcgctcactg actcgctgcg ctcggtcgtt cggctgcggc gagcggtatc agctcactca    3960
aaggcggtaa tacggttatc cacagaatca ggggataacg caggaaagaa catgtgagca    4020
aaaggccagc aaaaggccag gaaccgtaaa aaggccgcgt tgctggcgtt tttccatagg    4080
```

-continued

```
ctccgccccc ctgacgagca tcacaaaaat cgacgctcaa gtcagaggtg gcgaaacccg    4140
acaggactat aaagatacca ggcgtttccc cctggaagct ccctcgtgcg ctctcctgtt    4200
ccgaccctgc cgcttaccgg atacctgtcc gcctttctcc cttcgggaag cgtggcgctt    4260
tctcatagct cacgctgtag gtatctcagt tcggtgtagg tcgttcgctc caagctgggc    4320
tgtgtgcacg aaccccccgt tcagcccgac cgctgcgcct tatccggtaa ctatcgtctt    4380
gagtccaacc cggtaagaca cgacttatcg ccactggcag cagccactgg taacaggatt    4440
agcagagcga ggtatgtagg cggtgctaca gagttcttga agtggtggcc taactacggc    4500
tacactagaa ggacagtatt tggtatctgc gctctgctga agccagttac cttcggaaaa    4560
agagttggta gctcttgatc cggcaaacaa accaccgctg gtagcggtgg ttttttttgtt    4620 tgcaagcagc agattacgcg cagaaaaaaa ggatctcaag aagatccttt gatcttttct    4680
actgaacggt gatccccacc ggaattgcg                                      4709
```

<210> SEQ ID NO 29
<211> LENGTH: 692
<212> TYPE: PRT
<213> ORGANISM: Human cytomegalovirus

<400> SEQUENCE: 29

```
Arg Tyr Gly Ala Glu Ala Val Ser Glu Pro Leu Asp Lys Ala Phe His
  1               5                  10                  15

Leu Leu Leu Asn Thr Tyr Gly Arg Pro Ile Arg Phe Leu Arg Glu Asn
                 20                  25                  30

Thr Thr Gln Cys Thr Tyr Asn Ser Ser Leu Arg Asn Ser Thr Val Val
             35                  40                  45

Arg Glu Asn Ala Ile Ser Phe Asn Phe Phe Gln Ser Tyr Asn Gln Tyr
         50                  55                  60

Tyr Val Phe His Met Pro Arg Cys Leu Phe Ala Gly Pro Leu Ala Glu
     65                  70                  75                  80

Gln Phe Leu Asn Gln Val Asp Leu Thr Glu Thr Leu Glu Arg Tyr Gln
                 85                  90                  95

Gln Arg Leu Asn Thr Tyr Ala Leu Val Ser Lys Asp Leu Ala Ser Tyr
            100                 105                 110

Arg Ser Phe Ser Gln Gln Leu Lys Ala Gln Asp Ser Leu Gly Glu Gln
        115                 120                 125

Pro Thr Thr Val Pro Pro Ile Asp Leu Ser Ile Pro His Val Trp
    130                 135                 140

Met Pro Pro Gln Thr Thr Pro His Gly Trp Thr Glu Ser His Thr Thr
145                 150                 155                 160

Ser Gly Leu His Arg Pro His Phe Asn Gln Thr Cys Ile Leu Phe Asp
                165                 170                 175

Gly His Asp Leu Leu Phe Ser Thr Val Thr Pro Cys Leu His Gln Gly
            180                 185                 190

Phe Tyr Leu Ile Asp Glu Leu Arg Tyr Val Lys Ile Thr Leu Thr Glu
        195                 200                 205

Asp Phe Phe Val Val Thr Val Ser Ile Asp Asp Thr Pro Met Leu
    210                 215                 220

Leu Ile Phe Gly His Leu Pro Arg Val Leu Phe Lys Ala Pro Tyr Gln
225                 230                 235                 240

Arg Asp Asn Phe Ile Leu Arg Gln Thr Glu Lys His Glu Leu Leu Val
                245                 250                 255
```

```
Leu Val Lys Lys Asp Gln Leu Asn Arg His Ser Tyr Leu Lys Asp Pro
            260                 265                 270

Asp Phe Leu Asp Ala Ala Leu Asp Phe Asn Tyr Leu Asp Leu Ser Ala
            275                 280                 285

Leu Leu Arg Asn Ser Phe His Arg Tyr Ala Val Asp Val Leu Lys Ser
        290                 295                 300

Gly Arg Cys Gln Met Leu Asp Arg Arg Thr Val Glu Met Ala Phe Ala
305                 310                 315                 320

Tyr Ala Leu Ala Leu Phe Ala Ala Arg Gln Glu Glu Ala Gly Ala
                325                 330                 335

Gln Val Ser Val Pro Arg Ala Leu Asp Arg Gln Ala Ala Leu Leu Gln
            340                 345                 350

Ile Gln Glu Phe Met Ile Thr Cys Leu Ser Gln Thr Pro Pro Arg Thr
            355                 360                 365

Thr Leu Leu Leu Tyr Pro Thr Ala Val Asp Leu Ala Lys Arg Ala Leu
        370                 375                 380

Trp Thr Pro Asn Gln Ile Thr Asp Ile Thr Ser Leu Val Arg Leu Val
385                 390                 395                 400

Tyr Ile Leu Ser Lys Gln Asn Gln Gln His Leu Ile Pro Gln Trp Ala
                405                 410                 415

Leu Arg Gln Ile Ala Asp Phe Ala Leu Lys Leu His Lys Thr His Leu
            420                 425                 430

Ala Ser Phe Leu Ser Ala Phe Ala Arg Gln Glu Leu Tyr Leu Met Gly
            435                 440                 445

Ser Leu Val His Ser Met Leu Val His Thr Thr Glu Arg Arg Glu Ile
    450                 455                 460

Phe Ile Val Glu Thr Gly Leu Cys Ser Leu Ala Glu Leu Ser His Phe
465                 470                 475                 480

Thr Gln Leu Leu Ala His Pro His His Glu Tyr Leu Ser Asp Leu Tyr
                485                 490                 495

Thr Pro Cys Ser Ser Ser Gly Arg Arg Asp His Ser Leu Glu Arg Leu
            500                 505                 510

Thr Arg Leu Phe Pro Asp Ala Thr Val Pro Ala Thr Val Pro Ala Ala
        515                 520                 525

Leu Ser Ile Leu Ser Thr Met Gln Pro Ser Thr Leu Glu Thr Phe Pro
    530                 535                 540

Asp Leu Phe Cys Leu Pro Leu Gly Glu Ser Phe Ser Ala Leu Thr Val
545                 550                 555                 560

Ser Glu His Val Ser Tyr Ile Val Thr Asn Gln Tyr Leu Ile Lys Gly
                565                 570                 575

Ile Ser Tyr Pro Val Ser Thr Val Val Gly Gln Ser Leu Ile Ile
            580                 585                 590

Thr Gln Thr Asp Ser Gln Thr Lys Cys Glu Leu Thr Arg Asn Met His
        595                 600                 605

Thr Thr His Ser Ile Thr Val Ala Leu Asn Ile Ser Leu Glu Asn Cys
    610                 615                 620

Ala Phe Cys Gln Ser Ala Leu Leu Glu Tyr Asp Asp Thr Gln Gly Val
625                 630                 635                 640

Ile Asn Ile Met Tyr Met His Asp Ser Asp Val Leu Phe Ala Leu
                645                 650                 655

Asp Pro Tyr Asn Glu Val Val Ser Ser Pro Arg Thr His Tyr Leu
            660                 665                 670

Met Leu Leu Lys Asn Gly Thr Val Leu Glu Val Thr Asp Val Val Val
```

Asp Ala Thr Asp
    690

<210> SEQ ID NO 30
<211> LENGTH: 719
<212> TYPE: PRT
<213> ORGANISM: Human cytomegalovirus

<400> SEQUENCE: 30

Arg Tyr Gly Ala Glu Ala Val Ser Glu Pro Leu Asp Lys Ala Phe His
1               5                   10                  15

Leu Leu Leu Asn Thr Tyr Gly Arg Pro Ile Arg Phe Leu Arg Glu Asn
                20                  25                  30

Thr Thr Gln Cys Thr Tyr Asn Ser Ser Leu Arg Asn Ser Thr Val Val
            35                  40                  45

Arg Glu Asn Ala Ile Ser Phe Asn Phe Phe Gln Ser Tyr Asn Gln Tyr
        50                  55                  60

Tyr Val Phe His Met Pro Arg Cys Leu Phe Ala Gly Pro Leu Ala Glu
65                  70                  75                  80

Gln Phe Leu Asn Gln Val Asp Leu Thr Glu Thr Leu Glu Arg Tyr Gln
                85                  90                  95

Gln Arg Leu Asn Thr Tyr Ala Leu Val Ser Lys Asp Leu Ala Ser Tyr
            100                 105                 110

Arg Ser Phe Ser Gln Gln Leu Lys Ala Gln Asp Ser Leu Gly Glu Gln
        115                 120                 125

Pro Thr Thr Val Pro Pro Ile Asp Leu Ser Ile Pro His Val Trp
                130                 135                 140

Met Pro Pro Gln Thr Thr Pro His Gly Trp Thr Glu Ser His Thr Thr
145                 150                 155                 160

Ser Gly Leu His Arg Pro His Phe Asn Gln Thr Cys Ile Leu Phe Asp
                165                 170                 175

Gly His Asp Leu Leu Phe Ser Thr Val Thr Pro Cys Leu His Gln Gly
            180                 185                 190

Phe Tyr Leu Ile Asp Glu Leu Arg Tyr Val Lys Ile Thr Leu Thr Glu
        195                 200                 205

Asp Phe Phe Val Val Thr Val Ser Ile Asp Asp Thr Pro Met Leu
                210                 215                 220

Leu Ile Phe Gly His Leu Pro Arg Val Leu Phe Lys Ala Pro Tyr Gln
225                 230                 235                 240

Arg Asp Asn Phe Ile Leu Arg Gln Thr Glu Lys His Glu Leu Leu Val
                245                 250                 255

Leu Val Lys Lys Asp Gln Leu Asn Arg His Ser Tyr Leu Lys Asp Pro
            260                 265                 270

Asp Phe Leu Asp Ala Ala Leu Asp Phe Asn Tyr Leu Asp Leu Ser Ala
        275                 280                 285

Leu Leu Arg Asn Ser Phe His Arg Tyr Ala Val Asp Val Leu Lys Ser
                290                 295                 300

Gly Arg Cys Gln Met Leu Asp Arg Arg Thr Val Glu Met Ala Phe Ala
305                 310                 315                 320

Tyr Ala Leu Ala Leu Phe Ala Ala Ala Arg Gln Glu Glu Ala Gly Ala
                325                 330                 335

Gln Val Ser Val Pro Arg Ala Leu Asp Arg Gln Ala Ala Leu Leu Gln
            340                 345                 350

```
Ile Gln Glu Phe Met Ile Thr Cys Leu Ser Gln Thr Pro Arg Thr
            355                 360                 365

Thr Leu Leu Leu Tyr Pro Thr Ala Val Asp Leu Ala Lys Arg Ala Leu
    370                 375                 380

Trp Thr Pro Asn Gln Ile Thr Asp Ile Thr Ser Leu Val Arg Leu Val
385                 390                 395                 400

Tyr Ile Leu Ser Lys Gln Asn Gln Gln His Leu Ile Pro Gln Trp Ala
                405                 410                 415

Leu Arg Gln Ile Ala Asp Phe Ala Leu Lys Leu His Lys Thr His Leu
            420                 425                 430

Ala Ser Phe Leu Ser Ala Phe Ala Arg Gln Glu Leu Tyr Leu Met Gly
        435                 440                 445

Ser Leu Val His Ser Met Leu Val His Thr Thr Glu Arg Arg Glu Ile
    450                 455                 460

Phe Ile Val Glu Thr Gly Leu Cys Ser Leu Ala Glu Leu Ser His Phe
465                 470                 475                 480

Thr Gln Leu Leu Ala His Pro His His Glu Tyr Leu Ser Asp Leu Tyr
                485                 490                 495

Thr Pro Cys Ser Ser Gly Arg Arg Asp His Ser Leu Glu Arg Leu
            500                 505                 510

Thr Arg Leu Phe Pro Asp Ala Thr Val Pro Ala Thr Val Pro Ala Ala
    515                 520                 525

Leu Ser Ile Leu Ser Thr Met Gln Pro Ser Thr Leu Glu Thr Phe Pro
530                 535                 540

Asp Leu Phe Cys Leu Pro Leu Gly Glu Ser Phe Ser Ala Leu Thr Val
545                 550                 555                 560

Ser Glu His Val Ser Tyr Ile Val Thr Asn Gln Tyr Leu Ile Lys Gly
                565                 570                 575

Ile Ser Tyr Pro Val Ser Thr Thr Val Val Gly Gln Ser Leu Ile Ile
            580                 585                 590

Thr Gln Thr Asp Ser Gln Thr Lys Cys Glu Leu Thr Arg Asn Met His
        595                 600                 605

Thr Thr His Ser Ile Thr Val Ala Leu Asn Ile Ser Leu Glu Asn Cys
    610                 615                 620

Ala Phe Cys Gln Ser Ala Leu Leu Glu Tyr Asp Asp Thr Gln Gly Val
625                 630                 635                 640

Ile Asn Ile Met Tyr Met His Asp Ser Asp Val Leu Phe Ala Leu
                645                 650                 655

Asp Pro Tyr Asn Glu Val Val Val Ser Ser Pro Arg Thr His Tyr Leu
            660                 665                 670

Met Leu Leu Lys Asn Gly Thr Val Leu Glu Val Thr Asp Val Val Val
        675                 680                 685

Asp Ala Thr Asp Gly Thr Lys Leu Gly Pro Glu Gln Lys Leu Ile Ser
690                 695                 700

Glu Glu Asp Leu Asn Ser Ala Val Asp His His His His His
705                 710                 715

<210> SEQ ID NO 31
<211> LENGTH: 248
<212> TYPE: PRT
<213> ORGANISM: Human cytomegalovirus

<400> SEQUENCE: 31

Ala Ala Val Ser Val Ala Pro Thr Ala Ala Glu Lys Val Pro Ala Glu
1               5                   10                  15
```

Cys Pro Glu Leu Thr Arg Arg Cys Leu Leu Gly Val Phe Glu Gly
            20                  25                  30

Asp Lys Tyr Glu Ser Trp Leu Arg Pro Leu Val Asn Val Thr Gly Arg
        35                  40                  45

Asp Gly Pro Leu Ser Gln Leu Ile Arg Tyr Arg Pro Val Thr Pro Glu
50                  55                  60

Ala Ala Asn Ser Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
            100                 105                 110

Glu Cys Gly Asp Gly Ser Pro Ala Val Tyr Thr Cys Val Asp Asp Leu
        115                 120                 125

Cys Arg Gly Tyr Asp Leu Thr Arg Leu Ser Tyr Gly Arg Ser Ile Phe
130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Tyr Ala Gly Leu Pro
210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 32
<211> LENGTH: 442
<212> TYPE: PRT
<213> ORGANISM: Human cytomegalovirus

<400> SEQUENCE: 32

Cys Asn Val Leu Val Asn Ser Arg Gly Thr Arg Arg Ser Trp Pro Tyr
1               5                   10                  15

Thr Val Leu Ser Tyr Arg Gly Lys Glu Ile Leu Lys Lys Gln Lys Glu
            20                  25                  30

Asp Ile Leu Lys Arg Leu Met Ser Thr Ser Asp Gly Tyr Arg Phe
        35                  40                  45

Leu Met Tyr Pro Ser Gln Gln Lys Phe His Ala Ile Val Ile Ser Met
50                  55                  60

Asp Lys Phe Pro Gln Asp Tyr Ile Leu Ala Gly Pro Ile Arg Asn Asp
65                  70                  75                  80

Ser Ile Thr His Met Trp Phe Asp Phe Tyr Ser Thr Gln Leu Arg Lys
                85                  90                  95

Pro Ala Lys Tyr Val Tyr Ser Glu Tyr Asn His Thr Ala His Lys Ile
            100                 105                 110

Thr Leu Arg Pro Pro Pro Cys Gly Thr Val Pro Ser Met Asn Cys Leu
        115                 120                 125

Ser Glu Met Leu Asn Val Ser Lys Arg Asn Asp Thr Gly Glu Lys Gly

```
            130                 135                 140
Cys Gly Asn Phe Thr Thr Phe Asn Pro Met Phe Phe Asn Val Pro Arg
145                 150                 155                 160

Trp Asn Thr Lys Leu Tyr Ile Gly Ser Asn Lys Val Asn Val Asp Ser
                165                 170                 175

Gln Thr Ile Tyr Phe Leu Gly Leu Thr Ala Leu Leu Leu Arg Tyr Ala
                180                 185                 190

Gln Arg Asn Cys Thr Arg Ser Phe Tyr Leu Val Asn Ala Met Ser Arg
                195                 200                 205

Asn Leu Phe Arg Val Pro Lys Tyr Ile Asn Gly Thr Lys Leu Lys Asn
            210                 215                 220

Thr Met Arg Lys Leu Lys Arg Lys Gln Ala Leu Val Lys Glu Gln Pro
225                 230                 235                 240

Gln Lys Lys Asn Lys Lys Ser Gln Ser Thr Thr Thr Pro Tyr Leu Ser
                245                 250                 255

Tyr Thr Thr Ser Thr Ala Phe Asn Val Thr Thr Asn Val Thr Tyr Ser
                260                 265                 270

Ala Thr Ala Ala Val Thr Arg Val Ala Thr Ser Thr Thr Gly Tyr Arg
            275                 280                 285

Pro Asp Ser Asn Phe Met Lys Ser Ile Met Ala Thr Gln Leu Arg Asp
290                 295                 300

Leu Ala Thr Trp Val Tyr Thr Thr Leu Arg Tyr Arg Asn Glu Pro Phe
305                 310                 315                 320

Cys Lys Pro Asp Arg Asn Arg Thr Ala Val Ser Glu Phe Met Lys Asn
                325                 330                 335

Thr His Val Leu Ile Arg Asn Glu Thr Pro Tyr Thr Ile Tyr Gly Thr
                340                 345                 350

Leu Asp Met Ser Ser Leu Tyr Tyr Asn Glu Thr Met Ser Val Glu Asn
                355                 360                 365

Glu Thr Ala Ser Asp Asn Asn Glu Thr Thr Pro Thr Ser Pro Ser Thr
            370                 375                 380

Arg Phe Gln Arg Thr Phe Ile Asp Pro Leu Trp Asp Tyr Leu Asp Ser
385                 390                 395                 400

Leu Leu Phe Leu Asp Lys Ile Arg Asn Phe Ser Leu Gln Leu Pro Ala
                405                 410                 415

Tyr Gly Asn Leu Thr Pro Pro Glu His Arg Arg Ala Ala Asn Leu Ser
                420                 425                 430

Thr Leu Asn Ser Leu Trp Trp Trp Ser Gln
            435                 440

<210> SEQ ID NO 33
<211> LENGTH: 144
<212> TYPE: PRT
<213> ORGANISM: Human cytomegalovirus

<400> SEQUENCE: 33

Glu Glu Cys Cys Glu Phe Ile Asn Val Asn His Pro Pro Glu Arg Cys
1               5                   10                  15

Tyr Asp Phe Lys Met Cys Asn Arg Phe Thr Val Ala Leu Arg Cys Pro
                20                  25                  30

Asp Gly Glu Val Cys Tyr Ser Pro Glu Lys Thr Ala Glu Ile Arg Gly
            35                  40                  45

Ile Val Thr Thr Met Thr His Ser Leu Thr Arg Gln Val Val His Asn
        50                  55                  60
```

```
Lys Leu Thr Ser Cys Asn Tyr Asn Pro Leu Tyr Leu Glu Ala Asp Gly
 65                  70                  75                  80

Arg Ile Arg Cys Gly Lys Val Asn Asp Lys Ala Gln Tyr Leu Leu Gly
                 85                  90                  95

Ala Ala Gly Ser Val Pro Tyr Arg Trp Ile Asn Leu Glu Tyr Asp Lys
            100                 105                 110

Ile Thr Arg Ile Val Gly Leu Asp Gln Tyr Leu Glu Ser Val Lys Lys
        115                 120                 125

His Lys Arg Leu Asp Val Cys Arg Ala Lys Met Gly Tyr Met Leu Gln
    130                 135                 140
```

<210> SEQ ID NO 34
<211> LENGTH: 189
<212> TYPE: PRT
<213> ORGANISM: Human cytomegalovirus

<400> SEQUENCE: 34

```
Ser Pro Trp Ser Thr Leu Thr Ala Asn Gln Asn Pro Ser Pro Pro Trp
 1               5                  10                  15

Ser Lys Leu Thr Tyr Ser Lys Pro His Asp Ala Ala Thr Phe Tyr Cys
            20                  25                  30

Pro Phe Leu Tyr Pro Ser Pro Arg Ser Pro Leu Gln Phe Ser Gly
         35                  40                  45

Phe Gln Arg Val Ser Thr Gly Pro Glu Cys Arg Asn Glu Thr Leu Tyr
 50                  55                  60

Leu Leu Tyr Asn Arg Glu Gly Gln Thr Leu Val Glu Arg Ser Ser Thr
 65                  70                  75                  80

Trp Val Lys Lys Val Ile Trp Tyr Leu Ser Gly Arg Asn Gln Thr Ile
                 85                  90                  95

Leu Gln Arg Met Pro Arg Thr Ala Ser Lys Pro Ser Asp Gly Asn Val
            100                 105                 110

Gln Ile Ser Val Glu Asp Ala Lys Ile Phe Gly Ala His Met Val Pro
        115                 120                 125

Lys Gln Thr Lys Leu Leu Arg Phe Val Val Asn Asp Gly Thr Arg Tyr
    130                 135                 140

Gln Met Cys Val Met Lys Leu Glu Ser Trp Ala His Val Phe Arg Asp
145                 150                 155                 160

Tyr Ser Val Ser Phe Gln Val Arg Leu Thr Phe Thr Glu Ala Asn Asn
                165                 170                 175

Gln Thr Tyr Thr Phe Cys Thr His Pro Asn Leu Ile Val
            180                 185
```

<210> SEQ ID NO 35
<211> LENGTH: 111
<212> TYPE: PRT
<213> ORGANISM: Human cytomegalovirus

<400> SEQUENCE: 35

```
Gln Cys Gln Arg Glu Thr Ala Glu Lys Asn Asp Tyr Tyr Arg Val Pro
 1               5                  10                  15

His Tyr Trp Asp Ala Cys Ser Arg Ala Leu Pro Asp Gln Thr Arg Tyr
            20                  25                  30

Lys Tyr Val Glu Gln Leu Val Asp Leu Thr Leu Asn Tyr His Tyr Asp
        35                  40                  45

Ala Ser His Gly Leu Asp Asn Phe Asp Val Leu Lys Arg Ile Asn Val
    50                  55                  60
```

-continued

Thr Glu Val Ser Leu Leu Ile Ser Asp Phe Arg Gln Asn Arg Arg
65                  70                  75                  80

Gly Gly Thr Asn Lys Arg Thr Thr Phe Asn Ala Ala Gly Ser Leu Ala
                85                  90                  95

Pro His Ala Arg Ser Leu Glu Phe Ser Val Arg Leu Phe Ala Asn
            100                 105                 110

<210> SEQ ID NO 36
<211> LENGTH: 884
<212> TYPE: PRT
<213> ORGANISM: Human cytomegalovirus

<400> SEQUENCE: 36

Val Ser Ser Ser Thr Arg Gly Thr Ser Ala Thr His Ser His His
1               5                   10                  15

Ser Ser His Thr Thr Ser Ala Ala His Ser Arg Ser Gly Ser Val Ser
                20                  25                  30

Gln Arg Val Thr Ser Ser Gln Thr Val Ser His Gly Val Asn Glu Thr
            35                  40                  45

Ile Tyr Asn Thr Thr Leu Lys Tyr Gly Asp Val Val Gly Val Asn Thr
50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Val Cys Thr Ser Met Lys Pro Ile Asn
                85                  90                  95

Glu Asp Leu Asp Glu Gly Ile Met Val Val Tyr Lys Arg Asn Ile Val
            100                 105                 110

Ala His Thr Phe Lys Val Arg Val Tyr Gln Lys Val Leu Thr Phe Arg
        115                 120                 125

Arg Ser Tyr Ala Tyr Ile His Thr Thr Tyr Leu Leu Gly Ser Asn Thr
    130                 135                 140

Glu Tyr Val Ala Pro Pro Met Trp Glu Ile His His Ile Asn Ser His
145                 150                 155                 160

Ser Gln Cys Tyr Ser Ser Tyr Ser Arg Val Ile Ala Gly Thr Val Phe
                165                 170                 175

Val Ala Tyr His Arg Asp Ser Tyr Glu Asn Lys Thr Met Gln Leu Met
            180                 185                 190

Pro Asp Asp Tyr Ser Asn Thr His Ser Thr Arg Tyr Val Thr Val Lys
        195                 200                 205

Asp Gln Trp His Ser Arg Gly Ser Thr Trp Leu Tyr Arg Glu Thr Cys
    210                 215                 220

Asn Leu Asn Cys Met Val Thr Ile Thr Thr Ala Arg Ser Lys Tyr Pro
225                 230                 235                 240

Tyr His Phe Phe Ala Thr Ser Thr Gly Asp Val Val Asp Ile Ser Pro
                245                 250                 255

Phe Tyr Asn Gly Thr Asn Arg Asn Ala Ser Tyr Phe Gly Glu Asn Ala
            260                 265                 270

Asp Lys Phe Phe Ile Phe Pro Asn Tyr Thr Ile Val Ser Asp Phe Gly
        275                 280                 285

Arg Pro Asn Ser Ala Leu Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

```
Glu Ala Glu Asp Ser Tyr His Phe Ser Ser Ala Lys Met Thr Ala Thr
                340                 345                 350

Phe Leu Ser Lys Lys Gln Glu Val Asn Met Ser Asp Ser Ala Leu Asp
                355                 360                 365

Cys Val Arg Asp Glu Ala Ile Asn Lys Leu Gln Gln Ile Phe Asn Thr
                370                 375                 380

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
                405                 410                 415

Leu Val Glu Leu Glu Arg Leu Ala Asn Arg Ser Ser Leu Asn Leu Thr
                420                 425                 430

His Asn Arg Thr Lys Arg Ser Thr Asp Gly Asn Asn Ala Thr His Leu
                435                 440                 445

Ser Asn Met Glu Ser Val His Asn Leu Val Tyr Ala Gln Leu Gln Phe
                450                 455                 460

Thr Tyr Asp Thr Leu Arg Gly Tyr Ile Asn Arg Ala Leu Ala Gln Ile
465                 470                 475                 480

Ala Glu Ala Trp Cys Val Asp Gln Arg Arg Thr Leu Glu Val Phe Lys
                485                 490                 495

Glu Leu Ser Lys Ile Asn Pro Ser Ala Ile Leu Ser Ala Ile Tyr Asn
                500                 505                 510

Lys Pro Ile Ala Ala Arg Phe Met Gly Asp Val Leu Gly Leu Ala Ser
                515                 520                 525

Cys Val Thr Ile Asn Gln Thr Ser Val Lys Val Leu Arg Asp Met Asn
                530                 535                 540

Val Lys Glu Ser Pro Gly Arg Cys Tyr Ser Arg Pro Val Val Ile Phe
545                 550                 555                 560

Asn Phe Ala Asn Ser Ser Tyr Val Gln Tyr Gly Gln Leu Gly Glu Asp
                565                 570                 575

Asn Glu Ile Leu Leu Gly Asn His Arg Thr Glu Glu Cys Gln Leu Pro
                580                 585                 590

Ser Leu Lys Ile Phe Ile Ala Gly Asn Ser Ala Tyr Glu Tyr Val Asp
                595                 600                 605

Tyr Leu Phe Lys Arg Met Ile Asp Leu Ser Ser Ile Ser Thr Val Asp
                610                 615                 620

Ser Met Ile Ala Leu Asp Ile Asp Pro Leu Glu Asn Thr Asp Phe Arg
625                 630                 635                 640

Val Leu Glu Leu Tyr Ser Gln Lys Glu Leu Arg Ser Ser Asn Val Phe
                645                 650                 655

Asp Leu Glu Glu Ile Met Arg Glu Phe Asn Ser Tyr Lys Gln Arg Val
                660                 665                 670

Lys Tyr Val Glu Asp Lys Val Val Asp Pro Leu Pro Pro Tyr Leu Lys
                675                 680                 685

Gly Leu Asp Asp Leu Met Ser Gly Leu Gly Ala Ala Gly Lys Ala Val
                690                 695                 700

Gly Val Ala Ile Gly Ala Val Gly Gly Ala Val Ala Ser Val Val Glu
705                 710                 715                 720

Gly Val Ala Thr Phe Leu Lys Asn Pro Phe Gly Ala Phe Thr Ile Ile
                725                 730                 735

Leu Val Ala Ile Ala Val Val Ile Ile Thr Tyr Leu Ile Tyr Thr Arg
                740                 745                 750
```

-continued

| | | | | | | | | | | | | | | |
|---|---|---|---|---|---|---|---|---|---|---|---|---|---|---|
|Gln|Arg|Arg 755|Leu|Cys|Thr|Gln|Pro 760|Leu|Gln|Asn|Leu|Phe 765|Pro|Tyr|Leu|
|Val|Ser 770|Ala|Asp|Gly|Thr|Thr 775|Val|Thr|Ser|Gly|Ser 780|Thr|Lys|Asp|Thr|
|Ser 785|Leu|Gln|Ala|Pro|Pro 790|Ser|Tyr|Glu|Glu|Ser 795|Val|Tyr|Asn|Ser|Gly 800|
|Arg|Lys|Gly|Pro|Gly 805|Pro|Pro|Ser|Ser|Asp 810|Ala|Ser|Thr|Ala 815|Ala|Pro|
|Pro|Tyr|Thr|Asn 820|Glu|Gln|Ala|Tyr|Gln 825|Met|Leu|Leu|Ala|Leu 830|Ala|Arg|
|Leu|Asp|Ala 835|Glu|Gln|Arg|Ala|Gln 840|Gln|Asn|Gly|Thr|Asp 845|Ser|Leu|Asp|
|Gly|Arg 850|Thr|Gly|Thr|Gln|Asp 855|Lys|Gly|Gln|Lys|Pro 860|Asn|Leu|Leu|Asp|
|Arg 865|Leu|Arg|His|Arg|Lys 870|Asn|Gly|Tyr|Arg|His 875|Leu|Lys|Asp|Ser|Asp 880|
|Glu|Glu|Glu|Asn| | | | | | | | | | | | |

COMPLEXES OF CYTOMEGALOVIRUS PROTEINS

RELATED APPLICATIONS

This application is the U.S. National Phase of International Application No. PCT/EP2013/063750, entitled "COMPLEXES OF CYTOMEGALOVIRUS PROTEINS," filed Jun. 29, 2013 and published in English, which claims the benefit of U.S. Provisional Application No. 61/668,975, filed Jul. 6, 2012 and U.S. Provisional Application No. 61/770,257 filed Feb. 27, 2013, the complete contents of each of the foregoing applications are hereby incorporated herein by reference for all purposes.

SEQUENCE LISTING

The instant application contains a Sequence Listing which was submitted in ASCII format in PCT application PCT/EP2013/063750 and is hereby incorporated by reference in its entirety. Said ASCII copy, created on Jun. 27, 2013, is named SEQUENCE LISTING_PAT054805.txt and is 152,654 bytes in size.

TECHNICAL FIELD

This invention is in the field of vaccination against human cytomegalovirus (HCMV), and in particular the isolation of purified complexes comprising gH, gL and at least one more HCMV glycoprotein, preferably the trimeric gH/gL/gO complex or the pentameric gH/gL/pUL128/pUL130/pUL131A complex, and their subsequent use in vaccines.s

BACKGROUND ART

Cytomegalovirus (CMV) is a genus of virus that belongs to the viral family known as Herpesviridae or herpesviruses. The species that infects humans is commonly known as HCMV or human herpesvirus-5 (HHV-5). Within Herpesviridae, HCMV belongs to the Betaherpesvirinae subfamily, which also includes cytomegaloviruses from other mammals.

Although they may be found throughout the body, HCMV infections are frequently associated with the salivary glands. HCMV infects between 50% and 80% of adults in the United States (40% worldwide), as indicated by the presence of antibodies in much of the general population. HCMV infection is typically unnoticed in healthy people, but can be life-threatening for the immunocompromised, such as HIV-infected persons, organ transplant recipients, or new born infants (Mocarski, Shenk and Pass 2006). HCMV is the virus most frequently transmitted to a developing fetus. After infection, HCMV has an ability to remain latent within the body for the lifetime of the host, with occasional reactivations from latency.

HCMV seems to have a large impact on immune parameters in later life and may contribute to increased morbidity and eventual mortality (Simanek, et al. (2011)).

To date, the genomes of over 20 different HCMV strains have been sequenced, including those of both laboratory strains and clinical isolates. For example, the following strains of HCMV have been sequenced: Towne (GI: 239909366), AD169 (GI:219879600), Toledo (GI: 290564358) and Merlin (GI: 155573956). HCMV strains AD169, Towne and Merlin can be obtained from the American Type Culture Collection (ATCC VR538, ATCC VR977 and ATCC VR1590, respectively).

HCMV contains an unknown number of membrane protein complexes. Of the approximately 30 known glycoproteins in the viral envelope, gH and gL have emerged as particularly interesting due to their presence in several different complexes: dimeric gH/gL, trimeric gH/gL/gO (also known as the gCIII complex) and the pentameric gH/gL/pUL128/pUL130/pUL131A (the latter protein is also referred to as pUL131). HCMV is thought to use the pentameric complexes to enter epithelial and endothelial cells by endocytosis and low-pH-dependent fusion but it is thought to enter fibroblasts by direct fusion at the plasma membrane in a process involving gH/gL or possibly gH/gL/gO. The gH/gL and/or gH/gL/gO complex(es) is/are sufficient for fibroblast infection, whereas the pentameric complex is required to infect endothelial and epithelial cells (Ryckman, Rainish, et al. 2008).

Genini et al. (2011) discloses a serum antibody response to the pentameric complex of HCMV in primary and reactivated HCMV infections. The response was determined by both indirect immunofluorescence (IFA) and ELISA, using fixed or lysed epithelial (ARPE-19) cells infected with one or more adenoviral vectors, each carrying one HCMV gene and, in parallel, with a control adenovirus vector. The specificity of results was determined by the reactivity of human neutralizing monoclonal antibodies recognizing two, three, or four proteins of the complex. In 14 cases of primary infection, an IgG antibody seroconversion to the UL128-131 gene products was consistently detected within 2-4 weeks after onset of infection, while antibodies persisted for at least 12 months. The IgG antibody response to UL128-131 gene products was generally superior to the response to gH and appeared to follow the neutralizing antibody response (as determined in epithelial cells). In reactivated infections, the antibody response showed a trend reminiscent of a booster response. IgG antibodies were detected in HCMV-seropositive healthy adult controls, but not in HCMV-seronegative individuals.

Kinzler et al. (2002) co-expressed gH, gL, and gO in insect cells using a recombinant baculovirus, but were unable to produce the gH/gL/gO tripartite complex. Instead, only gH/gL heterodimers, gH/gL heteromultimers, and gO homomultimers were detected. In contrast, co-expression of gH, gL, and gO in mammalian cells produced high molecular weight complexes that closely resemble gH/gL/gO complexes formed in HCMV infected cells. Cell surface immunofluorescence showed that these complexes are expressed and displayed on the surface of transfected cells.

U.S. Pat. No. 7,704,510 discloses that pUL131A is required for epithelial cell tropism. U.S. Pat. No. 7,704,510 also discloses that pUL128 and pUL130 form a complex with gH/gL, which is incorporated into virions. This complex is required to infect endothelial and epithelial cells but not fibroblasts. Anti-CD46 antibodies were found to inhibit HCMV infection of epithelial cells. However, U.S. Pat. No. 7,704,510 does not disclose isolation of HCMV complexes.

To date, researchers have been unable to purify complexes comprising HCMV gH, gL and at least one more HCMV glycoprotein, such as the trimeric gH/gL/gO complex or the pentameric gH/gL/pUL128/pUL130/pUL131A complex. Such purified complexes would be useful as antigens for diagnostic application and as immunogens for vaccines against HCMV.

DISCLOSURE OF THE INVENTION

The invention is based on the recombinant expression and purification of HCMV membrane protein complexes, wherein said complexes comprise gH, gL and at least one more HCMV glycoprotein.

The invention provides a process for producing an HCMV membrane protein complex comprising gH, gL and at least one more HCMV glycoprotein, wherein said process comprises the recombinant co-expression of an HCMV gH protein, an HCMV gL protein, and at least one more HCMV glycoprotein, under conditions in which said gH, gL and at least one more HCMV glycoprotein assemble to form a protein complex. This process may optionally involve isolation of the protein complex, so that it can be prepared in purified form. In some embodiments, the process does not involve co-expression of any non-envelope HCMV proteins, such as the tegument or capsid proteins.

The invention also provides a protein complex produced by this process. For instance, the complex can comprise (i) gH, gL and gO or (ii) gH, gL, pUL128, pUL130 and pUL131A.

In some embodiments, the complexes of the invention can be produced at high yields. For example, in processes involving growing cells of the invention in growth medium, the membrane protein complex of the invention may accumulate to a level of more than 0.4 mg per liter of growth medium (e.g. 0.45, 0.5, 0.55, 0.6, 0.65, 0.7, 0.75, 0.8, 0.85, 0.9, 0.95, 1.0, 1.2, 1.4, 1.6, 1.8, 2, 2.5, 3, 3.5, 4, 4.5 or 5 mg per liter of growth medium or more).

The invention also provides an isolated protein complex comprising an HCMV gH, an HCMV gL and at least one more HCMV glycoprotein. One example of a protein complex that comprises gH and gL is the trimeric complex consisting of gH, gL and gO. Another example of a protein complex that comprises gH and gL is the pentameric complex consisting of gH, gL, pUL128, pUL130 and pUL131A.

The invention also provides a composition comprising a protein complex of the invention. In some embodiments, the composition does not contain polyacrylamide. In some embodiments, the composition is a liquid e.g. an aqueous liquid, not a gel. In some embodiments, the protein complex is not immobilised within the composition. For example, said HCMV membrane protein complex may not be present in a gel, or on a film, membrane, paper or slide.

The invention also provides a composition comprising a protein complex of the invention, wherein said composition does not contain any non-envelope HCMV proteins, such as the HCMV tegument or HCMV capsid proteins.

The invention also provides a modified HCMV gH polypeptide, wherein said polypeptide lacks a transmembrane (TM) domain. The absence of a TM domain means that this modified polypeptide cannot reside within a lipid bilayer. In some embodiments, the gH polypeptide lacks the full-length natural TM domain; in other embodiments, it can retain a portion of the natural TM domain, but not enough to let the protein reside in a lipid bilayer. Thus the polypeptide can contain up to 10 amino acids (e.g. 1, 2, 3, 4, 5, 6, 7, 8, 9 or 10 amino acids) of the natural gH TM domain. In addition to lacking some or all of the TM domain, the polypeptide may also lack the natural C-terminal domain of HCMV gH or may lack a portion of the C-terminal domain. The invention also provides nucleic acid molecules encoding said modified gH polypeptide, and processes for producing said modified gH polypeptide e.g. by recombinant expression, or by chemical synthesis (at least in part).

The invention provides a method of transfection involving the introduction of one or more nucleic acid molecules which encode the protein components of said HCMV membrane protein complex into cells. Said one or more nucleic acid molecules may be stably introduced into the cells (e.g. by chromosomal integration) or may be transiently introduced into the cells. The invention also provides a cell which is derived from said transfection. Preferably, a cell which is derived from said transfection is a cell in which said one or more nucleic acid molecules have been stably introduced. The invention also provides progeny of said cell, a clone of said cell or a cell which has been passaged from said cell. These cells can be cultured to express complexes of the invention, which may then be purified.

The invention also provides a cell that produces an HCMV membrane protein complex, wherein the cell does not (i) contain an HCMV genome, and/or (ii) produce HCMV virions, and/or (iii) express any non-envelope HCMV proteins. Ideally the cell lacks one of (i), (ii) or (iii); preferably, it lacks two; more preferably, it lacks all three of (i), (ii) and (iii).

The invention provides antibodies which recognise an isolated HCMV membrane protein complex of the invention, but do not bind to any of isolated gH, gL, gO, pUL128, pUL130 or pUL131A polypeptides and/or do not bind to isolated gH-gL heterodimers. The antibodies of the invention may have been raised using an isolated HCMV membrane protein complex of the invention as an antigen. Preferably, the antibodies of the invention are neutralizing antibodies. The antibodies of the invention may have been identified using in vitro selection methods, such as phage display using diverse antibody libraries. As described below, antibodies of the invention may be human or humanised antibodies and/or they may be monoclonal or polyclonal antibodies.

The invention also provides a method for raising antibodies using an isolated HCMV membrane protein complex of the invention. Alternatively, isolated HCMV membrane protein complex of the invention may be used to identify antibodies using in vitro selection methods, such as phage display using diverse antibody libraries.

The antibodies of the invention may be used in a diagnostic assay and may be labelled directly or indirectly. In some embodiments, the antibodies of the invention may be used in therapy, for example in the treatment of HCMV infection.

Proteins of the Invention

HCMV glycoprotein H (gH), which is encoded by the UL75 gene, is a virion glycoprotein that is essential for infectivity and which is conserved among members of the alpha-, beta- and gammaherpesviruses. It forms a stable complex with gL, and the formation of this complex facilitates the cell surface expression of gH. Based on the crystal structures of HSV-2 and EBV gH/gL complexes, the gL subunit and N-terminal residues of gH form a globular domain at one end of the structure (the 'head'), which is implicated in interactions with gB and activation of membrane fusion. The C-terminal domain of gH, proximal to the viral membrane (the 'tail'), is also implicated in membrane fusion. gH displays determinants that are recognized by the host factor TLR2, and it directly interacts with a heterodimer formed between the host factors TLR2 and TLR1. TLR2 mediates NF-κB activation and inflammatory cytokine responses from cells (Boehme, Guerrero and Compton 2006).

The gH from HCMV strain Merlin has been reported (GI:52139248, SEQ ID NO: 1) to consist of 742 amino acids. The gH from HCMV strain Towne (GI:138314, SEQ ID NO: 2) also consists of 742 amino acids, and has been reported to have six N-glycosylation sites (at residues 55, 62, 67, 192, 641 and 700), and consist of a hydrophobic signal sequence at its N-terminus (amino acid residues 1-23), an ectodomain (residues 24-717) that projects out of the cell into the extracellular space, a hydrophobic TM domain (residues 718-736) and a C-terminal cytoplasmic domain (residues 737-742). SEQ ID NO: 2 shares 99% and 96% amino acid similarity to SEQ ID NO: 1 and the gH from HCMV strain AD169 (GI:138313, SEQ ID NO: 3), respectively.

Typically, the N-terminal signal sequence of gH proteins is cleaved by a host cell signal peptidase to produce mature gH proteins. The gH proteins in HCMV membrane complexes of the invention may lack an N-terminal signal sequences. Preferably, mature forms of gH (as found in isolated HCMV membrane complexes of the invention) lack the N-terminal signal sequence, the TM domain and the C-terminal domain.

Expression of the full-length UL75 gene sequence hinders purification of soluble complexes comprising gH. Rather, complexes comprising gH can be purified at high yield and purity by omitting at least a portion of the TM domain of gH. For example, constructs encoding just the N-terminal signal sequence and the ectodomain of gH (but not the TM domain) can be used to express a form of gH which is easily purified. Said constructs may encode the majority (e.g. 70%, 80%, 85%, 90%, 95%, 96%, 97%, 98%, 99%, 99.5% or more) of the ectodomain of gH, but none or only a small portion of the TM domain. gH proteins of the invention may include the whole of the gH ectodomain or a truncated form of the gH ectodomain. Said truncated forms of the ectodomain may lack between 1 and 20 amino acids (e.g. 1, 2, 3, 4, 5, 6, 7, 8, 9, 10, 11, 12, 13, 14, 15, 16, 17, 18, 19 or 20 amino acid residues) at their N-termini and/or C-termini relative to a full-length HCMV gH protein. An example of a gH protein of the invention is SEQ ID NO: 4, which consists of amino acid residues 1-715 of SEQ ID NO: 1. An example of a preferred gH protein of the invention is SEQ ID NO: 29, which lacks the N-terminal signal sequence, TM domain and C-terminal domain of gH and consists of amino acid residues 24-715 of SEQ ID NO: 1.

gH proteins of the invention may contain additional amino acid residues, such as N-terminal or C-terminal extensions. Such extensions may include one or more tags, which can facilitate detection (e.g. an epitope tag for detection by monoclonal antibodies) and/or purification (e.g. a polyhistidine-tag to allow purification on a nickel-chelating resin) of the gH protein. An example of a C-terminal extension which includes a myc-tag and a polyhistidine-tag is given as SEQ ID NO: 5. Thus, gH proteins of the invention (e.g. SEQ ID NOs: 6 and 30) may include at their C-termini an amino acid sequence which is at least 60%, 70%, 80%, 85%, 90%, 91%, 92%, 93%, 94%, 95%, 96%, 97%, 98% or 99% identical to the sequence recited in SEQ ID NO: 5. gH proteins of the invention may comprise a truncated gH ectodomain fused to a C-terminal extension.

The ectodomain of gH corresponds to the portion of gH which lacks the hydrophobic TM. The location and length of the ectodomain can be predicted based on pairwise alignment of a given sequence to SEQ ID NO: 1, for example by aligning the amino acid sequence of a gH polypeptide of interest to SEQ ID NO: 1 and identifying the sequence that aligns to residues 24-717 of SEQ ID NO: 1. Similarly, the locations of the TM and C-terminal domains can be predicted by aligning the amino acid sequence of a gH polypeptide of interest to SEQ ID NO: 1 and identifying the sequences that align to residues 718-736 and 737-742 of SEQ ID NO: 1, respectively. Alternatively, the location and length of the ectodomain, the signal sequence and the TM domain can be predicted based on computational analysis of the hydrophobicity along the length of a given gH protein sequence. The signal sequence and the TM domain have the highest levels of hydrophobicity and these two regions flank the ectodomain, which is less hydrophobic.

gH proteins of the invention can have various degrees of identity to SEQ ID NO: 4 such as at least 60%, 70%, 80%, 85%, 90%, 91%, 92%, 93%, 94%, 95%, 96%, 97%, 98% or 99% identical to the sequence recited in SEQ ID NO: 4. gH proteins of the invention can have various degrees of identity to SEQ ID NO: 6 such as at least 60%, 70%, 80%, 85%, 90%, 91%, 92%, 93%, 94%, 95%, 96%, 97%, 98% or 99% identical to the sequence recited in SEQ ID NO: 6. gH proteins of the invention can have various degrees of identity to SEQ ID NO: 29 such as at least 60%, 70%, 80%, 85%, 90%, 91%, 92%, 93%, 94%, 95%, 96%, 97%, 98% or 99% identical to the sequence recited in SEQ ID NO: 29. gH proteins of the invention can have various degrees of identity to SEQ ID NO: 30 such as at least 60%, 70%, 80%, 85%, 90%, 91%, 92%, 93%, 94%, 95%, 96%, 97%, 98% or 99% identical to the sequence recited in SEQ ID NO: 30. Preferred gH proteins: (i) can dimerise with HCMV gL; (ii) form part of the trimeric gH/gL/gO complex; (iii) form part of the pentameric gH/gL/pUL128/pUL130/pUL131A complex; (iv) comprise at least one epitope from SEQ ID NO: 4 or SEQ ID NO: 29; and/or (v) can elicit antibodies in vivo which immunologically cross-react with an HCMV virion.

HCMV glycoprotein L (gL) is encoded by the UL115 gene. gL is thought to be essential for viral replication and all known functional properties of gL are directly associated with its dimerization with gH. The gL/gH complex is required for the fusion of viral and plasma membranes leading to virus entry into the host cell. gL from HCMV strain Merlin (GI:39842115, SEQ ID NO: 7) and HCMV strain Towne (GI:239909463, SEQ ID NO: 8) have been reported to be 278 amino acids in length. gL from HCMV strain AD169 (GI:2506510, SEQ ID NO: 9) has been reported to be 278 amino acids in length, include a signal sequence at its N-terminus (amino acid residues 1-35), have two N-glycosylation sites (at residues 74 and 114) and lack a TM domain (Rigoutsos, et al. 2003). The N-terminal signal sequence in SEQ ID NO: 7 is predicted to comprise amino acid residues 1-30. SEQ ID NO: 8 shares 98% amino acid identity with SEQ ID NO: 7. Sequencing of the full-length gL gene from 22 to 39 clinical isolates, as well as laboratory strains AD169, Towne and Toledo revealed less than 2% variation in the amino acid sequences among the isolates (Rasmussen, et al. 2002).

Typically, the N-terminal signal sequence of gL proteins is cleaved by a host cell signal peptidase to produce mature gL proteins. The gL proteins in HCMV membrane complexes of the invention may lack an N-terminal signal sequences. An example of a preferred gL protein of the invention is SEQ ID NO: 31, which lacks an N-terminal signal sequence and consists of amino acid residues 31-278 of SEQ ID NO: 7.

gL proteins of the invention can have various degrees of identity to SEQ ID NO: 7 such as at least 60%, 70%, 80%, 85%, 90%, 91%, 92%, 93%, 94%, 95%, 96%, 97%, 98% or 99% identical to the sequence recited in SEQ ID NO: 7. gL proteins of the invention can have various degrees of identity to SEQ ID NO: 31 such as at least 60%, 70%, 80%, 85%, 90%, 91%, 92%, 93%, 94%, 95%, 96%, 97%, 98% or 99% identical to the sequence recited in SEQ ID NO: 31. Preferred gL proteins: (i) can dimerise with HCMV gH; (ii) form part of the trimeric gH/gL/gO complex; (iii) form part of the pentameric gH/gL/pUL128/pUL130/pUL131A complex; (iv) comprise at least one epitope from SEQ ID NO: 7 or SEQ ID NO: 31; and/or (v) can elicit antibodies in vivo which immunologically cross-react with an HCMV virion.

HCMV glycoprotein O (gO), which is encoded by the UL74 gene, has been reported to act as a molecular chaperone, increasing gH/gL ER export and incorporation into virions. It has been proposed that gO competes with pUL128-131A for binding onto gH/gL but is released from gH/gL, so that gH/gL (lacking pUL128-131A) is incorporated into virions (Ryckman, Chase and Johnson 2010). Compared with other viral genes, HCMV gO is unusually variable among different HCMV strains: the variability of the gO amino acid sequence among 22 to 39 clinical isolates, as well as laboratory strains AD169, Towne and Toledo approached 45% (i.e. there was only 55% identity between the gO amino acid sequences between different isolates) (Rasmussen, et al. 2002). The gO from HCMV strains Merlin (GI:39842082, SEQ ID NO: 10), AD169 (GI: 136968, SEQ ID NO: 11) and Towne have been reported (GI:239909431, SEQ ID NO: 12) to consist of 472, 466 and 457 amino acids, respectively. The gO of HCMV strain AD169, which shares a 73% amino acid similarity to SEQ ID NO: 10, has 18 N-glycosylation sites (at residues 75, 83, 87, 103, 130, 157, 162, 171, 219, 242, 288, 292, 350, 385, 392, 399, 433 and 454), and may include a cleavable signal sequence at its N-terminus (predicted to consist of amino acid residues 1-30), which is absent from the mature polypeptide. Rigoutsos (2003) predicted the presence of TM domains (in regions 10-28 and 190-212) and a coiled coil region (residues 240-272).

Typically, the N-terminal signal sequence of gO proteins is cleaved by a host cell signal peptidase to produce mature gO proteins. The gO proteins in HCMV membrane complexes of the invention may lack an N-terminal signal sequences. An example of a preferred gO protein of the invention is SEQ ID NO: 32, which lacks an N-terminal signal sequence and consists of amino acid residues 31-472 of SEQ ID NO: 10.

gO proteins of the invention can have various degrees of identity to SEQ ID NO: 10 such as at least 55%, 60%, 65%, 70%, 75%, 80%, 85%, 90%, 91%, 92%, 93%, 94%, 95%, 96%, 97%, 98% or 99% identical to the sequence recited in SEQ ID NO: 10. gO proteins of the invention can have various degrees of identity to SEQ ID NO: 32 such as at least 60%, 70%, 80%, 85%, 90%, 91%, 92%, 93%, 94%, 95%, 96%, 97%, 98% or 99% identical to the sequence recited in SEQ ID NO: 32. Preferred gO proteins: (i) can form part of the trimeric gH/gL/gO complex; (ii) cannot form part of the pentameric gH/gL/pUL128/pUL130/pUL131A complex, (iii) comprise at least one epitope of SEQ ID NO: 10 or SEQ ID NO: 32; and/or (iv) can elicit antibodies in vivo which immunologically cross-react with an HCMV virion.

The pUL128 from HCMV strain Merlin has been reported (GI:39842124, SEQ ID NO: 13) to consist of 130 amino acids and to contain a 1 nucleotide substitution causing premature termination. The pUL128 from HCMV strains Towne (GI:39841882, SEQ ID NO: 14) and AD169 (GI: 59803078, SEQ ID NO: 15) have been reported to consist of 171 amino acids. Due to the premature termination of SEQ ID NO: 13, SEQ ID NOs: 13 and 15 only share 75% identity over the full-length of SEQ ID NO: 15. pUL128 is predicted to have an N-terminal signal sequence, which is located at residues 1-27 of SEQ ID NO: 13, but it is predicted to lack a TM domain. An example of a preferred pUL128 protein of the invention is SEQ ID NO: 33, which lacks an N-terminal signal sequence and consists of amino acid residues 28-171 of SEQ ID NO: 14. SEQ ID NO: 33 also consists of amino acid residues 28-171 of SEQ ID NO: 15.

pUL128 proteins of the invention can have various degrees of identity to SEQ ID NO: 15 such as at least 60%, 70%, 75%, 76%, 77%, 78%, 79%, 80%, 81%. 82%, 83%, 84%, 85%, 86%, 87%, 88%, 89%, 90%, 91%, 92%, 93%, 94%, 95%, 96%, 97%, 98% or 99% identical to the sequence recited in SEQ ID NO: 15. pUL128 proteins of the invention can have various degrees of identity to SEQ ID NO: 33 such as at least 60%, 70%, 75%, 76%, 77%, 78%, 79%, 80%, 81%. 82%, 83%, 84%, 85%, 86%, 87%, 88%, 89%, 90%, 91%, 92%, 93%, 94%, 95%, 96%, 97%, 98% or 99% identical to the sequence recited in SEQ ID NO: 33. Preferred pUL128 proteins: (i) can form part of the pentameric gH/gL/pUL128/pUL130/pUL131A complex, (ii) comprise at least one epitope of SEQ ID NO: 15 or SEQ ID NO: 33, and/or (iii) can elicit antibodies in vivo which immunologically cross-react with an HCMV virion.

UL130 is the central and the largest (214 codons) gene of the UL131A-128 locus. Conceptual translation of the gene predicts a long (25 amino acids) N-terminal signal sequence that precedes a hydrophilic protein containing two potential N-linked glycosylation sites (Asn85 and Asn118) within a putative chemokine domain (amino acids 46 to 120) and an additional N-glycosylation site (Asn201) close to the end of a unique C-terminal region. pUL130 is predicted to lack a TM domain. It has been reported to be a luminal glycoprotein that is inefficiently secreted from infected cells but is incorporated into the virion envelope as a Golgi-matured form (Patrone, et al. 2005). The sequences of pUL130 from HCMV strain Merlin and Towne are publicly available (GI:39842125, SEQ ID NO: 16 and GI:239909473, SEQ ID NO: 17, respectively) and they consist of 214 and 229 amino acids, respectively. SEQ ID NO: 17 has been reported to contain a frameshift mutation in the C-terminal region of pUL130, and it shares 94% identity to the HCMV SEQ ID NO: 16 over the full-length of SEQ ID NO: 16.

Typically, the N-terminal signal sequence of pUL130 proteins is cleaved by a host cell signal peptidase to produce mature pUL130 proteins. The pUL130 proteins in HCMV membrane complexes of the invention may lack an N-terminal signal sequences. An example of a preferred pUL130 protein of the invention is SEQ ID NO: 34, which lacks an N-terminal signal sequence and consists of amino acid residues 26-214 of SEQ ID NO: 16.

pUL130 proteins of the invention can have various degrees of identity to SEQ ID NO: 16 such as at least 60%, 70%, 80%, 85%, 90%, 91%, 92%, 93%, 94%, 95%, 96%, 97%, 98% or 99% identical to the sequence recited in SEQ ID NO: 16. pUL130 proteins of the invention can have various degrees of identity to SEQ ID NO: 34 such as at least 60%, 70%, 80%, 85%, 90%, 91%, 92%, 93%, 94%, 95%, 96%, 97%, 98% or 99% identical to the sequence recited in SEQ ID NO: 34. As an alternative, pUL130 proteins of the invention can have various degrees of identity to SEQ ID NO: 17 such as at least 60%, 70%, 80%, 85%, 90%, 91%, 92%, 93%, 94%, 95%, 96%, 97%, 98% or 99% identical to the sequence recited in SEQ ID NO: 17. Preferred pUL130 proteins: (i) can form a pentameric gH/gL/pUL128/pUL130/pUL131A complex; (ii) comprise at least one epitope of SEQ ID NO: 16, SEQ ID NO: 34 or SEQ ID NO: 17, respectively; and/or (iii) can elicit antibodies in vivo which immunologically cross-react with an HCMV virion.

pUL131A function is required for HCMV replication not only in endothelial cells but also in epithelial cells. The pUL131A from HCMV strains Merlin (GI:39842126, SEQ ID NO: 18) and Towne (GI:239909474, SEQ ID NO: 19) and AD169 (GI:219879712, SEQ ID NO: 20) have been reported to consist of 129, 129 and 76 amino acids, respectively. pUL131A is predicted to contain an N-terminal signal sequence, which is located at residues 1-18 of SEQ ID NO:

18, and to lack a TM domain. The UL131A from strain AD169 has been reported to contain a 1-base-pair insertion, which causes a frame-shift (Wang and Shenk 2005). SEQ ID NO: 18 is 96% identical to SEQ ID NO: 20 over the N-terminal 28 amino acids, but it is only 36% identical to SEQ ID NO: 20 over the full-length of SEQ ID NO: 18 due to the frame-shift in the AD169 UL131A gene.

Typically, the N-terminal signal sequence of pUL131A proteins is cleaved by a host cell signal peptidase to produce mature pUL131A proteins. The pUL131A proteins in HCMV membrane complexes of the invention may lack an N-terminal signal sequences. An example of a preferred pUL131A protein of the invention is SEQ ID NO: 35, which lacks an N-terminal signal sequence and consists of amino acid residues 19-129 of SEQ ID NO: 18. SEQ ID NO: 35 also consists of amino acid residues 19-129 of SEQ ID NO: 19.

pUL131A proteins of the invention can have various degrees of identity to SEQ ID NO: 17 such as at least 60%, 70%, 80%, 85%, 90%, 91%, 92%, 93%, 94%, 95%, 96%, 97%, 98% or 99% identical to the sequence recited in SEQ ID NO: 18. pUL131A proteins of the invention can have various degrees of identity to SEQ ID NO: 35 such as at least 60%, 70%, 80%, 85%, 90%, 91%, 92%, 93%, 94%, 95%, 96%, 97%, 98% or 99% identical to the sequence recited in SEQ ID NO: 35. Preferred pUL131A proteins: (i) can form pentameric gH/gL/pUL128/pUL130/pUL131A complexes, (ii) comprise at least one epitope of SEQ ID NO: 18 or SEQ ID NO: 35; and/or (iii) can elicit antibodies in vivo which immunologically cross-react with an HCMV virion.

If a clinical isolate is passaged in fibroblasts, it can very rapidly accumulate a mutation in the UL131A-128 locus, precluding its ability to infect other cell types. Indeed, as few as three passages in fibroblasts can be sufficient for such mutations to appear in virus stocks. For example, compared to clinical isolates which have not been passaged in fibroblasts, Merlin and Toledo carry mutations in UL128, Towne carries a mutation in the UL130 ORF and AD169 contains a mutated UL131A ORF. Since clinical isolates, but not laboratory strains, efficiently infect and generate infectious progeny in epithelial cells, this cell type, like endothelial cells, holds promise as a laboratory host for the production of clinical HCMV stocks that are not selected for mutations in the UL131A-UL128 locus (Wang and Shenk 2005).

The invention provides an immunogenic composition comprising HCMV complexes, wherein said complexes comprise gH, gL and at least one more HCMV glycoprotein, e.g. gH/gL/gO or gH/gL/pUL128/pUL130/pUL131A. Such immunogenic compositions may additionally comprise other HCMV proteins (but preferably not non-envelope HCMV proteins), such as glycoprotein B (gB).

gB is encoded by UL55 and mediates fusion between the virus and the cell membrane. It therefore has a key role to play in entry and infection of the virus. Like many other viral fusion proteins, gB contains hydrophobic loops that insert into the cell membrane and it undergoes a large structural change (pre- and post-fusion conformation) during entry. Like gH, gB displays determinants that are recognized by the host factor TLR2, and it directly interacts with a heterodimer formed between the host factors TLR2 and TLR1. TLR2 mediates NF-κB activation and inflammatory cytokine responses from cells (Boehme, Guerrero and Compton 2006).

Glycoprotein B (gB) is the most highly conserved of the envelope glycoproteins of human herpesviruses. Although the structure of HCMV gB is currently unknown, it is assumed that the structure of HCMV gB is similar to that of the gBs of HSV and EBV based on sequence homology. The postfusion conformations of HSV-1 and EBV gBs also show a surprising degree of structural homology to the postfusion conformation of fusion protein (G) of vesicular stomatitis virus (VSV) protein, despite the lack of sequence similarity between the gBs of HSV-1 and EBV and VSV-G.

The gB from HCMV strains Merlin (GI:39842076, SEQ ID NO: 21) and Towne (GI:138193, SEQ ID NO: 22) have been reported to consist of 907 amino acids. The gB from HCMV strain AD169 (GI:138192, SEQ ID NO: 23) has been reported to consist of 906 amino acids, have 19 N-glycosylation sites (at residues 37, 68, 73, 85, 208, 281, 286, 302, 341, 383, 405, 409, 417, 447, 452, 464, 465, 554, and 585) and consists of a signal sequence at its N-terminus (at amino acid residues 1-25), an extracellular region (residues 26-751), a TM domain (residues 752-772) and a cytoplasmic domain (residues 773-907) (Rigoutsos, et al. 2003). In a study of 53 women, five subtypes of gB were found among with nucleotide polymorphisms between them ranging from 28 to 124 bp (Murthy, et al. 2011). The gBs of HCMV strain Merlin and AD169 share 95% amino acid similarity. The N-terminal signal sequence is predicted to consist of amino acid residues 1-22 of SEQ ID NO: 21 in the HCMV strain Merlin gB.

Typically, the N-terminal signal sequence of gB proteins is cleaved by a host cell signal peptidase to produce mature gB proteins. The gB proteins in HCMV membrane complexes of the invention may lack an N-terminal signal sequences. An example of a preferred gB protein of the invention is SEQ ID NO: 36, which lacks an N-terminal signal sequence and consists of amino acid residues 23-907 of SEQ ID NO: 21.

gB proteins of the invention can have various degrees of identity to SEQ ID NO: 21 such as at least 70%, 80%, 85%, 86%, 87%, 88%, 89%, 90%, 91%, 92%, 93%, 94%, 95%, 96%, 97%, 98% or 99% identical to the sequence recited in SEQ ID NO: 21. gB proteins of the invention can have various degrees of identity to SEQ ID NO: 36 such as at least 70%, 80%, 85%, 86%, 87%, 88%, 89%, 90%, 91%, 92%, 93%, 94%, 95%, 96%, 97%, 98% or 99% identical to the sequence recited in SEQ ID NO: 36. Preferred gB proteins: (i) comprise at least one epitope of SEQ ID NO: 18 or SEQ ID NO: 36; and/or (ii) can elicit antibodies in vivo which immunologically cross-react with an HCMV virion.

Glycosylation

Although gH, gL, gO, gB and pUL130 may be referred to as glycoproteins, this nomenclature should not be taken to mean that these proteins must be glycosylated when used with the invention. On the contrary, in some embodiments of the invention, one or more of polypeptides are not glycosylated. Usually, however, one or more (or all) polypeptides in a complex of the invention are glycosylated. In some embodiments, one or more (or all) polypeptides in a complex of the invention are glycosylated by glycosylation mutants of cultured cells, such as mutated mammalian cells. Such glycosylation mutants produce a pattern of polypeptide glycosylation which differs from a wild-type pattern of glycosylation, i.e. the resulting polypeptide glycoforms differs from wild-type glycoforms.

The level and type of glycosylation is dependent on the species of the host cell. In general, the species most distant to humans in evolutionary terms, such as bacteria, yeasts, fungi, insects and plants, have glycosylation repertoires that are least similar to that of humans. Proteins are usually not glycosylated in bacterial cells, although the transfer of N-linked glycosylation systems into *Escherichia coli* has been reported (Langdon, Cuccui and Wren 2009). Proteins can be glycosylated in insect cells. However, unlike vertebrate cells, insect cells are unable to produce complex N-linked side chains with penultimate galactose and terminal sialic acid. Hence, the type of glycosylation in insect cells can be sub-optimal for therapeutic proteins. Yeast cells can perform N-linked (to asparagine) and O-linked (to serine/threonine) glycosylation using mannose. Hyperglycosylation (outer chain extension) in the Golgi is a characteristic feature of yeast cells which is not typical of mammalian cells, and this can lead to problems with antibody reactivity. Also, unlike mammalian cells, yeast cells are unable to incorporate sugars other than mannose. In contrast to yeast and insect cells, mammalian glycoproteins expressed in mammalian cells are authentically glycosylated resulting in a recombinant product most similar to that formed in vivo.

Hence, preferably glycosylated polypeptides in complexes of the invention: (i) have a mammalian glycosylation pattern; and/or (ii) do not contain an insect cell pattern of glycosylation. In some embodiments, one or more of the proteins of the invention contain complex N-linked side chains with penultimate galactose and terminal sialic acid.

Membrane Protein Complexes of the Invention

HCMV membrane protein complexes of the invention are hetero-oligomeric associations between gH, gL and at least one additional HCMV protein. The proteins in these complexes may be associated by non-covalent and/or covalent interactions. In the gH/gL/gO trimeric complex, disulfide bonds link gH to gO and gL. In the pentameric complex of the invention, gH, gL and pUL128 are typically linked through disulfide bonds, but pUL130 and pUL131A are typically incorporated into the pentameric complex by non-covalent interactions (as shown in Example 7). In some embodiments, the pUL130 protein of the invention and/or pUL131A protein of the invention is incorporated into the pentameric complex by non-covalent interactions. Furthermore, the pUL130 protein of the invention and/or pUL131A may be inter-linked by non-covalent interactions.

The stoichiometries of the trimeric and pentameric complexes are assumed to be 1:1:1 (Huber and Compton 1999) and 1:1:1:1:1 (Ryckman, Chase and Johnson 2010), respectively, but this has yet to be definitively confirmed.

The inventors have discovered that the membrane protein complexes of the invention are able to induce an immunogenic response. Membrane protein complexes of the invention may thus be able to induce immunity against HCMV infection. These two functions are dependent on the retention of epitopes on the membrane protein complexes of the invention that can elicit the production of antibodies, including neutralizing antibodies. A range of conformational epitopes for the pentameric complex are known. For example, Macagno (2010) isolated a panel of human monoclonal antibodies that neutralized HCMV infection of endothelial, epithelial, and myeloid cells. With the single exception of an antibody that bound to a conserved epitope in the UL128 gene product, all other antibodies bound to conformational epitopes that required expression of two or more proteins of the gH/gL/UL128-131A complex. Preferably, the pentameric complexes of the invention possess one or more of the conformational epitopes identified by Macagno (2010).

Each protein of the invention may contain mutations, such as insertions, deletions and substitutions relative to the Merlin strain and/or the AD169 strain of HCMV, so long as these mutations are not detrimental to the use of the proteins as antigens, in particular so long as they retain one or more epitopes that can elicit the production of antibodies that can bind to at least a membrane protein complex of the Merlin and/or AD169 strain of HCMV and/or antibodies that can neutralize the biological effects of said HCMV membrane protein complex. In addition, such mutations should not prevent the capacity of the proteins to form a membrane protein complex of the invention. The ability to form a membrane protein complex of the invention can be tested by performing protein purification, and analyzing the proteins by non-reducing PAGE, Western blot and/or size exclusion chromatography. If the proteins form part of a complex, they may all be present in a single band on a native PAGE gel and/or be present in a single peak in a size exclusion chromatogram.

The HCMV membrane protein complex of the invention can be prepared at various levels of purity e.g. at least 80%, 85%, 90%, 95%, or 99% of total protein by mass, i.e. the complex makes up at least 80% of the total proteinaceous mass in a composition. The composition may be free from polyacrylamide.

Expression Systems

In one aspect, the invention provides a process for expressing the membrane protein complex of the invention. Suitable expression systems for use in the present invention are well known to those of skill in the art and many are described in detail in Doyle (2008). Generally, any system or vector that is suitable to maintain, propagate and express nucleic acid molecules to produce a polypeptide in the required host may be used. The appropriate nucleotide sequence may be inserted into an expression system by any of a variety of well-known and routine techniques, such as, for example, those described in Sambrook (2000). Generally, the encoding gene can be placed under the control of a control element such as a promoter, and, optionally, an operator, so that the DNA sequence encoding the desired peptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Suitable expression systems include microorganisms such as bacteria transformed with recombinant bacteriophage, plasmid or cosmid DNA expression vectors; yeast transformed with yeast expression vectors; insect cell systems infected or transfected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the proteins of the invention. Preferably, the proteins of the invention are produced in eukaryotic cells, such as mammalian cells.

Recombinant polypeptides may be expressed transiently or stably. Preferably, the recombinant proteins are expressed stably. For example, cell lines that stably express the peptide of interest may be transfected using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, human embryonic kidney (HEK) 293, Bowes melanoma and human hepatocellular carcinoma (for example Hep G2) cells and a number of other cell lines. Expression in mammalian cells is preferable because the proteins that are produced will have authentic mammalian glycosylation patterns, and thus possess epitopes that are present on infectious HCMV particles. Accordingly, production of membrane protein complexes of the invention in mammalian cells will lead to the production of antibodies that are able to bind to naturally occurring HCMV particles during infection.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers et al. (Summers and Smith 1987). Particularly suitable host cells for use in this system include insect cells such as *Drosophila* S2 (i.e. by recombinant baculovirus infection of stably transfected *Drosophila* S2 cells) and *Spodoptera* Sf9 cells. In some embodiments, the proteins of the invention are not produced in insect cells.

There are many plant cell culture and whole plant genetic expression systems known in the art. Examples of suitable plant cellular genetic expression systems include those described in U.S. Pat. No. 5,693,506; U.S. Pat. No. 5,659,122; U.S. Pat. No. 5,608,143 and Zenk (1991)[23]. In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of prokaryotic expression systems include those that use *streptococci, staphylococci, E. coli, Streptomyces* and *Bacillus subtilis* as host cells.

Examples of fungal expression systems include those that use yeast (for example, *S. cerevisiae*) and *Aspergillus* as host cells.

HEK293 cells are suitable for transient expression of the HCMV proteins of the invention due to their high transfectability by various techniques, including the calcium phosphate and polyethylenimine (PEI) methods. A useful cell line of HEK293 is one that expresses the EBNA1 protein of EBV, such as 293-6E (Loignon, et al. 2008). Transformed HEK293 cells have been shown to secrete high levels of the protein complexes of the invention into the growth medium, thus allowing the purification of such protein complexes directly from the growth medium.

CHO cells are particularly suitable mammalian hosts for industrial production of the HCMV proteins of the invention for use as immunogens or antigens because they allow long-term, stable gene expression and high yields of proteins.

In some embodiments, the membrane protein complexes of the invention are secreted from the cells in which they are expressed. In other embodiments of the invention, the proteins of the invention are not secreted. In *E. coli*, for example, non-secreted proteins may accumulate in inclusion bodies. Methods for purifying recombinant proteins from inclusion bodies are well known in the art.

Transfection can be carried out by a range of methods including using calcium phosphate, electroporation, or by mixing a cationic lipid with the material to produce liposomes which fuse with the cell membrane and deposit their cargo inside.

Nucleic Acid Constructs

The invention provides a recombinant nucleic acid which encodes gL, gH that lacks a TM domain, and at least one additional HCMV glycoprotein. Preferably, said recombinant nucleic acid: (a) is not a self-replicating RNA molecule; (b) is no an alphavirus replicon; (c) does not encode any alphavirus nonstructural proteins, such as NSP1, NSP2, NSP3 and NSP4; (d) does nor contain: an Internal Ribosomal Entry Site (IRES), such as EMCV or EV71; and/or (e) does not contain a viral 2A site, such as FMDV. An example of said recombinant nucleic acid may be a single construct which encodes a gL protein of the invention, a gH protein of the invention, a pUL128 protein of the invention, a pUL130 protein of the invention and a pUL131 protein of the invention.

The invention also provides a plurality of recombinant nucleic acids which encode one or more proteins of the invention. For example, in one embodiment the invention provides two nucleic acid constructs: the first construct encoding a gH protein of the invention and a gL protein of the invention, and the second construct encoding a pUL128 protein of the invention, a pUL130 protein of the invention and a pUL131A protein of the invention.

The invention also provides a plurality of recombinant nucleic acids comprising: a first recombinant nucleic acid molecule which encodes a gL protein of the invention; a second recombinant nucleic acid molecule which encodes a gH protein of the invention; and one or more third recombinant nucleic acid molecules which encode one or more additional HCMV proteins. Preferably, said first, second and/or third recombinant nucleic acid molecule(s): (a) is/are not a self-replicating RNA molecule; (b) is/are not (an) alphavirus replicon(s); (c) do(es) not encode any alphavirus nonstructural proteins, such as NSP1, NSP2, NSP3 and NSP4; (d) do(es) not contain: an Internal Ribosomal Entry Site (IRES), such as EMCV or EV71; and/or (e) do(es) not contain a viral 2A site, such as FMDV.

In one embodiment, the third recombinant nucleic acid molecule encodes a gO protein of the invention and in another embodiment the third recombinant nucleic acid molecule(s) encode(s) pUL128, pUL130 and pUL131A proteins of the invention. Thus the sequences encoding each individual polypeptide in a complex can be present in a single nucleic acid molecule, or distributed among two or more nucleic acid molecules.

In one embodiment, the invention provides a plurality of recombinant nucleic acids comprising: (i) a first recombinant nucleic acid molecule which encodes a gL protein of the invention, (ii) a second recombinant nucleic acid molecule which encodes a gH protein of the invention, (iii) a third recombinant nucleic acid molecule which encodes a pUL128 protein of the invention, (iv) a fourth recombinant nucleic acid molecule which encodes a pUL130 protein of the invention, and (v) a fifth recombinant nucleic acid molecule which encodes a pUL131A protein of the invention. Preferably, said first, second, third, fourth and/or fifth recombinant nucleic acid molecule(s): (a) is/are not a self-replicating RNA molecule; (b) is/are not (an) alphavirus replicon(s); (b) do(es) not encode any alphavirus nonstructural proteins, such as NSP1, NSP2, NSP3 and NSP4; (c) do(es) not contain: an Internal Ribosomal Entry Site (IRES), such as EMCV or EV71; and/or (d) do(es) not contain a viral 2A site, such as FMDV.

Nucleic acid molecules which encode a gH protein of the invention can have various degrees of identity to SEQ ID NO: 24 such as at least 89% 90%, 91%, 92%, 93%, 94%, 95%, 96%, 97%, 98% or 99% identical to the sequence recited in SEQ ID NO: 24. Nucleic acid molecules which encode a gL protein of the invention can have various degrees of identity to SEQ ID NO: 25 such as at least 89%, 90%, 91%, 92%, 93%, 94%, 95%, 96%, 97%, 98% or 99% identical to the sequence recited in SEQ ID NO: 25. Nucleic acid molecules which encode a pUL128 protein of the invention can have various degrees of identity to SEQ ID NO: 26 such as at least 74%, 76%, 78%, 80%, 82%, 84%, 86%, 88%, 90%, 91%, 92%, 93%, 94%, 95%, 96%, 97%, 98% or 99% identical to the sequence recited in SEQ ID NO: 26. Nucleic acid molecules which encode a pUL130 protein of the invention can have various degrees of identity to SEQ ID NO: 27 such as at least 74%, 76%, 78%, 80%, 82%, 84%, 86%, 88%, 90%, 91%, 92%, 93%, 94%, 95%, 96%, 97%, 98% or 99% identical to the sequence recited in SEQ ID NO: 27. Nucleic acid molecules which encode a pUL131A protein of the invention can have various degrees of identity to SEQ ID NO: 28 such as at least 74%, 76%, 78%, 80%, 82%, 84%, 86%, 88%, 90%, 91%, 92%, 93%, 94%, 95%, 96%, 97%, 98% or 99% identical to the sequence recited in SEQ ID NO: 28.

The nucleic acids of the invention may comprise genomic DNA and/or cDNAs. Unlike cDNA, genomic DNA may contain introns. Some genes are expressed more efficiently when introns are present. Genomic UL128 and UL131A genes each consist of two exons, whereas UL130 does not contain any introns. If genomic sequences are used, the proteins that are produced will depend on splicing, which can vary according to which expression system is used.

The invention provides vectors that comprise said nucleic acids, wherein said vectors include suitable promoters and terminators. Said recombinant nucleic acids may be plasmids, or may be incorporated into the genome of a cell. The promoters in these vectors can be HCMV promoters or non-HCMV promoters.

The invention also provides a process for expressing an HCMV membrane protein complex comprising gH, gL and at least one more HCMV glycoprotein by introducing one or more recombinant nucleic acid molecules which encode gH, gL and at least one more HCMV glycoprotein into an expression system; expressing said one or more nucleic acids in said expression system; and purifying said HCMV membrane protein complex. In some embodiments, this process comprises transfecting cells with a first nucleic acid construct which encodes: either gH, gL, pUL128, pUL130 and pUL131A proteins of the invention or gH, gL and gO proteins of the invention. In some embodiments, this process may comprise transfecting cells with a first nucleic acid construct which encodes a gH protein of the invention, a second nucleic acid construct which encodes a gL protein of the invention; and one or more third nucleic acid construct(s) which encode(s) one or more additional HCMV glycoprotein(s) of the invention. In some embodiments, this process may comprise transfecting cells with a first nucleic acid construct which encodes a gH protein of the invention and a gL protein of the invention; and a second nucleic acid construct(s) which encode(s) one or more additional HCMV glycoprotein(s) of the invention, such as gO or pUL128, pUL130 and pUL131A.

Said HCMV membrane protein complex may be expressed in a mammalian cell. Said isolated HCMV membrane protein complex may optionally be purified.

Cells of the Invention

The invention also provides a cell that expresses a nucleic acid molecule or plurality of nucleic acid molecules of the invention, wherein said cell does not comprise the full HCMV genome. Said cell may be stably transformed with said nucleic acid molecule or plurality of nucleic acid molecules of the invention. Preferably, said cell is a mammalian cell, for example a CHO cell.

The invention provides a cell comprising gH, gL and at least one additional HCMV glycoprotein, wherein said cell does not contain the HCMV genome and/or does not produce HCMV virions and/or does not express any non-envelope HCMV proteins.

Isolation and Purification of Membrane Protein Complexes

Complexes of the invention are preferably prepared and used in isolated form. The term "isolated" as used herein means removed from its natural environment. Hence, an "isolated HCMV membrane protein complex" does not encompass the HCMV membrane protein complex on the surface of HCMV infected cells or within an infectious HCMV virion.

Using the expression methods described in the examples, the complexes of the invention can be produced at high yields. [See above].

The invention provides processes for purifying HCMV membrane complexes of the invention. Such processes of the invention allow for production of the HCMV membrane protein complex at a purity of >85%, >86%, >87%, >88%, >89%, >90%, >91%, >92%, >93%, >94% or >95% of total protein by mass, as determined by gel electrophoresis. These high levels of purity make the complexes suitable for use as an immunogen in diagnostic applications or as an antigen in vaccine formulations.

The invention provides a process for purifying an HCMV membrane protein complex of the invention, wherein said purification comprises one or more chromatographic steps. Said chromatographic steps may comprise affinity chromatography, such as $Ni^{2+}$ affinity chromatography and/or size exclusion chromatography.

Compositions

The invention also provides compositions comprising the isolated HCMV membrane protein complexes of the invention. The invention also provides compositions comprising the purified HCMV membrane protein complexes of the invention.

The HCMV membrane protein complex can be incorporated into an immunogenic composition, or a vaccine composition. Such compositions can be used to raise antibodies in a mammal (e.g. a human).

The invention provides pharmaceutical compositions comprising an HCMV membrane protein complex of the invention. Similarly, the invention provides processes for making a pharmaceutical composition involving combining an HCMV membrane protein complex of the invention with a pharmaceutically acceptable carrier.

In addition to their antigens, immunogenic and pharmaceutical compositions of the invention typically include a pharmaceutically acceptable carrier, and a thorough discussion of such carriers is available in *Remington: The Science and Practice of Pharmacy*.

The pH of the composition is usually between 6 and 8, and more preferably between 6.5 and 7.5 (e.g. about 7). Stable pH may be maintained by the use of a buffer e.g. a Tris buffer, a citrate buffer, phosphate buffer, or a histidine buffer. Thus a composition will generally include a buffer.

A composition may be sterile and/or pyrogen-free. Compositions may be isotonic with respect to humans.

A composition comprises an immunologically effective amount of its antigen(s). An 'immunologically effective amount' is an amount which, when administered to a subject, is effective for eliciting an antibody response against the antigen. This amount can vary depending upon the health and physical condition of the individual to be treated, their age, the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the mass of protein per dose. A dose of 10-500 μg (e.g. 50 μg) per antigen can be useful.

Immunogenic compositions may include an immunological adjuvant. Thus, for example, they may include an aluminium salt adjuvant or an oil-in-water emulsion (e.g. an oil-in-water emulsion comprising squalene, such as MF59 or AS03). Suitable aluminium salts include hydroxides (e.g. oxyhydroxides), phosphates (e.g. hydroxyphosphates, orthophosphates), (e.g. see chapters 8 & 9 of *Vaccine Design . . .* (1995) eds. Powell & Newman. ISBN: 030644867X. Plenum), or mixtures thereof. The salts can take any suitable form (e.g. gel, crystalline, amorphous, etc.), with adsorption of antigen to the salt being preferred. The concentration of $Al^{+++}$ in a composition for administration to a patient is preferably less than 5 mg/ml e.g. <4 mg/ml, <3 mg/ml, <2 mg/ml, <1 mg/ml, etc. A preferred range is between 0.3 and 1 mg/ml. A maximum of 0.85 mg/dose is preferred. Aluminium hydroxide and aluminium phosphate adjuvants are particularly suitable for use with the invention.

One suitable immunological adjuvant comprises a compound of Formula (I) as defined in WO2011/027222, or a pharmaceutically acceptable salt thereof, adsorbed to an aluminum salt. Many further adjuvants can be used, including any of those disclosed in Powell & Newman (1995).

Compositions may include an antimicrobial, particularly when packaged in multiple dose format. Antimicrobials such as thiomersal and 2-phenoxyethanol are commonly found in vaccines, but it is preferred to use either a mercury-free preservative or no preservative at all.

Compositions may comprise detergent e.g. a polysorbate, such as polysorbate 80. Detergents are generally present at low levels e.g. <0.01%.

Compositions may include sodium salts (e.g. sodium chloride) to give tonicity. A concentration of 10+2 mg/ml NaCl is typical e.g. about 9 mg/ml.

Compositions of the invention will generally be administered directly to a subject. Direct delivery may be accomplished by parenteral injection (e.g. subcutaneously, intraperitoneally, intravenously, intramuscularly, or to the interstitial space of a tissue), or by any other suitable route. Intramuscular administration is preferred e.g. to the thigh or the upper arm. Injection may be via a needle (e.g. a hypodermic needle), but needle-free injection may alternatively be used. A typical intramuscular dosage volume is 0.5 ml.

Administration can involve a single dose schedule or a multiple dose schedule.

The subject who is immunised is a human being, who may be any age e.g. 0-12 months old, 1-5 years old, 5-18 years old, 18-55 years old, or more than 55 years old.

Vaccines of the invention may be prophylactic (i.e. to prevent disease) or therapeutic (i.e. to reduce or eliminate the symptoms of a disease).

Isolated and/or purified HCMV membrane protein complexes of the invention can be administered alone or as either prime or boost in mixed-modality regimes, such as a RNA prime followed by a protein boost. Benefits of the RNA prime protein boost strategy, as compared to a protein prime protein boost strategy, include, for example, increased antibody titers, a more balanced IgG1:IgG2a subtype profile, induction of TH1-type CD4+ T cell-mediated immune response that was similar to that of viral particles, and reduced production of non-neutralizing antibodies. The RNA prime can increase the immunogenicity of compositions regardless of whether they contain or do not contain an adjuvant.

In the RNA prime-protein boost strategy, the RNA and the protein are directed to the same target antigen. Examples of suitable modes of delivering RNAs include virus-like replicon particles (VRPs), alphavirus RNA, replicons encapsulated in lipid nanoparticles (LNPs) or formulated RNAs, such as replicons formulated with cationic nanoemulsions (CNEs). Suitable cationic oil-in-water nanoemulsions are disclosed in WO2012/006380 e.g. comprising an oil core (e.g. comprising squalene) and a cationic lipid (e.g. DOTAP, DMTAP, DSTAP, DC-cholesterol, etc.).

WO2012/051211 discloses that antibodies to the pentameric complex are produced in mice that have been immunized with VRPs and formulated RNAs (CNEs and LNPs) that encode the protein constituents of the pentameric complex. These antibodies have been found to be capable of neutralizing HCMV infection in epithelial cells. The RNA prime-protein boost regimen may involve first (e.g. at weeks 0-8) performing one or more priming immunization(s) with RNA (which could be delivered as VRPs, LNPs, CNEs, etc.) that encodes one or more of the protein components of an HCMV membrane protein complex of the invention and then perform one or more boosting immunization(s) later (e.g. at weeks 24-58) with: an isolated HCMV membrane protein complex of the invention, optionally formulated with an adjuvant or a purified HCMV membrane protein complex of the invention, optionally formulated with an adjuvant.

The invention thus provides an immunogenic composition comprising: a self-replicating RNA molecule that encodes a first polypeptide HCMV antigen comprising a first epitope; and a second polypeptide HCMV antigen comprising a second epitope. The invention also relates to kits comprising: (i) a priming composition comprising a self-replicating RNA molecule that encodes a first polypeptide antigen that comprises a first epitope from a pathogen; and (ii) a boosting composition comprising a second polypeptide antigen that comprises a second epitope from the pathogen.

Antigens may be independently selected from the group consisting of gB, gH, gL, gO, pUL128, pUL130 and pUL131A. Said first polypeptide HCMV antigen is preferably an HCMV membrane protein complex of the invention, such as the trimeric gH/gL/gO complex or the pentameric complex. Said second polypeptide HCMV antigen is preferably: an isolated HCMV membrane protein complex of the invention, such as the trimeric gH/gL/gO complex or the pentameric complex or a purified HCMV membrane protein complex of the invention, such as the trimeric gH/gL/gO complex or the pentameric complex. The first and second polypeptide antigens can be substantially the same. The first polypeptide antigen can be a soluble or membrane anchored polypeptide, and the second polypeptide antigen can be a soluble polypeptide. The first polypeptide antigen can be a fusion polypeptide. The second polypeptide antigen can be a fusion polypeptide. The self-replicating RNA can be an alphavirus-derived RNA replicon.

The self-replicating RNA molecule can comprise one or more modified nucleotides. In some embodiments, the self-replicating RNA molecule encodes an HCMV membrane protein complex of the invention, such as the trimeric gH/gL/gO complex or the pentameric complex of the invention. In some embodiments, the second polypeptide antigen is a purified HCMV membrane protein complex of the invention, such as a purified trimeric gH/gL/gO complex or purified pentameric complex of the invention.

In some embodiments, the RNA molecule is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion or combinations thereof.

In some embodiments, the priming composition of the kit or the immunogenic composition further comprises a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-water emulsion, an emulsome, a polycationic peptide, or a cationic nanoemulsion.

Antibodies of the Invention

The invention provides antibodies which recognise an isolated and/or purified HCMV membrane protein complex of the invention, but which do not bind to any of isolated gH, gL, gO, pUL128, pUL130 or pUL131A polypeptides and/or do not bind to isolated gH-gL heterodimers.

As described below, antibodies of the invention may be human or humanised antibodies and/or they may be monoclonal or polyclonal antibodies.

Antibodies of the invention may be polyclonal or monoclonal. Monoclonal antibodies (mAbs) are preferred for many situations. The term "monoclonal" as originally used in relation to antibodies referred to antibodies produced by a single clonal line of immune cells, as opposed to "polyclonal" antibodies that, while all recognizing the same target protein, were produced by different B cells and would be directed to different epitopes on that protein. As used herein, the word "monoclonal" does not imply any particular cellular origin, but refers to any population of antibodies that display a single binding specificity and affinity for a particular epitope in the same target protein. This usage is normal in the art.

Thus a mAb may be produced using any suitable protein synthesis system, including immune cells, non-immune cells, acellular systems, etc. A mAb can thus be produced by a variety of techniques, including conventional monoclonal antibody methodology (e.g. the standard somatic cell hybridization technique of Kohler & Milstein), by viral or oncogenic transformation of B lymphocytes, by combinatorial synthesis, by phage display, etc. Thus antibodies of the invention may be raised in vivo using: an isolated HCMV membrane protein complex of the invention as an antigen or a purified HCMV membrane protein complex of the invention as an antigen. The animal which raises the antibodies can be a mouse, a rat, a rabbit, a goat, etc. As an alternative approach, antibodies may be identified using in vitro selection methods, such as phage display of antibodies.

Antibodies of the invention can take various forms. For instance, they may be native antibodies, as naturally found in mammals. Native antibodies are made up of heavy chains and light chains. The heavy and light chains are both divided into variable domains and constant domains. The ability of different antibodies to recognize different antigens arises from differences in their variable domains, in both the light and heavy chains. Light chains of native antibodies in vertebrate species are either kappa (κ) or lambda (λ), based on the amino acid sequences of their constant domains. The constant domain of a native antibody's heavy chains will be α, δ, ε, γ or μ, giving rise respectively to antibodies of IgA, IgD, IgE, IgG, or IgM class. Classes may be further divided into subclasses or isotypes e.g. IgG1, IgG2, IgG3, IgG4, IgA, IgA2, etc. Antibodies may also be classified by allotype e.g. a γ heavy chain may have G1m allotype a, f, x or z, G2m allotype n, or G3m allotype b0, b1, b3, b4, b5, c3, c5, g1, g5, s, t, u, or v; a κ light chain may have a Km(1), Km(2) or Km(3) allotype. A native IgG antibody has two identical light chains (one constant domain CL and one variable domain VL) and two identical heavy chains (three constant domains CH1 CH2 & CH3 and one variable domain VH), held together by disulfide bridges. The domain and three-dimensional structures of the different classes of native antibodies are well known.

Where an antibody of the invention has a light chain with a constant domain, it may be a κ or λ light chain. Where an antibody of the invention has a heavy chain with a constant domain, it may be an α, δ, ε, γ or μ heavy chain. Heavy chains in the γ class (i.e. IgG antibodies) are preferred.

Antibodies of the invention may be fragments of native antibodies that retain antigen binding activity. For instance, papain digestion of native antibodies produces two identical antigen-binding fragments, called "Fab" fragments, each with a single antigen-binding site, and a residual "Fc" fragment without antigen-binding activity. Pepsin treatment yields a "F(ab')2" fragment that has two antigen-binding sites. "Fv" is the minimum fragment of a native antibody that contains a complete antigen-binding site, consisting of a dimer of one heavy chain and one light chain variable domain. Thus an antibody of the invention may be Fab, Fab', F(ab')$_2$, Fv, or any other type, of fragment of a native antibody.

An antibody of the invention may be a "single-chain Fv" ("scFv" or "sFv"), comprising a VH and VL domain as a single polypeptide chain. Typically the VH and VL domains are joined by a short polypeptide linker (e.g. >12 amino acids) between the VH and VL domains that enables the scFv to form the desired structure for antigen binding. A typical way of expressing scFv proteins, at least for initial selection, is in the context of a phage display library or other combinatorial library. Multiple scFvs can be linked in a single polypeptide chain.

An antibody of the invention may be a "diabody" or "triabody" etc., comprising multiple linked Fv (scFv) fragments. By using a linker between the VH and VL domains that is too short to allow them to pair with each other (e.g. <12 amino acids), they are forced instead to pair with the complementary domains of another Fv fragment and thus create two antigen-binding sites. These antibodies may include CH and/or CL domains.

An antibody of the invention may be a single variable domain or VHH antibody. Antibodies naturally found in camelids (e.g. camels and llamas) and in sharks contain a heavy chain but no light chain. Thus antigen recognition is determined by a single variable domain, unlike a mammalian native antibody. The constant domain of such antibodies can be omitted while retaining antigen binding activity. One way of expressing single variable domain antibodies, at least for initial selection, is in the context of a phage display library or other combinatorial library.

An antibody of the invention may be a "domain antibody" (dAb). Such dAbs are based on the variable domains of either a heavy or light chain of a human antibody and have a molecular weight of approximately 13 kDa (less than one-tenth the size of a full antibody). By pairing heavy and light chain dAbs that recognize different targets, antibodies with dual specificity can be made. dAbs are cleared from the body quickly and so benefit from a sustained release system, but can additionally be sustained in circulation by fusion to a second dAb that binds to a blood protein (e.g. to serum albumin), by conjugation to polymers (e.g. to a polyethylene glycol), or by other techniques.

The antibody may have a scaffold which is based on the fibronectin type III domain e.g. an adnectin or trinectin. The fibronectin-based scaffold is not an immunoglobulin, although the overall fold is closely related to that of the smallest functional antibody fragment. Because of this structure the non-immunoglobulin antibody mimics antigen binding properties that are similar in nature and affinity to those of natural antibodies. The FnIII domain has 7 or 8 beta strands which are distributed between two beta sheets, which themselves pack against each other to form the core of the protein, and further containing loops (analogous to antibody CDRs) which connect the beta strands to each other and are solvent exposed. There are at least three such loops at each edge of the beta sheet sandwich, where the edge is the boundary of the protein perpendicular to the direction of the beta strands. The FnIII loops can be replaced with immunoglobulin CDRs using standard cloning techniques, and can be used in a loop randomization and shuffling strategy in vitro that is similar to the process of affinity maturation of antibodies in vivo. The FnIII scaffold may be based on the tenth module of fibronectin type III (i.e. $^{10}$Fn3).

Thus the term "antibody" as used herein encompasses a range of proteins having diverse structural features, but usually including at least one immunoglobulin domain, having an all-β protein fold with a 2 layer sandwich of anti-parallel 3-strands arranged in two 3-sheets.

Antibodies used with the invention may include a single antigen binding site (e.g. as in a Fab fragment or a scFv) or multiple antigen binding sites (e.g. as in a F(ab')2 fragment or a diabody or a native antibody). Where an antibody has more than one antigen binding site then advantageously it can result in cross-linking of antigens.

Where an antibody has more than one antigen-binding site, the antibody may be mono specific (i.e. all antigen-binding sites recognize the same antigen) or it may be multi specific (i.e. the antigen-binding sites recognise more than one antigen).

An antibody of the invention may include a non-protein substance e.g. via covalent conjugation. For example, an antibody may include a radio isotope e.g. the ZEVALIN™ and BEXXAR™ products include $^{90}$Y and $^{131}$I isotopes, respectively. As a further example, an antibody may include a cytotoxic molecule e.g. MYLOTARG™ is linked to N-acetyl-γ calicheamicin, a bacterial toxin. As a further example, an antibody may include a covalently-attached polymer e.g. attachment of polyoxyethylated polyols or polyethylene glycol (PEG) has been reported to increase the circulating half-life of antibodies.

In some embodiments, an antibody can include one or more constant domains (e.g. including CH or CL domains). As mentioned above, the constant domains may form a κ or λ light chain or an α, δ, ε, γ or μ heavy chain. Where an antibody includes a constant domain, it may be a native constant domain or a modified constant domain. A heavy chain may include either three (as in α, γ, δ classes) or four (as in μ, ε classes) constant domains. Constant domains are not involved directly in the binding interaction between an antibody and an antigen, but they can provide various effector functions, including but not limited to: participation of the antibody in antibody dependent cellular cytotoxicity (ADCC); C1q binding; complement dependent cytotoxicity; Fc receptor binding; phagocytosis; and down regulation of cell surface receptors.

The constant domains can form a "Fc region", which is the C-terminal region of a native antibody's heavy chain. Where an antibody of the invention includes a Fc region, it may be a native Fc region or a modified Fc region. A Fc region is important for some antibodies' functions e.g. the activity of HERCEPTIN™ is Fc dependent. Although the boundaries of the Fc region of a native antibody may vary, the human IgG heavy chain Fc region is usually defined to stretch from an amino acid residue at position Cys226 or Pro230 to the heavy chain's C-terminus. The Fc region will typically be able to bind one or more Fc receptors, such as a FcγRI (CD64), a FcγRII (e.g. FcγRIIA, FcγRIIB1, FcγRIIB2, FcγRIIC), a FcγRIII (e.g. FcγRIIIA, FcγRIIIB), a FcRn, FcαR (CD89), FcδR, FcμR, a FcεRI (e.g. FcεRIαββγ2 or FcεRIαγ2), FcεRII (e.g. FcεRIIA or FcεRIIB), etc. The Fc region may also or alternatively be able to bind to a complement protein, such as C1q. Modifications to an antibody's Fc region can be used to change its effector function(s) e.g. to increase or decrease receptor binding affinity.

Antibodies will typically be glycosylated. N-linked glycans attached to the CH2 domain of a heavy chain, for instance, can influence C1q and FcR binding, with aglycosylated antibodies having lower affinity for these receptors. The glycan structure can also affect activity e.g. differences in complement-mediated cell death may be seen depending on the number of galactose sugars (0, 1 or 2) at the terminus of a glycan's biantennary chain. An antibody's glycans preferably do not lead to a human immunogenic response after administration.

Antibodies can be prepared in a form free from products with which they would naturally be associated. Contaminant components of an antibody's natural environment include materials such as enzymes, hormones, or other host cell proteins.

Useful antibodies have nanomolar or picomolar affinity constants for their target antigens e.g. $10^{-9}$ M, $10^{-10}$ M, $10^{-11}$ M, $10^{-12}$ M, $10^{-13}$ M or tighter). Such affinities can be determined using conventional analytical techniques e.g. using surface plasmon resonance techniques as embodied in BIAcore™ instrumentation and operated according to the manufacturer's instructions.

The monoclonal antibody used with the invention may be a human antibody, a humanized antibody, a chimeric antibody or (e.g. for veterinary purposes) a non-human antibody.

In some embodiments the antibodies are human mAbs. These can be prepared by various means. For example, human B cells producing an antigen of interest can be immortalized e.g. by infection with Epstein Barr Virus (EBV), optionally in the presence of a polyclonal B cell activator. Human monoclonal antibodies can also be produced in non-human hosts by replacing the host's own immune system with a functioning human immune system e.g. into Scid mice or Trimera mice. Transgenic and tran-schromosomic mice have been successfully used for generating human monoclonal antibodies, including the "humab mouse" from Medarex and the "xeno-mouse" from Abgenix, collectively referred to herein as "human Ig mice". Phage display has also been successful for this purpose. Unlike non-human antibodies, human antibodies will not elicit an immune response directed against their constant domains when administered to humans. Furthermore, the variable domains of these human antibodies are fully human (in particular the framework regions of the variable domains are fully human, in addition to the complementarity determining regions [CDRs]) and so will not elicit an immune response directed against the variable domain framework regions when administered to humans (except, potentially, for any anti-idiotypic response). Human antibodies do not include any sequences that do not have a human origin.

In some embodiments the antibodies are humanised mAbs, CDR-grafted mAbs or chimeric mAbs. These can be prepared by various means. For example, they may be prepared based on the sequence of a non-human (e.g. murine) monoclonal antibody. DNA encoding the non-human heavy and light chain immunoglobulins can be obtained and engineered to contain human immunoglobulin sequences using standard molecular biology techniques. For example, to create a chimeric antibody, the murine variable regions can be linked to human constant regions using methods known in the art. To create a CDR-grafted antibody, the murine CDR regions can be inserted into a human framework. To create a humanized antibody, one or more non-CDR variable framework residue(s) is also altered. The H1, H2 and H3 CDRs may be transferred together into an acceptor VH domain, but it may also be adequate to transfer only one or two of them. Similarly, one two or all three of the L1, L2 and L3 CDRs may be transferred into an acceptor VL domain. Preferred antibodies will have 1, 2, 3, 4, 5 or all 6 of the donor CDRs. Where only one CDR is transferred, it will typically not be the L2 CDR, which is usually the shortest of the six. Typically the donor CDRs will all be from the same human antibody, but it is also possible to mix them e.g. to transfer the light chain CDRs from a first antibody and the heavy chain CDRs from a second antibody.

In some embodiments the antibodies are non-human mAbs. These can be prepared by various means e.g. the original Kohler & Milstein technique for preparing murine mAbs.

Methods for Raising Antibodies of the Invention

The invention also provides a method for raising antibodies using: isolated HCMV membrane protein complexes of the invention or purified HCMV membrane protein complexes of the invention. These antibodies may be human or humanised. Preferably, these antibodies are specific to the isolated HCMV membrane protein complexes of the invention, and do not bind to isolated gH, gL, gO, pUL128, pUL130 or pUL131A. Such antibodies may be used for diagnostic assays, and may be labelled directly or indirectly. A wide range of antibody labels are known in the art. In other embodiments of the invention, antibodies of the invention can be used for therapy, e.g. in the treatment of HCMV infection, and may be in the form of neutralizing antibodies, which can inhibit or neutralize the antigen's biological activity.

Definitions

"Recombinant" as used herein to describe a polynucleotide means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, $x \pm 10\%$.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Sequence identity between polypeptide sequences is preferably determined by pairwise alignment algorithm using the Needleman-Wunsch global alignment algorithm (Needleman and Wunsch 1970), using default parameters (e.g. with Gap opening penalty=10.0, and with Gap extension penalty=0.5, using the EBLOSUM62 scoring matrix). This algorithm is conveniently implemented in the needle tool in the EMBOSS package (Rice, Longden and Bleasby 2000). Sequence identity should be calculated over the entire length of the polypeptide sequence of the invention.

Particular Embodiments of the Invention

Particular embodiments of the invention include:

1. A process for producing an isolated HCMV membrane protein complex comprising gH, gL and at least one additional HCMV glycoprotein, wherein said process comprises recombinant expression of said gH, gL and at least one more HCMV glycoprotein.
2. The process of claim 1, wherein said process comprises the purification of the HCMV membrane protein complex.
3. A process for expressing an HCMV membrane protein complex comprising gH, gL and at least one more HCMV glycoprotein by:
   introducing one or more recombinant nucleic acid molecules which encode gH, gL and at least one more HCMV glycoprotein into an expression system;
   expressing said one or more nucleic acids in said expression system; and
   purifying said membrane protein complex.

4. The process of claim 3, which comprises the step of transfecting cells with a first nucleic acid construct which encodes a fragment of gH that lacks the transmembrane domain, a second nucleic acid construct which encodes the gL protein; and a third nucleic acid construct which encodes at least one more HCMV glycoprotein.

5. The process of claim 3 or claim 4, wherein said HCMV membrane protein complex is expressed in a mammalian cell.

6. A process for producing a purified HCMV membrane protein complex comprising gH, gL and at least one more HCMV glycoprotein, wherein said process comprises expressing said HCMV membrane protein complex according to the process of claim 3 and purifying the isolated HCMV membrane protein complex.

7. The process of any preceding claim, wherein the HCMV membrane protein complex consists of gH, gL and gO.

8. The process of any preceding claim, wherein the HCMV membrane protein complex consists of gH, gL, pUL128, pUL130 and pUL131A.
   The process of any preceding claim, wherein said gH comprises or consists of any one of the sequences recited in SEQ ID NOs: 1, 2, 3, 4, 6, 29 or 30; and/or said gL comprises or consists of any one of the sequences recited in SEQ ID NOs: 7, 8, 9 or 31.

9. The process of claim 7, wherein said gO comprises or consists of any one of the sequences recited in SEQ ID NOs: 10, 11, 12 or 32.

10. The process of claim 8 or claim 9, wherein said:
    pUL128 comprises or consists of any one of the sequences recited in SEQ ID NOs: 13, 14, 15 or 33;
    pUL130 comprises or consists of any one of the sequences recited in SEQ ID NOs: 16, 17 or 34; and/or
    pUL131A comprises or consists of any one of the sequences recited in SEQ ID NOs: 18, 19, 20 or 35.

11. The process of any preceding claim, wherein said:
    gH comprises or consists of sequences which is at least 70% identical to any one of the sequences recited in SEQ ID NOs: 1, 2, 3, 4, 6, 29 or 30; and/or
    gL comprises or consists of sequences which is at least 70% identical to any one of the sequences recited in SEQ ID NOs: SEQ ID NOs: 7, 8, 9 or 31.

12. The process of claim 11, wherein said gO comprises or consists of sequences which is at least 70% identical to any one of the sequences recited in SEQ ID NOs: SEQ ID NOs: 10, 11, 12 or 32.

13. The process of claim 12, wherein said:
    pUL128 comprises or consists of sequences which is at least 70% identical to any one of the sequences recited in SEQ ID NOs: 13, 14, 15 or 33;
    pUL130 comprises or consists of sequences which is at least 70% identical to any one of the sequences recited in SEQ ID NOs: 16, 17 or 34; and/or
    pUL131A comprises or consists of sequences which is at least 70% identical to any one of the sequences recited in SEQ ID NOs: 18, 19, 20 or 35.

14. A process for purifying an HCMV membrane protein complex as defined in any one of the preceding claims, wherein said purification comprises one or more chromatographic steps.

15. The process of claim 14, wherein said chromatographic steps comprise affinity chromatography, preferably $Ni^{2+}$ affinity chromatography and/or size exclusion chromatography.

16. The process of any preceding claim, wherein the HCMV membrane protein complex has a purity of >85%, >86%, >87%, >88%, >89%, >90%, >91%, >92%, >93%, >94% or >95% by mass.

17. The process of any preceding claim, wherein one or more of gH, gL, gO, pUL128, pUL130 and pUL131A in said HCMV membrane protein complex:
    have a mammalian glycosylation pattern; and/or
    do not contain an insect cell pattern of glycosylation.

18. A purified HCMV membrane protein complex comprising gH, gL and at least one more HCMV glycoprotein.

19. An HCMV membrane protein complex comprising gH, gL and at least one more HCMV glycoprotein, wherein said complex is produced by the process of any preceding claim.

20. A composition comprising the isolated HCMV membrane protein complex of claim 18 or claim 19.

21. The composition of claim 20, wherein said composition does not contain polyacrylamide.

22. The composition of claim 20 or claim 21, wherein said composition does not contain HCMV tegument or capsid proteins.

23. The composition of any one of claims 20-22, wherein said composition is a liquid.

24. The composition of any one of claims 20-23, wherein said composition is an immunogenic composition.

25. The immunogenic composition of claim 24, which comprises gB.

26. The immunogenic composition of claim 25, wherein said gB comprises or consists of any one of the sequences recited in SEQ ID NOs: 21, 22, 23 or 36.

27. The immunogenic composition of claim 26, wherein said gB comprises or consists of a sequence which is at least 70% identical to any one of the sequences recited in SEQ ID NOs: 21, 22, 23 or 36.

28. The immunogenic composition of any one of claims 25-27, wherein said gB:
    has a mammalian glycosylation pattern; and/or
    does not contain an insect cell pattern of glycosylation.

29. The immunogenic composition of any one of claim 24-28, wherein said composition is a vaccine.

30. The immunogenic composition of any one of claims 24-29, which comprises an adjuvant.

31. The immunogenic composition of claim 30, wherein said adjuvant is an oil-in-water emulsion or an aluminium salt.

32. An immunogenic composition comprising:
    a self-replicating RNA molecule that encodes an HCMV membrane protein complex; and
    the HCMV membrane protein complex of claim 18 or claim 19.

33. A kit comprising:
    a priming composition comprising a self-replicating RNA molecule that encodes an HCMV membrane protein complex; and
    a boosting composition comprising the HCMV membrane protein complex of claim 18 or claim 19.

34. A recombinant nucleic acid molecule which encodes gL, gH that lacks a transmembrane domain, and at least one additional HCMV glycoprotein, wherein said recombinant nucleic acid:
    (a) is not a self-replicating RNA molecule;
    (b) is not an alphavirus replicon;
    (c) does not encode any alphavirus nonstructural proteins, such as NSP1, NSP2, NSP3 and NSP4;
    (d) does not contain: an Internal Ribosomal Entry Site (IRES), such as EMCV or EV71; and/or
    (e) does not contain a viral 2A site, such as FMDV.

35. The recombinant nucleic acid molecule of claim 34, wherein said recombinant nucleic acid molecule encodes:
gL, gH that lacks a transmembrane domain, pUL128, pUL130 and pUL131A; or
gL, gH that lacks a transmembrane domain and gO.

36. A plurality of recombinant nucleic acids, wherein said plurality of recombinant nucleic acids encode gL, gH that lacks a transmembrane domain, and at least one additional HCMV glycoprotein, wherein one or more or all of said plurality of recombinant nucleic acids:
(a) is not a self-replicating RNA molecule;
(b) is not an alphavirus replicon;
(c) does not encode any alphavirus nonstructural proteins, such as NSP1, NSP2, NSP3 and NSP4;
(d) does not contain: an Internal Ribosomal Entry Site (IRES), such as EMCV or EV71; and/or
(e) does not contain a viral 2A site, such as FMDV.

37. The plurality of recombinant nucleic acids of claim 36 comprising:
a first construct encoding gH that lacks a transmembrane domain and gL; and
a second construct encoding one additional HCMV glycoprotein.

38. The plurality of recombinant nucleic acids of claim 37, wherein said second construct encodes:
pUL128, pUL130 and pUL131A; or
gO.

39. The plurality of recombinant nucleic acids of claim 36 comprising:
a first recombinant nucleic acid molecule which encodes gL;
a second recombinant nucleic acid molecule which encodes a fragment of gH that lacks a transmembrane domain; and
one or more third recombinant nucleic acid molecules which encode one or more additional HCMV proteins.

40. The recombinant nucleic acid molecule of claim 34 or claim 35, or the plurality of recombinant nucleic acids molecules of any one of claims 36-39, wherein:
(a) said nucleic acid molecule which encodes gH is 89%, 90%, 91%, 92%, 93%, 94%, 95%, 96%, 97%, 98% or 99% identical to the sequence recited in SEQ ID NO: 24;
(b) said nucleic acid molecule which encodes gL is 89%, 90%, 91%, 92%, 93%, 94%, 95%, 96%, 97%, 98% or 99% identical to the sequence recited in SEQ ID NO: 25;
(c) said nucleic acid molecule which encodes pUL128 is 74%, 76%, 78%, 80%, 82%, 84%, 86%, 88%, 90%, 91%, 92%, 93%, 94%, 95%, 96%, 97%, 98% or 99% identical to the sequence recited in SEQ ID NO: 26;
(d) said nucleic acid molecule which encodes pUL130 is 74%, 76%, 78%, 80%, 82%, 84%, 86%, 88%, 90%, 91%, 92%, 93%, 94%, 95%, 96%, 97%, 98% or 99% identical to the sequence recited in SEQ ID NO: 27; and/or
(e) said nucleic acid molecule which encodes pUL131A is 74%, 76%, 78%, 80%, 82%, 84%, 86%, 88%, 90%, 91%, 92%, 93%, 94%, 95%, 96%, 97%, 98% or 99% identical to the sequence recited in SEQ ID NO: 28.

41. A cell that expresses the recombinant nucleic acid or plurality of recombinant nucleic acids of any one of claims 34-40, wherein said cell does not comprise the full HCMV genome.

42. The cell of claim 41, wherein said cell is stably transformed with said recombinant nucleic acid or plurality of recombinant nucleic acids.

43. The cell of claim 41 or claim 42, wherein said cell is a mammalian cell.

44. A cell comprising gH, gL and at least one additional HCMV glycoprotein, wherein said cell does not:
(a) contain the HCMV genome;
(b) produce HCMV virions;
(c) contain self-replicating RNA molecules encoding said gH, gL and at least one additional HCMV glycoprotein; and/or
(d) contain alphavirus replicons.

45. A process for producing an isolated or a purified HCMV membrane protein complex comprising gH, gL and at least one additional HCMV glycoprotein, wherein said process involves growing the cell of any one of claims 41-44 in growth medium.

46. The process of claim 45, wherein said HCMV membrane protein complex is secreted into said growth medium.

47. The process of claim 46, wherein said HCMV membrane protein complex accumulates to a concentration of >0.8 mg, >0.85 mg, >0.88 mg, >0.9 mg, >0.95 mg, >1 mg, >1.5 mg, >2 mg, >2.5 mg, >3 mg, >3.5 mg, >4 mg, >4.5 mg, >5 mg of complex per liter of growth medium.

48. The process of any one of claims 45-47, wherein said process comprises purifying said HCMV membrane protein complex from said growth medium.

49. A method for raising antibodies using the HCMV membrane protein complex of claim 18 or claim 19.

50. The method of claim 49, wherein said antibodies are human or humanised.

51. The method of claim 49 or 50, wherein said antibodies are neutralizing antibodies.

52. An antibody produced by the method of any one of claims 49-51.

53. An antibody produced by the method of any one of claims 49-52, wherein said antibody binds to the isolated HCMV membrane protein complexes of any preceding claim, but not isolated gH, gL, gO, pUL128, pUL130 or pUL131A.

54. The antibody of claim 52 or claim 53, wherein said antibody is for use in a diagnostic assay.

55. The antibody of any one of claims 52-54, wherein said antibody is labelled directly or indirectly.

56. The antibody of any one of claims 52-53, wherein said antibody is for use in therapy.

58. An RNA prime-protein boost regimen comprising:
performing one or more priming immunization(s) with RNA that encodes one or more of the protein components of an HCMV membrane protein complex, wherein said HCMV membrane protein complex comprises gH, gL and at least one additional HCMV glycoprotein;
performing one or more boosting immunization(s) later with a purified HCMV membrane protein complex, wherein said purified HCMV membrane protein complex comprises gH, gL and at least one additional HCMV glycoprotein.

EXAMPLES

Example 1

Immunogenicity of Replicons Expressing Pentameric Complex

In WO 2012/051211, an alphavirus replicon vector expressing all five proteins of the pentameric complex (gH, gL, pUL128, pUL130 and pUL131A) from a single construct was produced. The RNAs expressed by this vector were either packaged into VRPs or formulated for RNA vaccination either by complexing replicons with CNEs or by encapsulating replicons in LNPs. The VRPs and formulated RNAs were used to immunize BALB/c mice at three-week intervals. Sera from immunized mice were used in microneutralization assays to block infection of epithelial cells with HCMV TB40 (in the absence of complement). The HCMV TB40 strain is similar to clinical strains and infects endothelial and epithelial cells, natural target cells of HCMV in vivo (17). Microneutralization assay data demonstrated that replicons expressing the pentameric complex elicited more potently neutralizing antibodies than replicons expressing gH/gL. Microneutralisation data also showed that antibodies elicited by RNA expressing pentameric complex are able to neutralize HCMV infection in epithelial cells (because they target the pentameric complex), but not in fibroblasts (in which infection does not require the pentameric complex), thus demonstrating that RNA expressing the pentameric complex elicits antibodies that specifically target the intact pentameric complex rather than a gH/gL dimer. This work demonstrates that antibodies can be raised against the pentameric complex, and these antibodies are capable of neutralizing HCMV infection.

Example 2

Constructs for Stable Expression of the Pentameric Complex in Mammalian Cells

Figure 1:
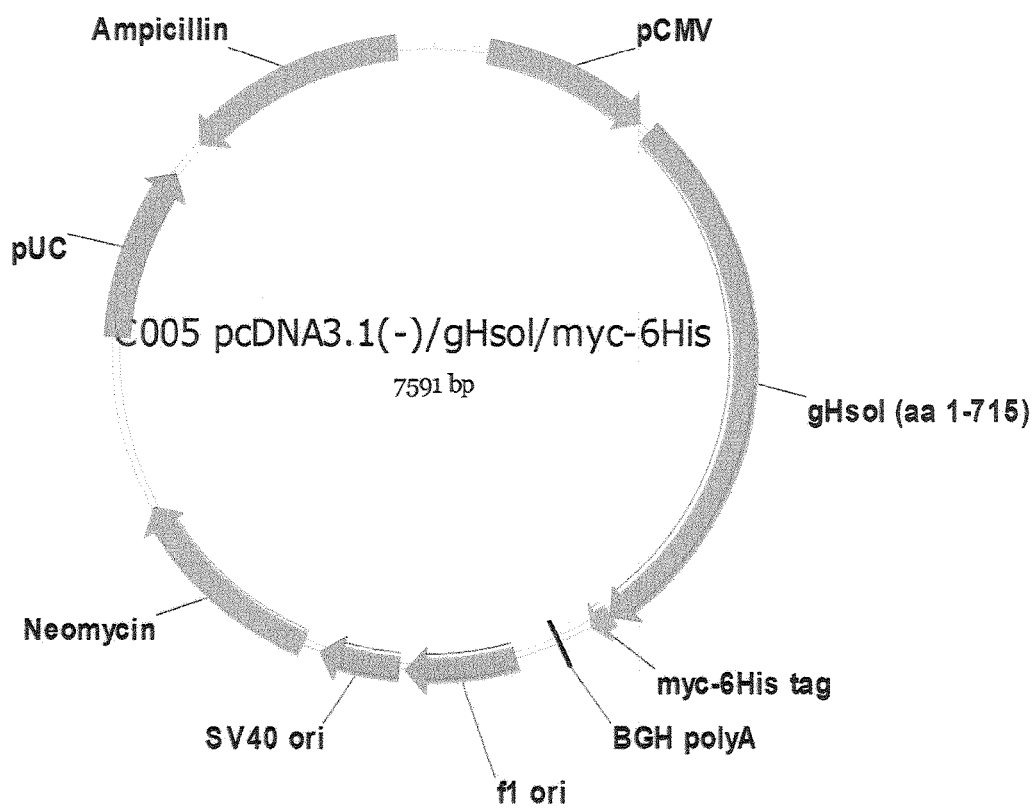
FIG. 1 shows the plasmid map of the 7591 bp construct used for the expression of His-tagged, soluble gH in mammalian cells. The nucleotide sequence of this construct is given as SEQ ID NO: 23. The construct comprises a CMV promoter, a gene which encodes SEQ ID NO: 4 (the gH soluble protein, which consists of amino acid residues 1-715 of the full-length gH protein) fused to a myc-polyhistidine tag, bovine growth hormone (BGH) polyadenylation (bgh- PolyA) signal termination sequence, F1 phage origin of replication, SV40 origin of replication, Neomycin resistance gene, pUC subgenomic promoter and an ampicillin resistance gene.
Figure 2:
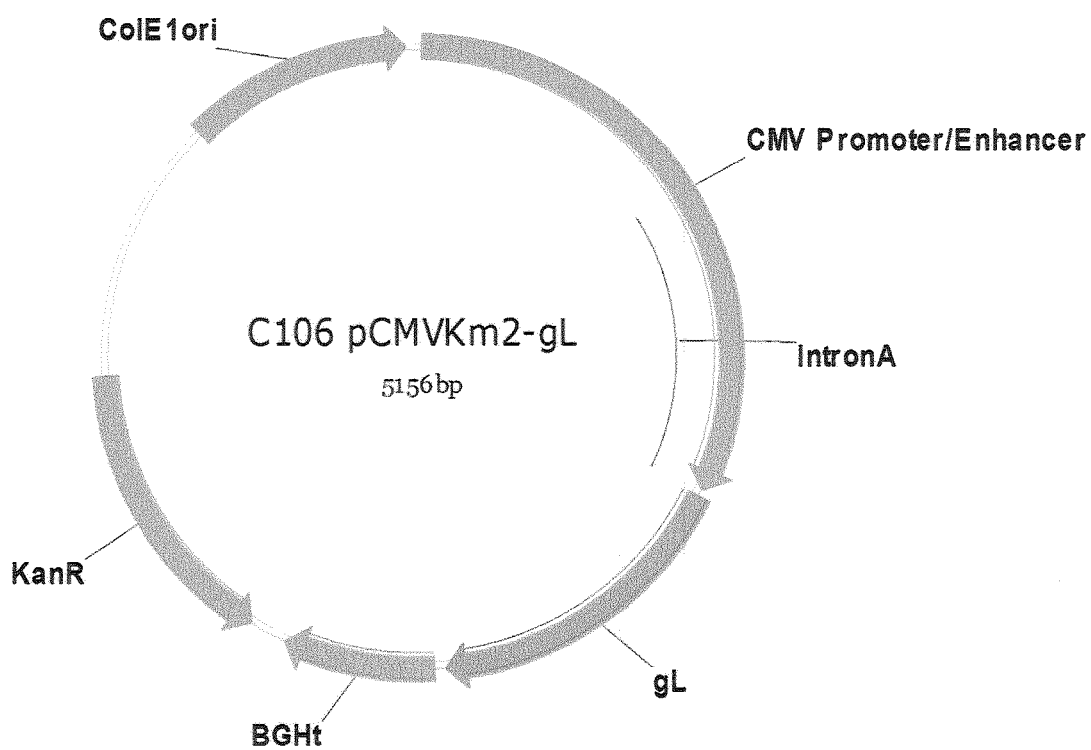
FIG. 2 shows the plasmid map of the 5156 bp construct used for the expression of gL in mammalian cells. The nucleotide sequence of this construct is given as SEQ ID NO: 24. The construct comprises a CMV promoter/enhancer which contains intronA, a gene which encodes SEQ ID NO: 7 (gL), bovine growth hormone (BGH) polyadenylation (bgh-PolyA) signal termination sequence, a kanamycin resistance gene and the ColE1 origin of replication.
Figure 3:
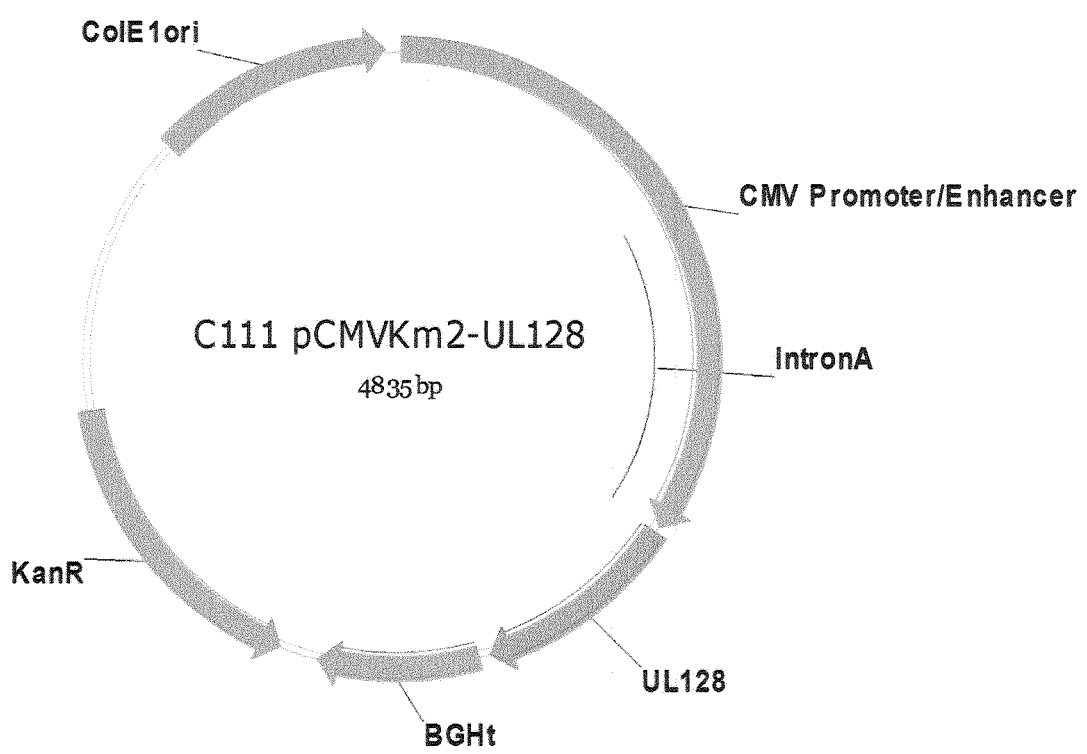
FIG. 3 shows the plasmid map of the 4835 bp construct used for the expression of UL128 in mammalian cells. The nucleotide sequence of this construct is given as SEQ ID NO: 25. The construct comprises a CMV promoter/enhancer which contains intronA, the UL128 gene, bovine growth hormone (BGH) polyadenylation (bgh-PolyA) signal termination sequence, a kanamycin resistance gene and the ColE1 origin of replication.
Figure 4:
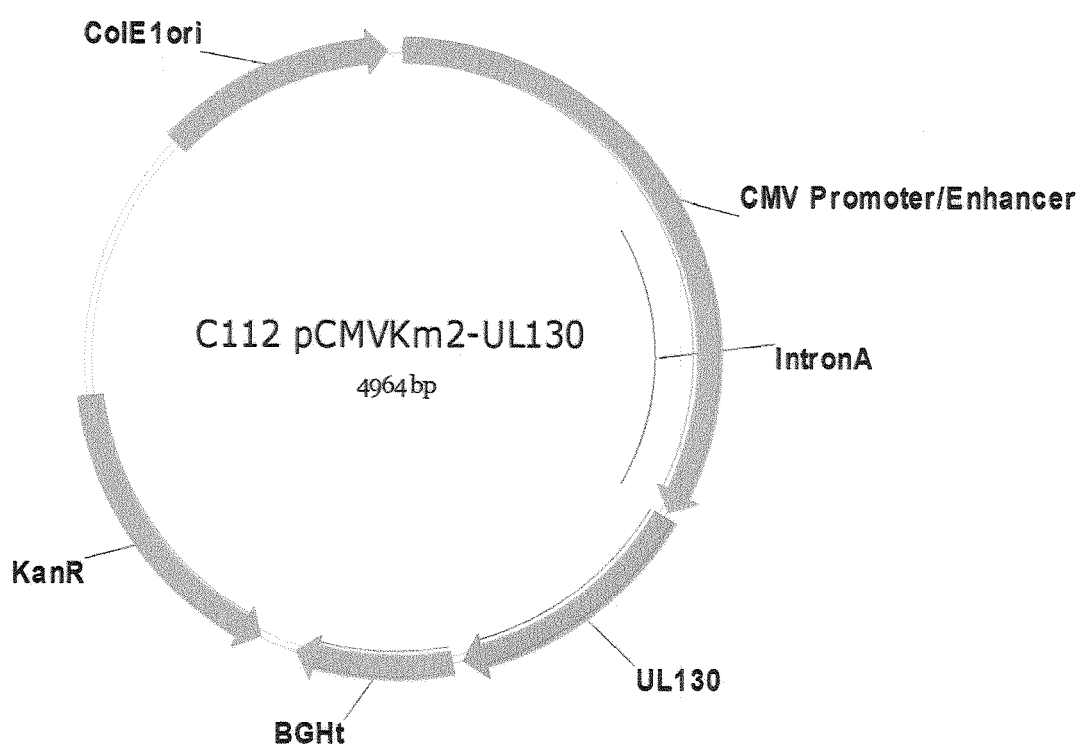
FIG. 4 shows the plasmid map of the 4964 bp construct used for the expression of UL130 in mammalian cells. The nucleotide sequence of this construct is given as SEQ ID NO: 26. The construct comprises a CMV promoter/enhancer which contains intronA, the UL130 gene, bovine growth hormone (BGH) polyadenylation (bgh-PolyA) signal termination sequence, a kanamycin resistance gene and the ColE1 origin of replication.
Figure 5:
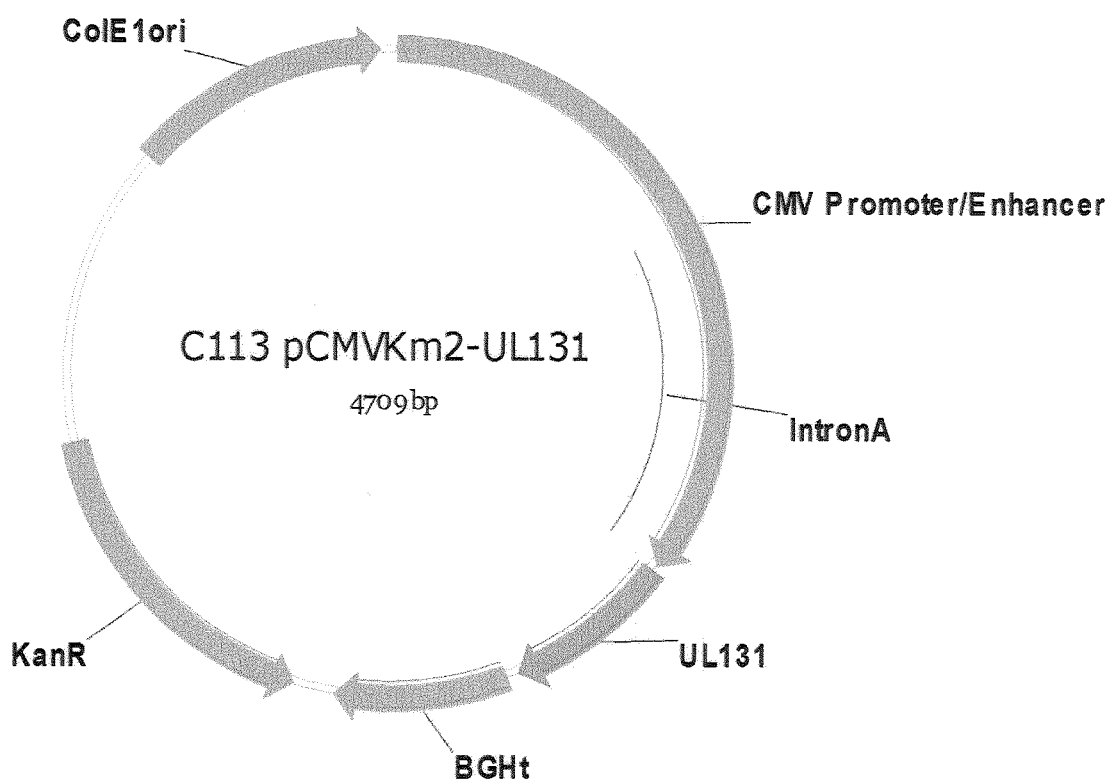
FIG. 5 shows the plasmid map of the 4709 bp construct used for the expression of UL131A in mammalian cells. The nucleotide sequence of this construct is given as SEQ ID NO: 27. The construct comprises a CMV promoter/enhancer which contains intronA, the UL131A gene, bovine growth hormone (BGH) polyadenylation (bgh-PolyA) signal termination sequence, a kanamycin resistance gene and the ColE1 origin of replication.
Figure 6:
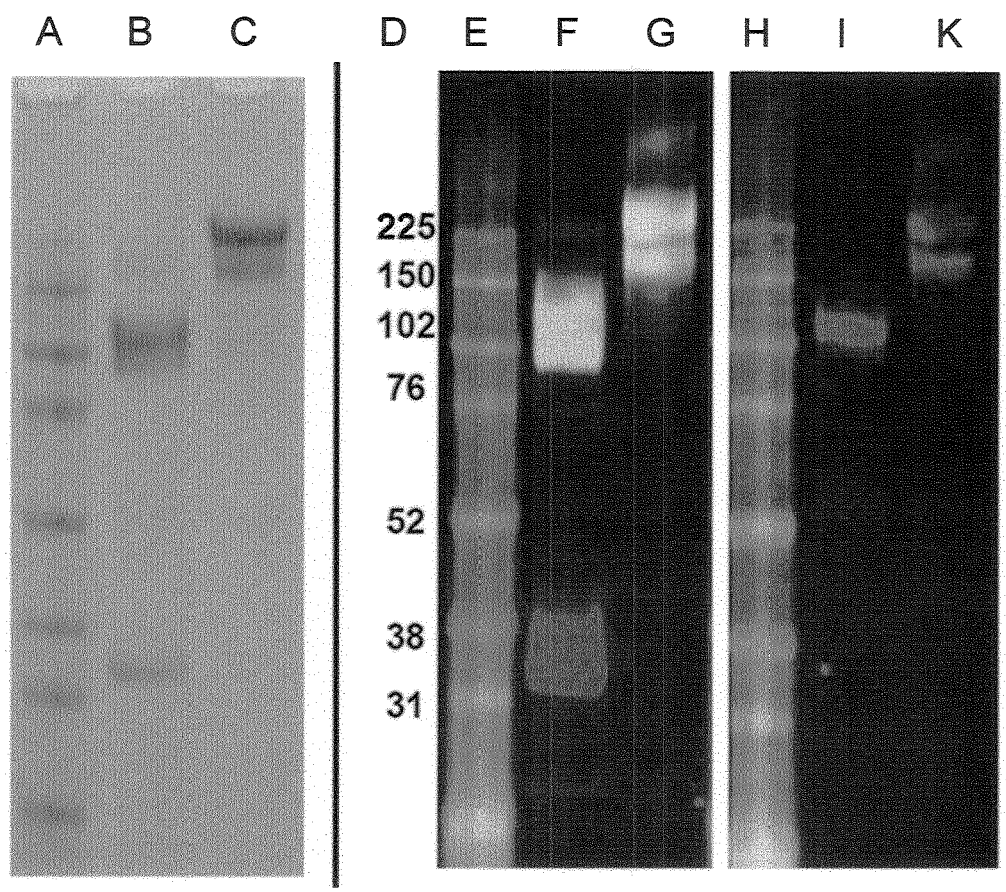
FIG. 6 lanes A-C correspond to a silver-stained SDS-PAGE, whereas lanes E-K correspond to Western blot analysis. In lanes E-G, green=Anti-APPtag (gH) and red=Anti-gL, whereas in lanes H-K, red=anti-6His (gO). The ladder is shown in lanes A, E and H. Lanes B, F and I correspond to samples that have been briefly heated to near boiling in the presence of dithiothreitol (DTT), whereas lanes C, G and K correspond to samples that have not been subjected to heat or DTT.

Five nucleic acid constructs were produced to enable to expression and purification of the pentameric complex in mammalian cells. Previous attempts to purify the pentameric complex when constructs including the gene encoding the full-length gH protein were unsuccessful. In an attempt to overcome this problem, the inventors produced constructs that encode only the ectodomain of gH (gHecto) with a C-terminal myc-(His)6 tag (SEQ ID NO: 6) rather than the full-length sequence. The following five constructs were used to produce the pentameric complex: a construct encoding SEQ ID NO: 6 (FIG. 1 and SEQ ID NO: 23), a construct encoding full-length gL (FIG. 2 and SEQ ID NO: 24), a construct encoding full-length pUL128 (FIG. 3 and SEQ ID NO: 25), a construct encoding full-length pUL130 (FIG. 4 and SEQ ID NO: 26) and a construct encoding full-length pUL131A (FIG. 5 and SEQ ID NO: 27).

Example 3

Protocol for Transfection and Expression of Protein Complexes in 293-6E Cells

Materials
Mammlian 293-6E cells (Gibco FreeStyle 293 Expression Medium; Opti-MEM and Polyethylenimine Linear (PEI), MW 25,000.
Preparation of Cells
293-6E cells were maintained in serum-free 293 Expression Medium. Once the cells are doubling every 24 hours and at more than 90% viability, the cells were diluted to a density of $1 \times 10^6/1$ mL media.
Transfection
DNA corresponding to each construct was diluted in Opti-MEM using a volume of Opti-MEM that is 2.5% of the volume of cell culture to be transfected. DNA constructs were combined in an appropriate ratio such that total DNA was equal to 1 µg/1 mL culture volume. For example, for the stable expression of the pentameric complex using 1 L cell culture, 200 µg of each of SEQ ID NOs: 23-27 were added to 25 mL Opti-MEM.
PEI was diluted in Opti-MEM using a volume of Opti-MEM that is 2.5% the volume of cell culture to be transfected. The diluted PEI was incubated for 5 min at room temperature with occasional swirling to mix. 3 µg PEI was used per 1 mL culture (e.g., for 1 L cell culture 3 mg PEI was diluted in 25 mL Opti-MEM).
The DNA mix was added to the PEI mix (so that 1 µg total DNA+3 µg PEI were used per 1 mL culture), swirled and incubated at room temperature for 30 min. The DNA-PEI mix was added to cells by gradually adding mixture and swirling cells occasionally such that mixture was added evenly to culture. The cells were then immediately returned to the original growth conditions.
Expression and Harvest
Three days post-transfection, the media was harvested by spinning the cells down at 2,000 rpm. The media was then concentrated approximately 10× and diafiltered into buffer containing 300 mM NaCl, 25 mM Tris pH 7.5. Finally, the dialyzed media was frozen at −80° C. Fresh media were added to the culture and three more days later the media was harvested and concentrated/diafiltered as above.

Example 4

Protocol for Purification of the HCMV Complexes

Materials:
GE AKTAxpress; Qiagen Ni-NTA Superflow Cartridges, 5 ml; 96 Well Clear V-Bottom 2 mL Polypropylene Block; Buffer A (=binding buffer) 50 mM Tris-HCl pH 7.5, 300 mM NaCl, 5 mM Imidazole; Buffer B (=elution buffer) 50 mM Tris-HCl pH 7.5, 300 mM NaCl, 1 M Imidazole; SEC buffer (=for buffer exchange and size exclusion chromatography); 2×500 ml 0.5 M NaOH solution for system cleaning; Invitrogen NuPAGE® Novex 4-12% Bis-Tris Gel 1.0 mm, 12 well; NuPAGE® LDS Sample Buffer (4×) and NuPAGE® Sample Reducing Agent (10×).
Procedures
Buffers were prepared with endotoxin-free stock solutions and filtered Milli-Q water.
The medium to be purified was thawed in a warm water bath. Meanwhile AKTAxpress was cleaned with 0.5M NaOH, to get rid of possible endotoxin contamination as well as residual protein/media, and then rinsed with filtered endotoxin-free Milli-Q water.
The Ni-NTA superflow cartridge was connected to the AKTAxpress system, and the water and buffers A and B were set in place. The program "Ni-NTA prep" was then started in order to flush the system with buffers, wash away ethanol in the column, and run buffer A through the column to equilibrate it.
The fraction collecting 96-well was prepared by putting 3.5 µl 500 mM EDTA solution in each well. The loading sample was also prepared immediately before loading. When the medium had thawed, 1/500 volume of 2.5M Imidazole stock was added, and mixed gently. The loading sample was then set in place.
The purification program was then started. This program performed the following steps: sample loaded onto the column; washed away the unbound compounds with buffer A until the baseline settles; washed away non-specifically binding compounds with 15 column volumes of 2.5% buffer B (=30 mM Imidazole); elute the HCMV protein complex with 10 column volumes of 25% buffer B (=254 mM Imidazole); and finally washed the column with 5 column volumes of 100% buffer B (=1 M Imidazole). The sample loading rate was 2.5 ml/min, whereas the wash and elution rate was 5 mL/min. The flow through in whole and 1.75 ml each of fractions from wash and elution were collected).
Six or seven fractions from the 250 mM Imidazole elution peak were selected to be analysed by SDS-PAGE. The four or five fractions which had the highest amount of protein according to the SDS-PAGE gel were pooled together, and dialyzed against 2 L SEC buffer for 1 h at RT, twice. The dialysate was recovered and the concentration measured using the BCA method. The presence of all components of the complex in the purified protein pool was verified by Western blot.
In order to increase the purity of some samples, size exclusion chromatography (SEC) was performed. On a Superdex 200 10/300 GL (GE Healthcare, 17-5175-01) equilibrated with SEC buffer for more than two column volumes. The dialyzed pool was loaded one column volume of buffer was run through the column, and 1 mL fractions were collected. SDS-PAGE was performed to determine which fractions to pool and keep.

Example 5

Expression, Purification and Characterization of the Trimeric gH/gL/gO Complex

The following three constructs were produced: gH ectodomain with C-terminal APP tag, full-length gL and full-length gO with a C-terminal (His)6 tag. These three constructs were co-expressed in HEK 293 cells according to the method described in Example 3. The purification method of Example 4, involving $Ni^{2+}$ affinity chromatography, was performed.

The purified samples were then subjected to SDS-PAGE, followed by Western blot analysis using anti-APPtag (gH), anti-gL and anti-6His (gO) antibodies. These three antibodies bound to different proteins under reducing conditions (+heat, +DTT), but all bound to a single complex in non-reducing conditions (−heat, −DTT). These results demonstrate the successful purification of gH/gL/gO as a trimeric complex. Approximately 0.5 mg/L media of the complex was purified from HEK 293 cells. SEC increased the purity of the gH/gL/gO complex.

Example 6

Expression and Purification of the Pentameric Complex

HEK293 cells were co-transfected with the five constructs described in Example 2 according to the method described in Example 3, the media were harvested 3 and 6 days post transfection, and the expressed protein was purified by Ni-NTA chromatography according to the method of Example 4.

Figure 7:
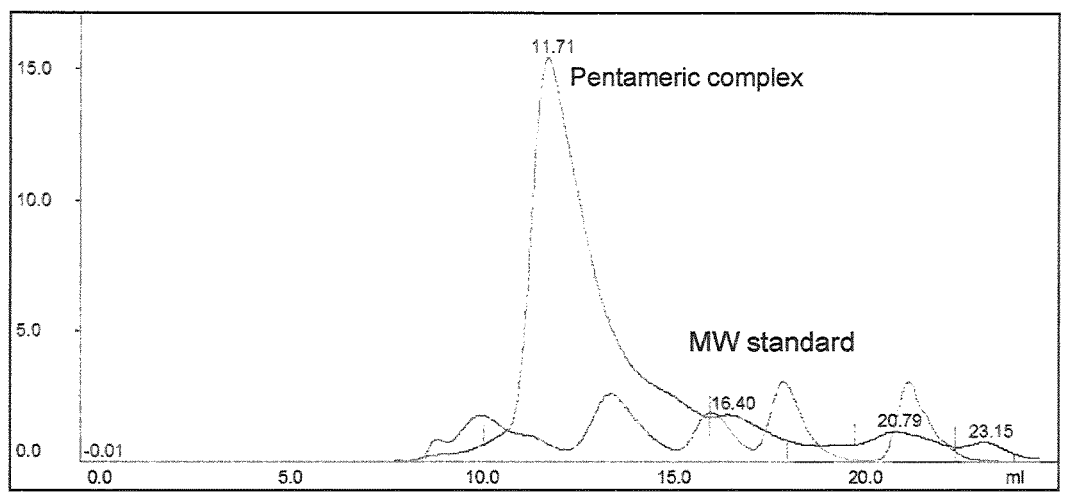
FIG. 7 shows a size exclusion chromatogram. All five proteins were eluted as a single peak, thus demonstrating the presence of an intact pentameric complex.

A single peak in the size exclusion chromatogram for the purified pentameric complex (FIG. 7) indicated that an intact, monomeric complex was successfully purified. To assess whether all five members of the pentameric complex: gHecto-His, gL, pUL128, pUL130 and pUL131A were present within the purified complex, SDS-PAGE and Western blot analysis was performed.

Example 7

Western Blotting of HCMV Pentameric Complex

Materials:
BioRad Trans-Blot SD Semi-Dry Electrophoretic Transfer Cell; Invitrogen Nitrocellulose membranes, 0.2 μm pore; NuPAGE® Transfer Buffer (20×); Methanol; Odyssey® Blocking Buffer; DPBS; 10×PBS; Primary antibodies: Mouse anti-His tag, rabbit anti-gL 27-46, mouse anti-pUL128 4B10, mouse anti-UL130 3E3, and rabbit anti-UL131A 90-136; secondary antibodies: IRDye 800CW Goat anti-Rabbit IgG (H+L), IRDye 680LT Goat anti-Mouse IgG (H+L).

Procedures
Three sets of antibodies were used, one for the detection of gHecto-His/gL, one for the detection of pUL128/pUL131A, and one for the detection of pUL130.

9 μl of the protein was mixed with 3 μl of LDS sample buffer/reducing agent mixture (9:1) and boiled at 100° C. for 3 minutes. The boiled samples were loaded on the wells and run at 200 V for 35 minutes. The protein was then transferred to a 0.2 m nitrocellulose membrane using the Trans-Blot SD Semi-Dry Electrophoretic Transfer Cell at 20 V for 35 minutes. The membrane was blocked with blocking buffer at room temperature for 30 minutes. The membranes were incubated with primary antibody solutions at RT for 1 hr. Primary antibody solutions consisted of: (A) 1:10000 dilution of anti-His tag and 1:5000 dilution of anti-gL, (B) 1:500 dilution of anti-pUL128 and 1:1000 dilution of anti-UL131A, and (C) 1:500 dilution of anti-UL130, all diluted in 1:1 mixture of the blocking buffer and DPBS. The membranes were rinsed three times with PBS+0.1% Tween at RT, and then incubated with secondary antibody solutions at RT for 1 hr. For membranes (A) and (B), 1:25000 dilution each of anti-mouse and anti-rabbit antibodies in a 1:1 mixture with the blocking buffer and DPBS was used. For membrane (C), 1:25000 dilution of anti-mouse antibodies were used only. The membranes were rinsed three times with PBS+0.1% Tween at RT, and then rinsed with DPBS once at RT. The membrane was scanned with Odyssey Infrared Imaging System (Li-Cor 9201) and analyzed using Odyssey software version 2.1.12.

Figure 8:
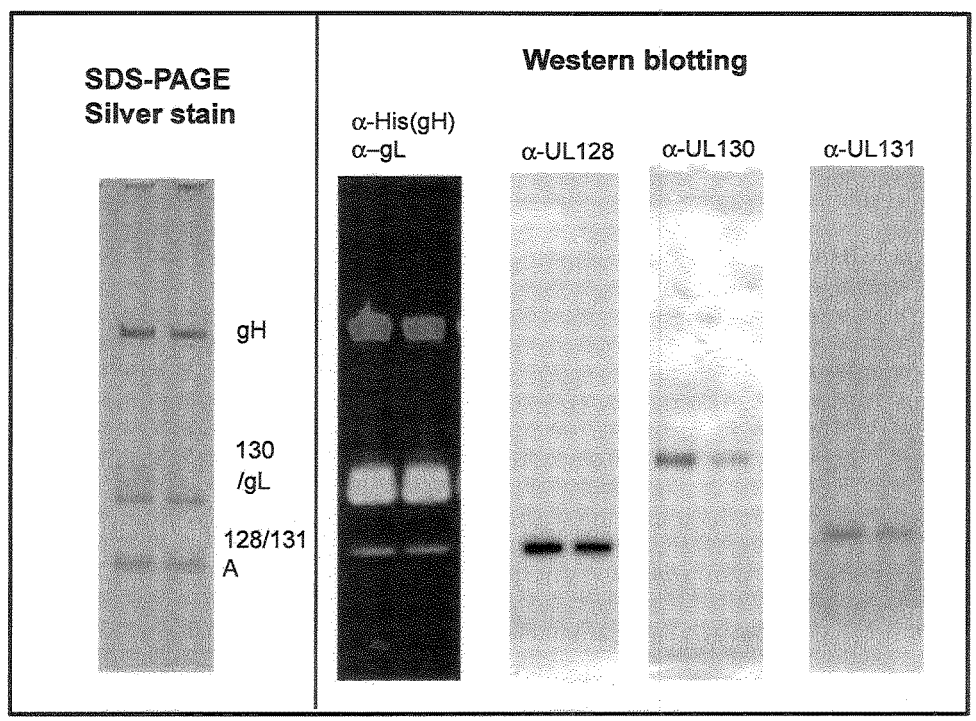
FIG. 8 shows SDS-PAGE and Western blot analysis.

All five members of the pentameric complex: gHecto-His, gL, pUL128, pUL130 and pUL131A were present within the purified complex, were identified by SDS-PAGE and Western blot analysis (FIG. 8), thus confirming the successful purification of the pentameric complex.

gHecto-His, gL and pUL128 co-migrate in an SDS Bistris gel without heat nor DTT, but the association of pUL128 and gH/gL completely disappears in the presence of DTT (data not shown), thus demonstrating that pUL128 associates with gH/gL through a disulfide bond. pUL130/pUL131A does not co-migrate with gH/gL/pUL128, indicating that it is incorporated into the pentameric complex by non-covalent bonds.

The most dominant band on the gels was near the gH/gL complex position with non-reducing, non-boiling conditions, and was thus thought to correspond to the HCMV pentameric complex. The purity was estimated to be 90%, by mass. With SEC purification the purity increased to nearly 100%. Approximately 0.6 mg of pentameric complex per liter of media could be purified by Ni-NTA purification.

Example 8

Recombinant Pentameric Complex Binds to Conformation Dependent Neutralizing Antibodies A panel of human neutralizing antibodies (HumAb) were isolated from memory B cells of seropositve individuals. Direct ELISA was performed in which pentameric complex protein was immobilized on a plate and neutralizing antibodies were added in a 10-fold series dilution. The results of this ELISA are shown in Table 1. The HumAb bound to several UL proteins and gH/gL/pUL128/pUL130, which confirmed the correct conformation of the pentameric complex forms. Binding of HumAb against gH suggests that these epitopes are exposed on the recombinant complex.

TABLE 1

| HuMab | 10P3 | 5A2 | 4I22 | 8J16 | 7I13 | 15D8 | 8I21 | 3G16 | 11B12 | cytotect | Chick. Lyso. |
|---|---|---|---|---|---|---|---|---|---|---|---|
| epitope | pUL130/ pUL131A site 3 | pUL130/ pUL131 A site 2 | pUL130/ pUL131 A site 1 | pUL128/ pUL130/ pUL131A site 1 | pUL128/ pUL130/ pUL131 A site 2 | pUL128 | gH/gL/ pUL128/ pUL130 | gH/gL pUL128/ pUL130 | gH/gL site B | | |
| KD (nM) | 0.17 | 0.1 | 0.1 | 0.13 | 0.11 | 0.33 | 0.57 | 0.06 | 0.21 | 9.8 | — |

Example 9

Figure 9:
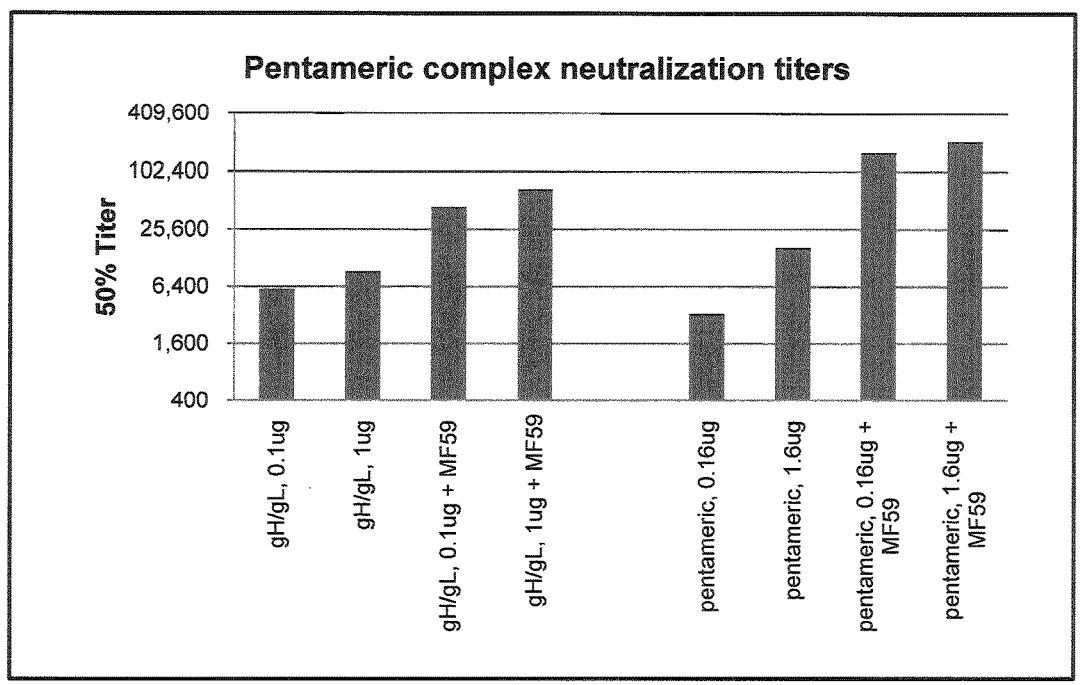
FIG. 9 shows a comparison between the neutralization titers elicited by gH/gL either alone or formulated with MF59 versus those elicited by the pentameric complex either alone or formulated with MF59. Purified pentameric complex formulated with MF59 elicited higher neutralizing titers than the unformulated protein.
Figure 10:
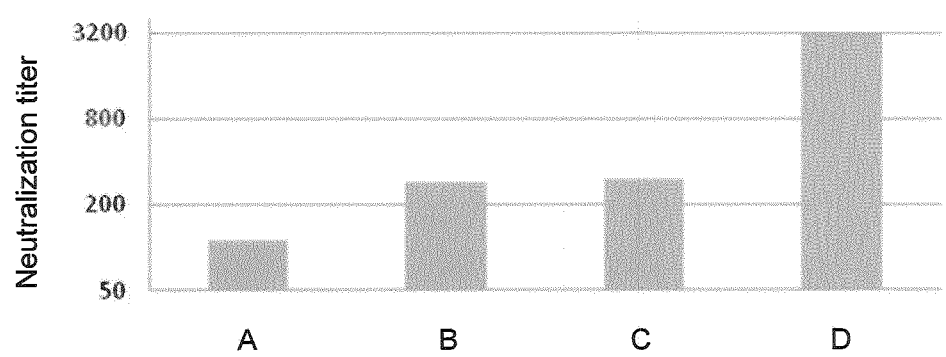
FIG. 10 shows the neutralization titers elicited by pentameric complex alone (A) and pentameric complex formulated with MF59 (B), aluminium oxyhydroxide (C) and aluminium hydroxide to which a TLR7 agonist is adsorbed (D).

The Pentameric Complex Elicits Higher Neutralizing Titers than gH/gL 0.1/1 µg purified gH/gL and 0.16 µg/1.6 µg pentameric complex protein were formulated with or without MF59 and used for immunization of mice. The neutralizing titer of 3wp3 showed approximately a 4-fold increase for pentameric complex compared with gH/gL (which in turn elicits higher neutralizing titers compared with gB) (FIG. 9). Purified pentameric complex formulated with MF59 elicited higher neutralizing titers than the unformulated protein (FIG. 9). Formulation of the pentameric complex with aluminium hydroxide to which a TLR7 agonist is adsorbed elicits even higher neutralizing titers than formulations with aluminium oxyhydroxide and/or MF59 (FIG. 10).

Example 10

Production of Monoclonal Antibodies Using Purified gH/gL/gO as an Antigen

The purified gH/gL/gO complex is diluted to 0.4 mg/mL in 150 mM NaCl, 25 mM Tris (pH 7.5), 1 mM EDTA and frozen. The gH/gL/gO complex is thawed on the day of vaccination and 438 µl of adjuvant is added to the thawed gH/gL/gO complex and mixed well by inverting the tubes at least 10 times. The resulting composition is used within 1 hour of mixing.

Two groups of three 6-8 week-old female BALB/c mice are immunized with a composition comprising 50 µg purified gH/gL/gO, and MF59 adjuvant. Each mouse is immunized with 125 µL in each quadriceps muscle (i.e. each mouse received 250 µL) and bled from their orbital sinuses.

For each group of three mice, the immunization schedule is summarised in Table 2 below:

TABLE 2

| | | Weeks | | | |
|---|---|---|---|---|---|
| 0 | 0 | 3 | 5 | 6 | 8 |
| Procedure | Bleed 0 | Immunization 1 | Immunization 2 | Bleed 2 | Immunization 3 | Bleed 3 |

In order to purify monoclonal antibodies against gH/gL/gO, the gH/gL/gO antigen is used for primary ELISA screening and then the positive clones from the primary screening are then further screened using the gH/gL antigen.

A similar method can be employed to produce monoclonal antibodies using the purified pentameric complex as an antigen.

Example 11

A SAM™ Vaccine Prime, Protein Boost and Coadministration of RNA and Subunit Using the HCMV Pentameric Antigen Mice were immunized three times, three weeks apart with a SAM vaccine, which is a self-replicating RNA as described herein, encoding the HCMV pentameric complex, purified pentameric subunit adjuvanted with MF59, different sequences of SAM vaccine followed by subunit in MF59, or a combination of the two (Table 3). The SAM vaccine was encapsulated in synthetic LNPs for non-viral delivery. A group of control mice did not receive any vaccine.

TABLE 3

| Group | No. Mice | No. Doses | Antigen | Formulation | Dose |
|---|---|---|---|---|---|
| 1 | 4 | — | 3 | — | 1 |
| 2 | 8 | 3 | SAM vaccine encoding pentameric complex (Penta SAM vaccine) | Lipid nanoparticle (LNP) | 1 microgram |
| 3 | 8 | 3 | Purified pentameric complex (Penta subunit) | MF59 | 1 microgram |
| 4 | 8 | 3 | 1st Penta SAM vaccine 2nd and 3rd Penta subunit | LNP MF59 | 1 microgram |
| 5 | 8 | 3 | 1st and 2nd Penta SAM vaccine 3rd Penta subunit | LNP MF59 | 1 microgram |
| 6 | 8 | 3 | Penta SAM + Penta subunit (mixed) | LNP | 1 microgram + 1 microgram |

Sera were harvested three weeks after each immunization and used for ELISA to determine binding antibody titers, using the same purified antigen in the assay as in the subunit vaccine. The sera were also used for HCMV microneutralization assay using TB40 or VR1814 infection of ARPE-19 epithelial cells. Three or four weeks after the third immunization, spleens were extracted from sacrificed mice. Spleen cells were stimulated in vitro with purified protein or a pool of 15-mer peptides (overlapping by 11 amino acids) corresponding to the c-terminal half of the gH protein, stained for cytokine expression, and analyzed using flow cytometry.

Figure 11:
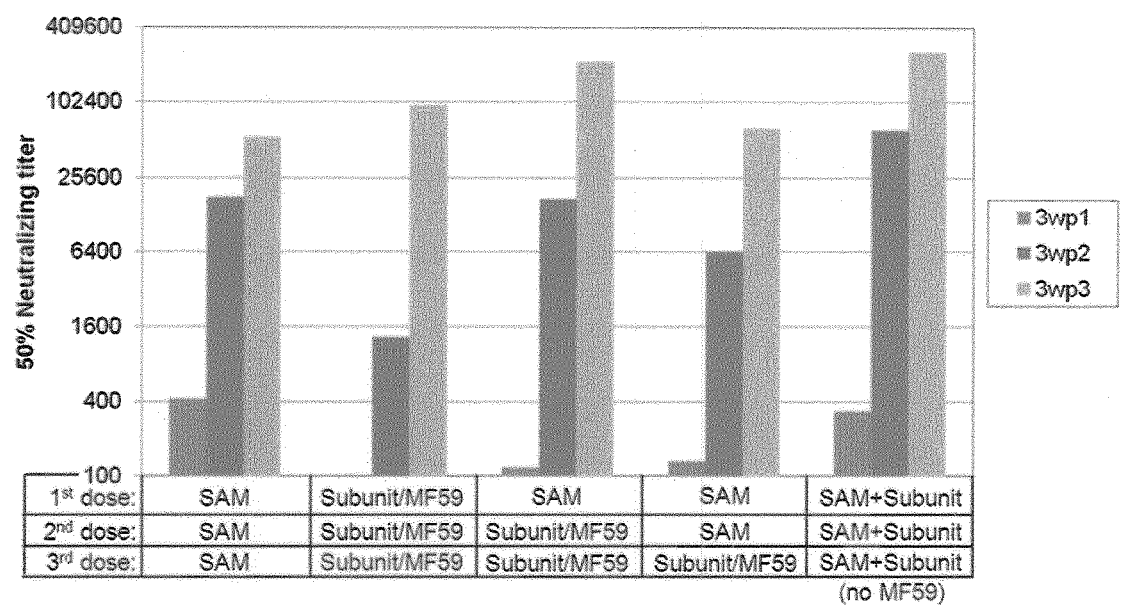
FIG. 11 is a graph showing that self amplifying RNA and subunit, alone or in combination, elicit high neutralizing antibody titers. In particular, the neutralization titers elicited by: the self amplifying RNA (self replicating RNA, encapsulated in LNPs) encoding the HCMV pentameric complex; purified pentameric subunit adjuvanted with MF59; different sequences of self amplifying RNA followed by subunit in MF59; or a combination of self amplifying RNA and subunit are shown. Self amplifying RNA and subunit dose were 1 µg, mixed dose was 1+1 µg. Neutralizing assay: VR1814 infection of ARPE-19 cells in presence of complement.

SAM vaccine and subunit/MF59 alone elicited potently neutralizing antibody responses after three doses (FIG. 11). The pentameric subunit in MF59 did not respond as well as pentameric SAM vaccine to the first and second dose of vaccine, but titers elicited by subunit/MF59 surpassed titers elicited by SAM vaccine after the third dose. One SAM vaccine prime followed by a single dose of subunit/MF59 elicited stronger neutralizing responses than two doses of subunit/MF59, but was equal to SAM alone. A second subunit/MF59 boost administered to these animals raised neutralizing responses to a level that exceeded those seen after three doses of subunit/MF59 or SAM vaccine. Two doses of SAM vaccine followed by a single dose of subunit/MF59 did not appear to benefit neutralizing responses compared to either subunit/MF or SAM vaccine alone. Mixing SAM vaccine with subunit, without MF59, elicited a strong response after the first dose, similar to RNA alone, and elicited strong neutralizing titers after two and three doses.

Figure 12:
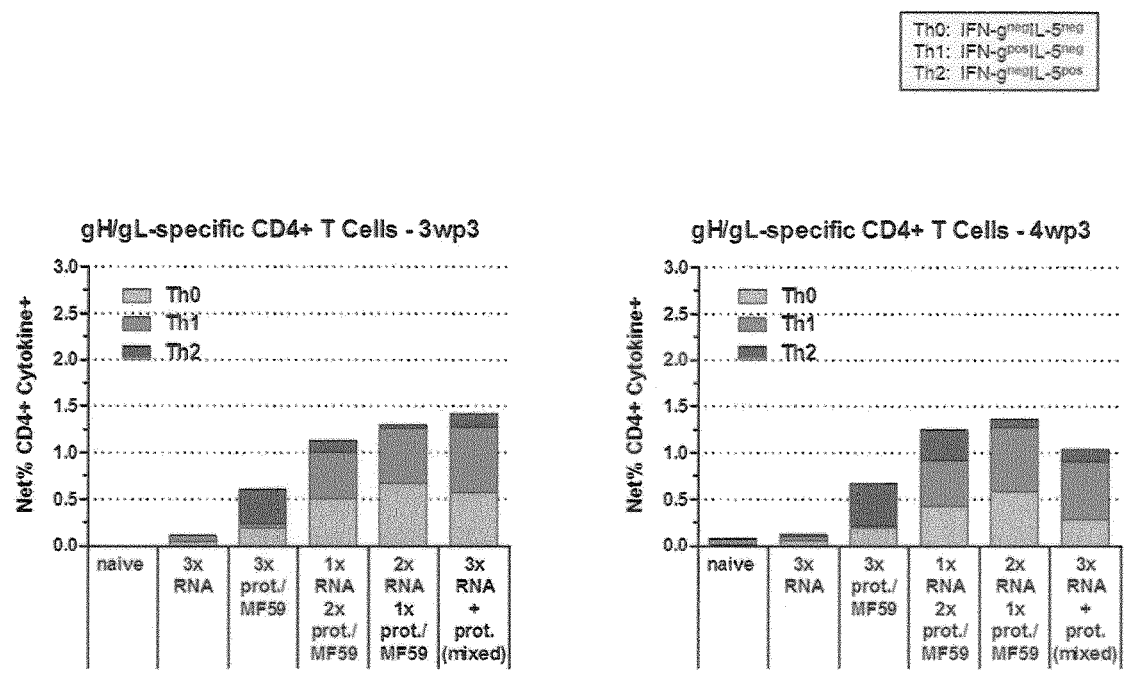
FIG. 12 are graphs showing the CD4+ T cell responses (in terms of the net % of CD4+ T cells, and the % of Th0, Th1 and Th2 CD4) to the vaccinations using purified gH/gL and pentameric subunits at (A) 3wp3 (day 64) and (B) 4wp3 (day 71).
Figure 13:
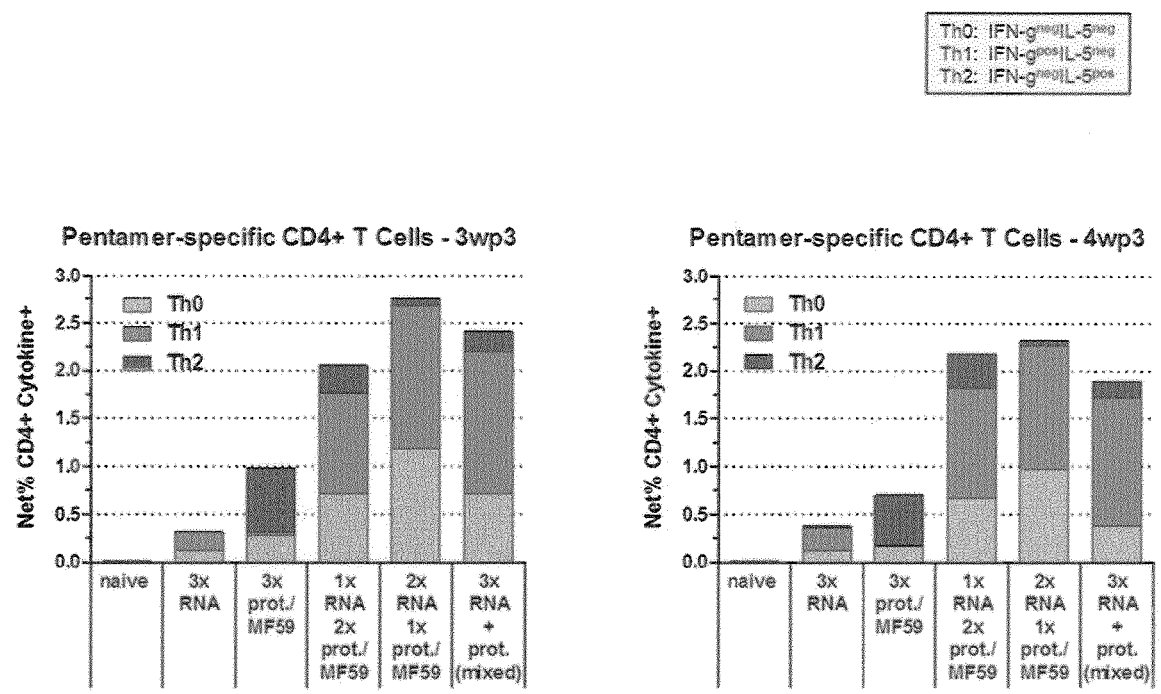
FIG. 13 are graphs showing the CD4+ T cell responses (in terms of the net % of CD4+ T cells) to the vaccinations using purified pentameric complex at (A) 3wp3 (day 64) and (B) 4wp3 (day 71).

CD4+ T cell responses to the vaccinations using purified gH/gL and pentameric subunits were analyzed. SAM vaccine prime protein boost and mixed SAM vaccine+subunit elicited more CD4+ T cells responding to gH/gL re-stimulation than SAM vaccine or subunit/MF59 alone (FIG. 12). CD4+ responses to RNA alone were insignificant, whereas responses to subunit/MF59 alone were Th2/Th0 phenotype. The phenotype of the responding cells from mice immunized combinations of SAM vaccine and subunit was primarily Th1/Th0. Similar trends were seen when re-stimulating cells with purified pentameric complex, although the responses were generally stronger (FIG. 13).

Figure 14:
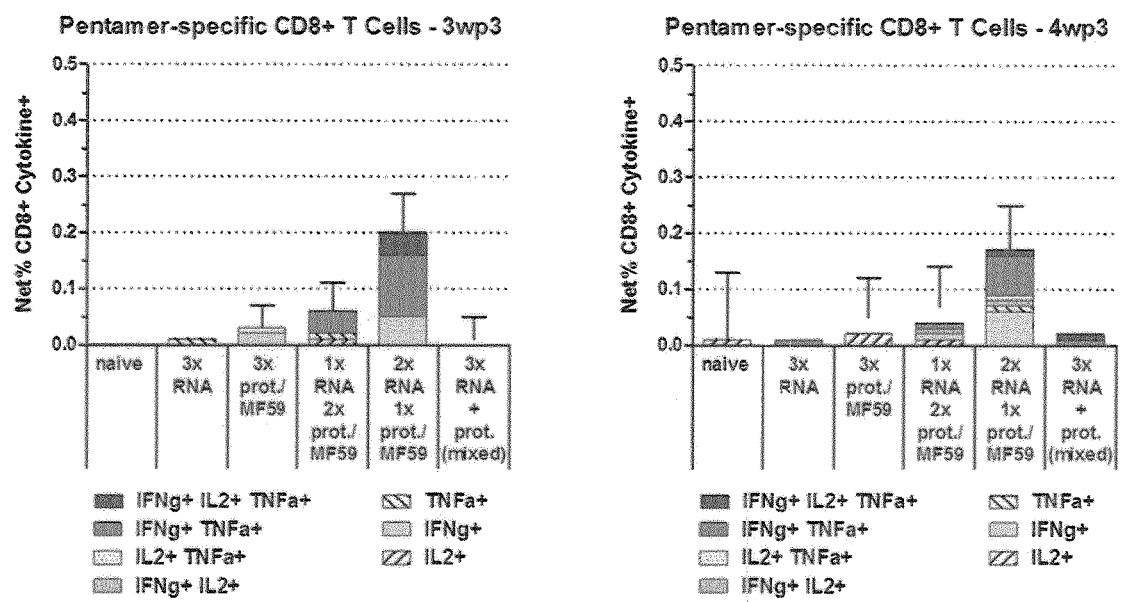
FIG. 14 are graphs showing the CD8+ T cell responses (in terms of the net % of CD8+ T cells) to the vaccinations using purified pentameric complex at (A) 3wp3 (day 64) and (B) 4wp3 (day 71).
Figure 15:
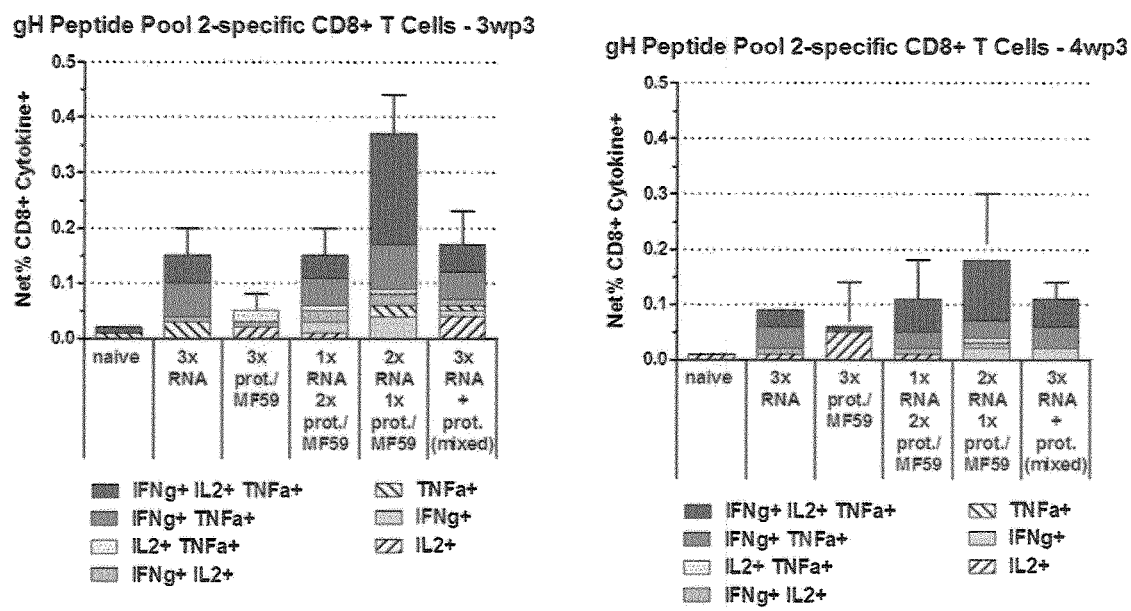
FIG. 15 are graphs showing the CD8+ T cell responses (in terms of the net % of CD8+ T cells) to the vaccinations using gH peptide pool 2 at (A) 3wp3 (day 64) and (B) 4wp3 (day 71).

CD8+ T cell responses to the vaccinations using purified pentameric subunit or a pool of peptides to gH were also analyzed. The only significant CD8 responses seen when re-stimulating with pentameric subunit was in the mice immunized with two doses of SAM vaccine followed by one dose of subunit/MF59 (FIG. 14). Cells from these animals also showed the strongest responses when re-stimulated with gH peptides (FIG. 15). Mice immunized with the SAM vaccine+subunit, with one dose of SAM vaccine followed by two doses of subunit/MF59, or with SAM vaccine alone, also showed significant responses to re-stimulation (FIG. 15).

Conclusions: One dose of SAM vaccine followed by two doses of subunit/MF59, as well as SAM vaccine+subunit, elicited higher neutralizing titers than subunit/MF59 alone. The response to SAM vaccine+subunit did not require addition of MF59 adjuvant. The largest impact of SAM vaccine prime subunit/MF59 boost was on cellular immune responses. Any combination including the SAM vaccine produced primarily a Th1/Th0 CD4+ response. Moreover, two immunizations with SAM vaccine followed by one immunization with subunit/MF59 produced the strongest CD8+ responses. This study shows that a SAM vaccine prime protein boost regimen can be optimized to produce a desired immune response, i.e. cellular or humoral.

REFERENCES

Akter, P, et al. "Two novel spliced genes in human cytomegalovirus." *Journal of General Virology* 84 (2003): 1117-1122.

Boehme, K W, M Guerrero, and T Compton. "Human cytomegalovirus envelope glycoproteins B and H are necessary for TLR2 activation in permissive cells." *Journal of Immunology* 177 (2006): 7094-7102.

Doyle, Sharon A, ed. *High Throughput Protein Expression and Purification: Methods and Protocols (Methods in Molecular Biology)*. Humana Press, 2008.

Genini, E, E Percivalle, A Sarasini, M G Revello, F Baldanti, and G Gerna. "Serum antibody response to the gH/gL/pUL128-131 five-protein complex of human cytomegalovirus (HCMV) in primary and reactivated HCMV infections." *Journal of Clinical Virology* 52 (2011): 113-118.

Huber, M T, and T Compton. "Intracellular Formation and Processing of the Heterotrimeric gH-gL-gO (gCIII) Glycoprotein Envelope Complex of Human Cytomegalovirus." *Journal of Virology* 73 (1999): 3886-3892.

Kinzler, Eric R, Regan N Theiler, and Teresa Compton. "Expression and reconstitution of the gH/gL/gO complex of human cytomegalovirus." *Journal of Clinical Virology*, 2002: 87-95.

Langdon, R H, J Cuccui, and B W. Wren. "N-linked glycosylation in bacteria: an unexpected application." *Future Microbiology* 4 (2009): 401-412.

Loignon, M, et al. "Stable high volumetric production of glycosylated human recombinant IFNalpha2b in HEK293 cells." *BMC Biotechnology* 8 (2008): 65.

Macagno, A, et al. "Isolation of human monoclonal antibodies that potently neutralize human cytomegalovirus infection by targeting different epitopes on the gH/gL/UL128-131A complex." *Journal of Virology* 84 (2010): 1005-13.

Melnicka, M, P P Sedghizadehb, C M Allenc, and T Jaskolla. "Human cytomegalovirus and mucoepidermoid carcinoma of salivary glands: Cell-specific localization of active viral and oncogenic signaling proteins is confirmatory of a causal relationship." *Experimental and Molecular Pathology* 92 (2012): 118-125.

Mocarski, E S, T Shenk, and R F Pass. "Cytomegalovirus." In *Fields Virology*, edited by David M Knipe and Peter M Howley. Philadelphia, Pa., USA: Lippincott Williams and Wilkins, 2006.

Murthy, S, et al. "Detection of a Single Identical Cytomegalovirus (CMV) Strain in Recently Seroconverted Young Women." *PLoS One* 6 (2011): e15949.

Needleman, S B, and C D Wunsch. "A general method applicable to the search for similarities in the amino acid sequences of two proteins." *Journal of Molecular Biology* 48 (1970): 443-453.

Patrone, M, M Secchi, L Fiorina, M Ierardi, G Milanesi, and A Gallina. "Human Cytomegalovirus UL130 Protein Promotes Endothelial Cell Infection through a Producer Cell Modification of the Virion." *Journal of Virology* 79 (2005): 8361-8373.

Rasmussen, L, A Geissler, C Cowan, A Chase, and M Winters. "The Genes Encoding the gCIII Complex of Human Cytomegalovirus Exist in Highly Diverse Combinations in Clinical Isolates." *Journal of Virology* 76 (2002): 10841-10888.

Rice, P, I Longden, and A Bleasby. "EMBOSS: The European Molecular Biology Open Software Suite." *Trends Genetics* 16 (2000): 276-277.

Rigoutsos, I, et al. "In silico pattern-based analysis of the human cytomegalovirus genome." *Journal of Virology* 77 (2003): 4326-44.

Ryckman, B J, et al. "Characterization of the Human Cytomegalovirus gH/gL/UL128-131 Complex That Mediates Entry into Epithelial and Endothelial Cells." *Journal of Virology* 82 (2008): 60-70.

Ryckman, B J, M C Chase, and D C Johnson. "Human Cytomegalovirus TR Strain Glycoprotein O Acts as a Chaperone Promoting gH/gL Incorporation into Virions but Is Not Present in Virions." *Journal of Virology* 84 (2010): 2597-2609.

Sambrook, J. *Molecular Cloning: A Laboratory Manual.* 3rd. Cold Spring Harbor Laboratory Press, 2000.

Simanek, Amanda M., Jennifer Beam Dowd, Graham Pawelec, David Melzer, Ambarish Dutta, and Allison E. Aiello. "Seropositivity to Cytomegalovirus, Inflammation, All-Cause and Cardiovascular Disease-Related Mortality in the United States." *PLoS ONE* 6 ((2011)): e16103.

Summers, M D, and G E Smith. "A manual of methods for baculovirus vectors and insect cell culture procedures." *Texas Agricultural Experiment Station Bulletin No.* 1555, 1987.

Wang, D, and T Shenk. "Human Cytomegalovirus UL131 Open Reading Frame Is Required for Epithelial Cell Tropism. Human Cytomegalovirus UL131 Open Reading Frame Is Required for Epithelial Cell Tropism." *Journal of Virology* 79 (2005): 10330-10338.

```
                            SEQUENCE LISTING (gH from HCMV strain Merlin = GI:52139248)
                                                                SEQ ID NO: 1
MRPGLPSYLIILAVCLFSHLLSSRYGAEAVSEPLDKAFHLLLNTYGRPIRFLRENTTQCTYNSSLRNSTVVRENAIS
FNFFQSYNQYYVFHMPRCLFAGPLAEQFLNQVDLTETLERYQQRLNTYALVSKDLASYRSFSQQLKAQDSLGEQPTT
VPPPIDLSIPHVWMPPQTTPHGWTESHTTSGLHRPHFNQTCILFDGHDLLFSTVTPCLHQGFYLIDELRYVKITLTE
DFFVVTVSIDDDTPMLLIFGHLPRVLFKAPYQRDNFILRQTEKHELLVLVKKDQLNRHSYLKDPDFLDAALDFNYLD
LSALLRNSFHRYAVDVLKSGRCQMLDRRTVEMAFAYALALFAAARQEEAGAQVSVPRALDRQAALLQIQEFMITCLS
QTPPRTTLLLYPTAVDLAKRALWTPNQITDITSLVRLVYILSKQNQQHLIPQWALRQIADFALKLHKTHLASFLSAF
ARQELYLMGSLVHSMLVHTTERREIFIVETGLCSLAELSHFTQLLAHPHHEYLSDLYTPCSSSGRRDHSLERLTRLF
PDATVPATVPAALSILSTMQPSTLETFPDLFCLPLGESFSALTVSEHVSYIVTNQYLIKGISYPVSTTVVGQSLIIT
QTDSQTKCELTRNMHTTHSITVALNISLENCAFCQSALLEYDDTQGVINIMYMHDSDDVLFALDPYNEVVSSPRTH
YLMLLKNGTVLEVTDVVVDATDSRLLMMSVYALSAIIGIYLLYRMLKTC (gH from HCMV strain Towne = GI:138314)
                                                                SEQ ID NO: 2
MRPGLPSYLIVLAVCLLSHLLSSRYGAEAISEPLDKAFHLLLNTYGRPIRFLRENTTQCTYNSSLRNSTVVRENAIS
FNFFQSYNQYYVFHMPRCLFAGPLAEQFLNQVDLTETLERYQQRLNTYALVSKDLASYRSFSQQLKAQDSLGEQPTT
VPPPIDLSIPHVWMPPQTTPHGWTESHTTSGLHRPHFNQTCILFDGHDLLFSTVTPCLHQGFYLIDELRYVKITLTE
DFFVVTVSIDDDTPMLLIFGHLPRVLFKAPYQRDNFILRQTEKHELLVLVKKDQLNRHSYLKDPDFLDAALDFNYLD
LSALLRNSFHRYAVDVLKSGRCQMLDRRTVEMAFAYALALFAAARQEEAGAQVSVPRALDRQAALLQIQEFMITCLS
QTPPRTTLLLYPTAVDLAKRALWTPNQITDITSLVRLVYILSKQNQQHLIPQWALRQIADFALKLHKTHLASFLSAF
ARQELYLMGSLVHSMLVHTTERREIFIVETGLCSLAELSHFTQLLAHPHHEYLSDLYTPCSSSGRRDHSLERLTRLF
PDATVPTTVPAALSILSTMQPSTLETFPDLFCLPLGESFSALTVSEHVSYVVTNQYLIKGISYPVSTTVVGQSLIIT
QTDSQTKCELTRNMHTTHSITAALNISLENCAFCQSALLEYDDTQGVINIMYMHDSDDVLFALDPYNEVVSSPRTH
YLMLLKNGTVLEVTDVVVDATDSRLLMMSVYALSAIIGIYLLYRMLKTC (gH from HCMV strain AD169 = GI:138313)
                                                                SEQ ID NO: 3
MRPGLPPYLTVFTVYLLSHLPSQRYGADAASEALDPHAFHLLLNTYGRPIRFLRENTTQCTYNSSLRNSTVVRENAI
SFNFFQSYNQYYVFHMPRCLFAGPLAEQFLNQVDLTETLERYQQRLNTYALVSKDLASYRSFSQQLKAQDSLGQQPT
TVPPPIDLSIPHVWMPPQTTPHDWKGSHTTSGLHRPHFNQTCILFDGHDLLFSTVTPCLHQGFYLMDELRYVKITLT
EDFFVVTVSIDDDTPMLLIFGHLPRVLFKAPYQRDNFILRQTEKHELLVLVKKAQLNRHSYLKDSDFLDAALDFNYL
DLSALLRNSFHRYAVDVLKSGRCQMLDRRTVEMAFAYALALFAAARQEEAGTEISIPRALDRQAALLQIQEFMITCL
SQTPPRTTLLLYPTAVDLAKRALWTPDQITDITSLVRLVYILSKQNQQHLIPQWALRQIADFALQLHKTHLASFLSA
FARQELYLMGSLVHSMLVHTTERREIFIVETGLCSLAELSHFTQLLAHPHHEYLSDLYTPCSSSGRRDHSLERLTRL
FPDATVPATVPAALSILSTMQPSTLETFPDLFCLPLGESFSALTVSEHVSYVVTNQYLIKGISYPVSTTVVGQSLII
TQTDSQTKCELTRNMHTTHSITAALNISLENCAFCQSALLEYDDTQGVINIMYMHDSDDVLFALDPYNEVVSSPRT
HYLMLLKNGTVLEVTDVVVDATDSRLLMMSVYALSAIIGIYLLYRMLKTC (gH protein consisting of amino acid residues 1-715 of SEQ ID NO: 1)
                                                                SEQ ID NO: 4
MRPGLPSYLIILAVCLFSHLLSSRYGAEAVSEPLDKAFHLLLNTYGRPIRFLRENTTQCTYNSSLRNSTVVRENAIS
FNFFQSYNQYYVFHMPRCLFAGPLAEQFLNQVDLTETLERYQQRLNTYALVSKDLASYRSFSQQLKAQDSLGEQPTT
VPPPIDLSIPHVWMPPQTTPHGWTESHTTSGLHRPHFNQTCILFDGHDLLFSTVTPCLHQGFYLIDELRYVKITLTE
DFFVVTVSIDDDTPMLLIFGHLPRVLFKAPYQRDNFILRQTEKHELLVLVKKDQLNRHSYLKDPDFLDAALDFNYLD
LSALLRNSFHRYAVDVLKSGRCQMLDRRTVEMAFAYALALFAAARQEEAGAQVSVPRALDRQAALLQIQEFMITCLS
QTPPRTTLLLYPTAVDLAKRALWTPNQITDITSLVRLVYILSKQNQQHLIPQWALRQIADFALKLHKTHLASFLSAF
ARQELYLMGSLVHSMLVHTTERREIFIVETGLCSLAELSHFTQLLAHPHHEYLSDLYTPCSSSGRRDHSLERLTRLF
PDATVPATVPAALSILSTMQPSTLETFPDLFCLPLGESFSALTVSEHVSYIVTNQYLIKGISYPVSTTVVGQSLIIT
QTDSQTKCELTRNMHTTHSITVALNISLENCAFCQSALLEYDDTQGVINIMYMHDSDDVLFALDPYNEVVSSPRTH
YLMLLKNGTVLEVTDVVVDATD (C-terminal extension which includes a myc-tag and a polyhistidine-tag)
                                                                SEQ ID NO: 5
GTKLGPEQKLISEEDLNSAVDHHHHHH (gH protein comprising SEQ ID NOs: 4 and 5)
                                                                SEQ ID NO: 6
MRPGLPSYLIILAVCLFSHLLSSRYGAEAVSEPLDKAFHLLLNTYGRPIRFLRENTTQCTYNSSLRNSTVVRENAIS
FNFFQSYNQYYVFHMPRCLFAGPLAEQFLNQVDLTETLERYQQRLNTYALVSKDLASYRSFSQQLKAQDSLGEQPTT
VPPPIDLSIPHVWMPPQTTPHGWTESHTTSGLHRPHFNQTCILFDGHDLLFSTVTPCLHQGFYLIDELRYVKITLTE
DFFVVTVSIDDDTPMLLIFGHLPRVLFKAPYQRDNFILRQTEKHELLVLVKKDQLNRHSYLKDPDFLDAALDFNYLD
LSALLRNSFHRYAVDVLKSGRCQMLDRRTVEMAFAYALALFAAARQEEAGAQVSVPRALDRQAALLQIQEFMITCLS
```

QTPPRTTLLLYPTAVDLAKRALWTPNQITDITSLVRLVYILSKQNQQHLIPQWALRQIADFALKLHKTHLASFLSAF
ARQELYLMGSLVHSMLVHTTERREIFIVETGLCSLAELSHFTQLLAHPHHEYLSDLYTPCSSSGRRDHSLERLTRLF
PDATVPATVPAALSILSTMQPSTLETFPDLFCLPLGESFSALTVSEHVSYIVTNQYLIKGISYPVSTTVVGQSLIIT
QTDSQTKCELTRNMHTTHSITVALNISLENCAFCQSALLEYDDTQGVINIMYMHDSDDVLFALDPYNEVVVSSPRTH
YLMLLKNGTVLEVTDVVVDATDGTKLGPEQKLISEEDLNSAVDHHHHHH (gL from HCMV strain Merlin = GI:39842115)
SEQ ID NO: 7
MCRRPDCGFSFSPGPVILLWCCLLLPIVSSAAVSVAPTAAEKVPAECPELTRRCLLGEVFEGDKYESWLRPLVNVTG
RDGPLSQLIRYRPVTPEAANSVLLDEAFLDTLALLYNNPDQLRALLTLLSSDTAPRWMTVMRGYSECGDGSPAVYTC
VDDLCRGYDLTRLSYGRSIFTEHVLGFELVPPSLFNVVVAIRNEATRTNRAVRLPVSTAAAPEGITLFYGLYNAVKE
FCLRHQLDPPLLRHLDKYYAGLPPELKQTRVNLPAHSRYGPQAVDAR (gL from HCMV strain Towne = GI:239909463)
SEQ ID NO: 8
MCRRPDCGFSFSPGPVALLWCCLLLPIVSSATVSVAPTVAEKVPAECPELTRRCLLGEVFQGDKYESWLRPLVNVTR
RDGPLSQLIRYRPVTPEAANSVLLDDAFLDTLALLYNNPDQLRALLTLLSSDTAPRWMTVMRGYSECGDGSPAVYTC
VDDLCRGYDLTRLSYGRSIFTEHVLGFELVPPSLFNVVVAIRNEATRTNRAVRLPVSTAAAPEGITLFYGLYNAVKE
FCLRHQLDPPLLRHLDKYYAGLPPELKQTRVNLPAHSRYGPQAVDAR (gL from HCMV strain AD169 = GI:2506510)
SEQ ID NO: 9
MCRRPDCGFSFSPGPVVLLWCCLLLPIVSSVAVSVAPTAAEKVPAECPELTRRCLLGEVFQGDKYESWLRPLVNVTR
RDGPLSQLIRYRPVTPEAANSVLLDDAFLDTLALLYNNPDQLRALLTLLSSDTAPRWMTVMRGYSECGDGSPAVYTC
VDDLCRGYDLTRLSYGRSIFTEHVLGFELVPPSLFNVVVAIRNEATRTNRAVRLPVSTAAAPEGITLFYGLYNAVKE
FCLRHQLDPPLLRHLDKYYAGLPPELKQTRVNLPAHSRYGPQAVDAR (gO from HCMV strain Merlin = GI:39842082)
SEQ ID NO: 10
MGKKEMIMVKGIPKIMLLISITFLLLSLINCNVLVNSRGTRRSWPYTVLSYRGKEILKKQKEDILKRLMSTSSDGYR
FLMYPSQQKFHAIVISMDKFPQDYILAGPIRNDSITHMWFDFYSTQLRKPAKYVYSEYNHTAHKITLRPPPCGTVPS
MNCLSEMLNVSKRNDTGEKGCGNFTTFNPMFFNVPRWNTKLYIGSNKVNVDSQTIYFLGLTALLLRYAQRNCTRSFY
LVNAMSRNLFRVPKYINGTKLKNTMRKLKRKQALVKEQPQKKNKSQSTTTPYLSYTTSTAFNVTTNVTYSATAAVT
RVATSTTGYRPDSNFMKSIMATQLRDLATWVYTTLRYRNEPFCKPDRNRTAVSEFMKNTHVLIRNETPYTIYGTLDM
SSLYYNETMSVENETASDNNETTPTSPSTRFQRTFIDPLWDYLDSLLFLDKIRNFSLQLPAYGNLTPPEHRRAANLS
TLNSLWWWSQ (gO from HCMV strain AD169 = GI:136968)
SEQ ID NO: 11
MGRKEMMVRDVPKMVFLISISFLLVSFINCKVMSKALYNRPWRGLVLSKIGKYKLDQLKLEILRQLETTISTKYNVS
KQPVKNLTMNMTEFPQYYILAGPIQNYSITYLWFDFYSTQLRKPAKYVYSQYNHTAKTITFRPPPCGTVPSMTCLSE
MLNVSKRNDTGEQGCGNFTTFNPMFFNVPRWNTKLYVGPTKVNVDSQTIYFLGLTALLLRYAQRNCTHSFYLVNAMS
RNLFRVPKYINGTKLKNTMRKLKRKQAPVKEQFEKKAKKTQSTTTPYFSYTTSAALNVTTNVTYSITTAARRVSTST
IAYRPDSSFMKSIMATQLRDLATWVYTTLRYRQNPFCEPSRNRTAVSEFMKNTHVLIRNETPYTIYGTLDMSSLYYN
ETMFVENKTASDSNKTTPTSPSMGFQRTFIDPLWDYLDSLLFLDEIRNFSLRSPTYVNLTPPEHRRAVNLSTLNSLW
WWLQ (gO from HCMV strain Towne = GI:239909431)
SEQ ID NO: 12
MGRKGEMRGVFNLFFLMSLTFLLFSFINCKIAVARFRVKSQKAKEEERQLKLRILQELASKTGDYYKFFTFPSQQKL
YNITVEMKQFPPNSILAGPIRNHSITHLWFDPHTTQLRKPAKYVYSEYNHTGQKITFRPPSCGTIPSMTCLSEMLNV
SRRNNTGEENCGNFTTFNPMFFNVPRWNTKLYVGPSKVNVDSQTIYFLGLAALLLRYAQRNCTRSFYLVNAMSRNIF
RVPKYINSTKLKNTMRKLKRKQAPVKSISKKSRVSTTTPYSSYTSTIFNVSTNVTYSPIVPTRIPTSTIGYRPDENF
MKSILTTQLKDLATWVYTTLRYRDEPFCKPNRNRTAVSEFMKNTHVLIRNETPYTIYGTLDMSSLYYNDTMPVENET
ASDNNKTTPTSPSTRFQRTFIDPMWDYLDSLLFLSEIRNFSLQSSTYGNLTPPEHRRAVNLSTLNSLWWWLQ (pUL128 from HCMV strain Merlin = GI:39842124)
SEQ ID NO: 13
MSPKDLTPFLTALWLLLGHSRVPRVRAEECCEFINVNHPPERCYDFKMCNRFTVALRCPDGEVCYSPEKTAEIRGIV
TTMTHSLTRQVVHNKLTSCNYNPLYLEADGRIRCGKVNDKAQYLLGAAGSVPY (pUL128 from HCMV strain Towne = GI:39841882)
SEQ ID NO: 14
MSPKNLTPFLTALWLLLGHSRVPRVRAEECCEFINVNHPPERCYDFKMCNRFTVALRCPDGEVCYSPEKTAEIRGIV
TTMTHSLTRQVVHNKLTSCNYNPLYLEADGRIRCGKVNDKAQYLLGAAGSVPYRWINLEYDKITRIVGLDQYLESVK
KHKRLDVCRAKMGYMLQ (pUL128 from HCMV strain AD169 = GI:59803078)
SEQ ID NO: 15
MSPKDLTPFLTTLWLLLGHSRVPRVRAEECCEFINVNHPPERCYDFKMCNRFTVALRCPDGEVCYSPEKTAEIRGIV
TTMTHSLTRQVVHNKLTSCNYNPLYLEADGRIRCGKVNDKAQYLLGAAGSVPYRWINLEYDKITRIVGLDQYLESVK
KHKRLDVCRAKMGYMLQ

SEQUENCE LISTING (pUL130 from HCMV strain Merlin = GI:39842125)

SEQ ID NO: 16

MLRLLLRHHFHCLLLLCAVWATPCLASPWSTLTANQNPSPPWSKLTYSKPHDAATFYCPFLYPSPPRSPLQFSGFQRV
STGPECRNETLYLLYNREGQTLVERSSTWVKKVIWYLSGRNQTILQRMPRTASKPSDGNVQISVEDAKIFGAHMVPK
QTKLLRFVVNDGTRYQMCVMKLESWAHVFRDYSVSFQVRLTFTEANNQTYTFCTHPNLIV (pUL130 from HCMV strain Towne = GI:239909473)

SEQ ID NO: 17

MLRLLLRHHFHCLLLLCAVWATPCLASPWSTLTANQNPSPPWSKLTYSKPHDAATFYCPFLYPSPPRSPLQFSGFQRV
LTGPECRNETLYLLYNREGQTLVERSSTWVKKVIWYLSGRNQTILQRMPRTASKPSDGNVQISVEDAKIFGAHMVPK
QTKLLRFVVNDGTRYQMCVMKLESWAHVFRDYSVSFQVRLTFTEANNQTFTPSAPIPISSFEPVARAGNFENRAS (pUL131A from HCMV strain Merlin = GI:39842126)

SEQ ID NO: 18

MRLCRVWLSVCLCAVVLGQCQRETAEKNDYYRVPHYWDACSRALPDQTRYKYVEQLVDLTLNYHYDASHGLDNFDVL
KRINVTEVSLLISDFRRQNRRGGTNKRTTFNAAGSLAPHARSLEFSVRLFAN (pUL131A from HCMV strain Towne = GI:239909474)

SEQ ID NO: 19

MRLCRVWLSVCLCAVVLGQCQRETAEKNDYYRVPHYWDACSRALPDQTRYKYVEQLVDLTLNYHYDASHGLDNFDVL
KRINVTEVSLLISDFRRQNRRGGTNKRTTFNAAGSLAPHARSLEFSVRLFAN (pUL131A from HCMV strain AD169 = GI:219879712)

SEQ ID NO: 20

MRLCRVWLSVCLCAVVLGQCQRETAEKKRLLPSTALLGRVLSRAARPNPLQVCGTARGPHVELPLRCEPRLGQL (gB from HCMV strain Merlin = GI:39842076)

SEQ ID NO: 21

MESRIWCLVVCVNLCIVCLGAAVSSSSTRGTSATHSHHSSHTTSAAHSRSGSVSQRVTSSQTVSHGVNETIYNTTLK
YGDVVGVNTTKYPYRVCSMAQGTDLIRFERNIVCTSMKPINEDLDEGIMVVYKRNIVAHTFKVRVYQKVLTFRRSYA
YIHTTYLLGSNTEYVAPPMWEIHHINSHSQCYSSYSRVIAGTVFVAYHRDSYENKTMQLMPDDYSNTHSTRYVTKD
QWHSRGSTWLYRETCNLNCMVTITTARSKYPYHFFATSTGDVVDISPFYNGTNRNASYFGENADKFFIFPNYTIVSD
FGRPNSALETHRLVAFLERADSVISWDIQDEKNVTCQLTFWEASERTIRSEAEDSYHFSSAKMTATFLSKKQEVNMS
DSALDCVRDEAINKLQQIFNTSYNQTYEKYGNVSVFETTGGLVVFWQGIKQKSLVELERLANRSSLNLTHNRTKRST
DGNNATHLSNMESVHNLVYAQLQFTYDTLRGYINRALAQIAEAWCVDQRRTLEVFKELSKINPSAILSAIYNKPIAA
RFMGDVLGLASCVTINQTSVKVLRDMNVKESPGRCYSRPVVIFNFANSSYVQYGQLGDNEILLGNHRTEECQLPSL
KIFIAGNSAYEYVDYLFKRMIDLSSISTVDSMIALDIDPLENTDFRVLELYSQKELRSSNVFDLEEIMREFNSYKQR
VKYVEDKVVDPLPPYLKGLDDLMSGLGAAGKAVGVAIGAVGGAVASVVEGVATFLKNPFGAFTIILVAIAVVIITYL
IYTRQRRLCTQPLQNLFPYLVSADGTTVTSGSTKDTSLQAPPSYEESVYNSGRKGPGPPSSDASTAAPPYTNEQAYQ
MLLALARLDAEQRAQQNGTDSLDGRTGTQDKGQKPNLLDRLRHRKNGYRHLKDSDEEENV (gB from HCMV strain Towne = GI:138193)

SEQ ID NO: 22

MESRIWCLVVCVNLCIVCLGAAVSSSSTRGTSATHSHHSSHTTSAAHSRSGSVSQRVTSSQTVSHGVNETIYNTTLK
YGDVVGVNTTKYPYRVCSMAQGTDLIRFERNIVCTSMKPINEDLDEGIMVVYKRNIVAHTFKVRVYQKVLTFRRSYA
YIHTTYLLGSNTEYVAPPMWEIHHINSHSQCYSSYSRVIAGTVFVAYHRDSYENKTMQLMPDDYSNTHSTRYVTVKD
QWHSRGSTWLYRETCNLNCMVTITTARSKYPYHFFATSTGDVVDISPFYNGTNRNASYFGENADKFFIFPNYTIVSD
FGRPNSALETHRLVAFLERADSVISWDIQDEKNVTCQLTFWEASERTIRSEAEDSYHFSSAKMTATFLSKKQEVNMS
DSALDCVRDEAINKLQQIFNTSYNQTYEKYGNVSVFETTGGLVVFWQGIKQKSLVELERLANRSSLNLTHNRTKRST
DGNNATHLSNMESVHNLVYAQLQFTYDTLRGYINRALAQIAEAWCVDQRRTLEVFKELSKINPSAILSAIYNKPIAA
RFMGDVLGLASCVTINQTSVKVLRDMNVKESPGRCYSRPVVIFNFANSSYVQYGQLGEDNEILLGNHRTEECQLPSL
KIFIAGNSAYEYVDYLFKRMIDLSSISTVDSMIALDIDPLENTDFRVLELYSQKELRSSNVFDLEEIMREFNSYKQR
VKYVEDKVVDPLPPYLKGLDDLMSGLGAAGKAVGVAIGAVGGAVASVVEGVATFLKNPFGAFTIILVAIAVVIIIYL
IYTRQRRLCMQPLQNLFPYLVSADGTTVTSGNTKDTSLQAPPSYEESVYNSGRKGPGPPSSDASTAAPPYTNEQAYQ
MLLALVRLDAEQRAQQNGTDSLDGQTGTQDKGQKPNLLDRLRHRKNGYRHLKDSDEEENV (gB from HCMV strain AD169 = GI:138192)

SEQ ID NO: 23

MESRIWCLVVCVNLCIVCLGAAVSSSSTSHATSSTHNGSHTSRTTSAQTRSVYSQHVTSSEAVSHRANETIYNTTLK
YGDVVGVNTTKYPYRVCSMAQGTDLIRFERNIICTSMKPINEDLDEGIMVVYKRNIVAHTFKVRVYQKVLTFRRSYA
YIYTTYLLGSNTEYVAPPMWEIHHINKFAQCYSSYSRVIGGTVFVAYHRDSYENKTMQLIPDDYSNTHSTRYVTVKD
QWHSRGSTWLYRETCNLNCMLTITTARSKYPYHFFATSTGDVVYISPFYNGTNRNASYFGENADKFFIFPNYTIVSD
FGRPNAAPETHRLVAFLERADSVISWDIQDEKNVTCQLTFWEASERTIRSEAEDSYHFSSAKMTATFLSKKQEVNMS
DSALDCVRDEAINKLQQIFNTSYNQTYEKYGNVSVFETSGGLVVFWQGIKQKSLVELERLANRSSLNITHRTRRSTS
DNNTTHLSSMESVHNLVYAQLQFTYDTLRGYINRALAQIAEAWCVDQRRTLEVFKELSKINPSAILSAIYNKPIAAR
FMGDVLGLASCVTINQTSVKVLRDMNVKESPGRCYSRPVVIFNFANSSYVQYGQLGEDNEILLGNHRTEECQLPSLK
IFIAGNSAYEYVDYLFKRMIDLSSISTVDSMIALDIDPLENTDFRVLELYSQKELRSSNVFDLEEIMREFNSYKQRV
KYVEDKVVDPLPPYLKGLDDLMSGLGAAGKAVGVAIGAVGGAVASVVEGVATFLKNPFGAFTIILVAIAVVIITYLI
YTRQRRLCTQPLQNLFPYLVSADGTTVTSGSTKDTSLQAPPSYEESVYNSGRKGPGPPSSDASTAAPPYTNEQAYQM
LLALARLDAEQRAQQNGTDSLDGQTGTQDKGQKPNLLDRLRHRKNGYRHLKDSDEEENV (a construct encoding gH(ecto) fused to a C-terminal myc-(His)6 tag)

SEQ ID NO: 24 gacggatcgggagatctcccgatccctatggtgcactctcagtacaatctgctctgatgccgcatagttaagccag
tatctgctccctgcttgtgtgttggaggtcgctgagtagtgcgcgagcaaaatttaagctacaacaaggcaaggctt
gaccgacaattgcatgaagaatctgcttagggttaggcgttttgcgctgcttcgcgatgtacgggccagatatacgc

SEQUENCE LISTING

```
gttgacattgattattgactagttattaatagtaatcaattacggggtcattagttcatagcccatatatggagttc
cgcgttacataacttacggtaaatggcccgcctggctgaccgcccaacgaccccgcccattgacgtcaataatgac
gtatgttcccatagtaacgccaatagggactttccattgacgtcaatggggtggagtatttacggtaaactgccact
tggcagtacatcaagtgtatcatatgccaagtacgccccctattgacgtcaatgacggtaaatggcccgcctggcat
tatgcccagtacatgaccttatgggactttcctacttggcagtacatctacgtattagtcatcgctattaccatggt
gatgcggttttggcagtacatcaatgggcgtggatagcggtttgactcacggggatttccaagtctccaccccattg
acgtcaatgggagtttgttttggcaccaaaatcaacgggactttccaaaatgtcgtaacaactccgccccattgacg
caaatgggcggtaggcgtgtacggtgggaggtctatataagcagagctctctggctaactagagaacccactgctta
ctggcttatcgaaattaatacgactcactatagggagacccaagctggctagcgccaccatgaggcctggcctgcc
tcctacctgatcatcctggccgtgtgcctgttcagccacctgctgtccagcagatacggcgccgaggccgtgagcga
gcccctggacaaggcttccacctgctgctgaacacctacggcagacccatccggtttctgcgggagaacaccaccc
agtgcacctacaacagcagcctgcggaacagcaccgtcgtgagagagaacgccatcagcttcaacttttccagagc
tacaaccagtactacgtgttccacatgcccagatgcctgtttgccggccctctggccgagcagttcctgaaccaggt
ggacctgaccgagacactggaaagataccagcagcggctgaatacctacgccctggtgtccaaggacctggccagct
accggtcctttagccagcagctcaaggctcaggatagcctcggcgagcagcctaccaccgtgcccctcccatcgac
ctgagcatcccccacgtgtggatgctcccagaccacccctcacggctggaccggagagccacaccacctccggcct
gcacagacccccacttcaaccagacctgcatcctgttcgacggccacgacctgctgtttagcaccgtgacccctgcc
tgcaccagggcttctacctgatcgacgagctgagatacgtgaagatcaccctgaccgaggattttcttcgtggtcacc
gtgtccatcgacgacgacacccccatgctgctgatcttcggccacctgcccagagtgctgttcaaggcccctacca
gcgggacaacttcatcctgcggcagaccgagaagcacgagctgctggtgctggtcaagaaggaccagctgaaccggc
actcctacctgaaggaccccgacttcctggacgccgccctggacttcaactacctggacctgagcgccctgctgaga
aacagcttccacagatacgccgtgacgtgctgaagtccggacggtgccagatgctcgatcggcggaccgtggagat
ggccttcgcctatgccctgccctgttcgccgctgccagacaggaagaggctggcgcccaggtgtcagtgcccagag
ccctggatagacaggccgccctgctgcagatccagaattcatgatcacctgcctgagccagaccccccctagaacc
acctgctgctgtaccccacagccgtggatctggccaagaggggccctgtggaccccccaaccagatcaccgacatcac
aagcctcgtgcggctcgtgtacatcctgagcaagcagaaccagcagcacctgatcccccagtgggccctgagacaga
tcgccgacttcgccctgaagctgcacaagacccatcggccagctttctgagcgccttcgccaggcaggaactgtac
ctgatgggcagcctggtccacagcatgctggtgcatatcacccgagcggcgggagatcttcatcgtggagacaggct
gtgtagcctggccgagctgtcccactttacccagctgctggccaccctcaccacgagtacctgagcgacctgtaca
ccccctgcagcagcagcggcagacgggaccacagcctggaacggctgaccagactgttccccgatgccaccgtgcct
gctacagtgcctgccgcctgtccatcctgtccaccatgcagcccagcaccctgaaaccttccccgacctgttctg
cctgccccctgggcgagagcttttagcgccctgaccgtgtccgagcacgtgctactacatcgtgaccaatcagtacctga
tcaagggcatcagctaccccgtgtccaccacagtcgtgggccagagcctgatcatcaccccagaccgacagccagcc
aagtgcgagctgacccggaacatgcacaccacacacagcatcaccgtggccctgaacatcagcctggaaaactgcgc
tttctgtcagtctgccctgctggaatacgacgatacccagggcgtgatcaacatcatgtacatgcacgacagcgacg
acgtgctgttcgccctggacccctacaacgaggtggtggtgtccagcccccggaccactacctgatgctgctgaag
aacggcaccgtgctgaagtgaccgacgtggtggtggaccgccaccgacggtaccaagcttgggcccgaacaaaact
catctcagaagaggatctgaatagcgccgtcgaccatcatcatcatcatcattgagtttaaacggtctccagcttaa
gtttaaaccgctgatcagcctcgactgtgccttctagttgccagccatctgttgtttgccctcccccgtgccttcc
ttgaccctggaaggtgccactcccactgtcctttcctaataaaatgaggaaattgcatcgcattgtctgagtaggtg
tcattctattctggggggtgggggtggggacagcaaggggggaggattggaagacaatagcaggcatgctgggg
atgcggtgggctctatggcttctgaggcggaaagaaccagctggggctctaggggtatccccacgcgccctgtagc
ggcgcattaagcgcggcgggtgtggtggttacgcgcagcgtgaccgctacacttgccagcgccctagcgcccgctcc
tttcgctttcttcccttcctttctcgccacgttcgccggctttccccgtcaagctctaaatcgggggctcccttttag
ggttccgatttagtgctttacggcacctcgaccccaaaaaacttgattagggtgatggttcacgtagtgggccatcg
ccctgatagacggtttttcgccctttgacgttggagtccacgttctttaatagtggactcttgttccaaactggaac
aacactcaaccctatctcggtctattcttttgatttataagggattttgccgatttcggcctattggttaaaaaatg
agctgatttaacaaaaatttaacgcgaattaattctgtggaatgtgtgtcagttagggtgtggaaagtccccaggct
ccccagcaggcagaagtatgcaaagcatgcatctcaattagtcagcaaccatagtcccgcccctaactccgcccatcccgcc
cctaactccgcccagttccgcccattctccgccccatggctgactaattttttttatttatgcagaggccgaggcc
gcctctgcctctgagctattccagaagtagtgaggaggcttttttggaggcctaggcttttgcaaaaagctcccggga
gcttgtatatccattttcggatctgatcaagagacaggatgaggatcgtttcgcatgattgaacaagatggattgca
cgcaggttctccggccgcttgggtggagaggctattcggctatgactgggcacaacagacaatcggctgctctgatg
ccgccgtgttccggctgtcagcgcaggggcgcccggttcttttttgtcaagaccgacctgtccggtgccctgaatgaa
ctgcaggacgaggcagcgcggctatcgtggctggccacgacgggcgttccttgcgcagctgtgctcgacgttgtcac
tgaagcgggaagggactggctgctattgggcgaagtgccggggcaggatctcctgtcatctcaccttgctcctgccg
agaaagtatccatcatggctgatgcaatgcggcggctgcatacgcttgatccggctacctgcccattcgaccaccaa
gcgaaacatcgcatcgagcgagcacgtactcggatggaagccggtcttgtcgatcaggatgatctggacgaagagca
tcaggggctcgcgccagccgaactgttcgccaggctcaaggcgcgcatgcccgacggcgaggatctcgtcgtgaccc
atggcgatgcctgcttgccgaatatcatggtggaaaatggccgcttttctggattcatcgactgtggccggctgggt
gtggcggaccgctatcaggacatagcgttggctacccgtgatattgctgaagagcttggcggcgaatgggctgaccg
cttcctcgtgctttacggtatcgccgctcccgattcgcagcgcatcgccttctatcgccttcttgacgagttcttct
gagcgggactctggggttcgaaatgaccgaccaagcgacgcccaacctgccatcacgagatttcgattccaccgccg
ccttctatgaaaggttgggcttcggaatcgttttccgggacgccggctggatgatcctccagcgcggggatctcatg
ctggagttcttcgcccaccccaacttgtttattgcagcttataatggttacaaataaagcaatagcatcacaaattt
cacaaataaagcatttttttcactgcattctagttgtggtttgtccaaactcatcaatgtatcttatcatgtctgta
taccgtcgacctctagctagagcttggcgtaatcatggtcatagctgtttcctgtgtgaaattgttatccgctcaca
attccacacaacatacgagccggaagcataaagtgtaaagcctggggtgcctaatgagtgagctaactcacattaat
tgcgttgcgctcactgcccgctttccagtcgggaaacctgtcgtgccagctgcattaatgaatcggccaacgcgcgg
ggagaggcggtttgcgtattgggcgctcttccgcttcctcgctcactgactcgctgcgctcggtcgttcggctgcgg
cgagcggtatcagctcactcaaaggcggtaatacggttatccacagaatcaggggataacgcaggaaagaacatgtg
agcaaaaggccagcaaaaggccaggaaccgtaaaaaggccgcgttgctggcgtttttccataggctccgcccccctg
acgagcatcacaaaaatcgacgctcaagtcagaggtggcgaaacccgacaggactataaagataccaggcgtttccc
cctggaagctccctcgtgcgctctcctgttccgaccctgccgcttaccggatacctgtccgcctttctcccttcggg
aagcgtggcgctttctcatagctcacgctgtaggtatctcagttcggtgtaggtcgttcgctccaagctgggctgtg
tgcacgaaccccccgttcagcccgaccgctgcgccttatccggtaactatcgtcttgagtccaacccggtaagacac
```

-continued

SEQUENCE LISTING

```
gacttatcgccactggcagcagccactggtaacaggattagcagagcgaggtatgtaggcggtgctacagagttctt
gaagtggtggcctaactacggctacactagaagaacagtatttggtatctgcgctctgctgaagccagttaccttcg
gaaaaagagttggtagctcttgatccggcaaacaaaccaccgctggtagcggtggttttttttgtttgcaagcagcag
attacgcgcagaaaaaaggatctcaagaagatcctttgatcttttctacggggtctgacgctcagtggaacgaaaa
ctcacgttaagggattttggtcatgagattatcaaaaaggatcttcacctagatcctttaaattaaaaatgaagtt
ttaaatcaatctaaagtatatatgagtaaacttggtctgacagttaccaatgcttaatcagtgaggcacctatctca
gcgatctgtctatttcgttcatccatagttgcctgactccccgtcgtgtagataactacgataacggggaggggcttacc
atctggccccagtgctgcaatgataccgcgagacccacgctcaccggctccagatttatcagcaataaaccagccag
ccggaagggccgagcgcagaagtggtcctgcaacttatccgcctccatccagtctattaattgttgccgggaagct
agagtaagtagttcgccagttaatagtttgcgcaacgttgttgccattgctacaggcatcgtggtgtcacgctcgtc
gtttggtatggcttcattcagctccggttcccaacgatcaaggcgagttacatgatccccatgttgtgcaaaaaag
cggttagctccttcggtcctccgatcgttgtcagaagtaagttggccgcagtgttatcactcatggttatggcagca
ctgcataattctcttactgtcatgccatccgtaagatgcttttctgtgactggtgagtactcaaccaagtcattctg
agaatagtgtatgcggcgaccgagttgctcttgcccggcgtcaatacgggataataccgcgccacatagcagaactt
taaaagtgctcatcattggaaaacgttcttcggggcgaaaactctcaaggatcttaccgctgttgagatccagttcg
atgtaacccactcgtgcacccaactgatcttcagcatcttttactttcaccagcgtttctgggtgagcaaaaacagg
aaggcaaaatgccgcaaaaaagggaataagggcgacacgaaatgttgaatactcatactcttccttttttcaatatt
attgaagcatttatcagggttattgtctcatgagcggatacatatttgaatgtatttagaaaaataaacaaataggg
gttccgcgcacatttccccgaaaagtgccacctgacgtc
```

(a construct encoding full-length gL)

SEQ ID NO: 25

```
gccgcggaatttcgactctaggccattgcatacgttgtatctatatcataatatgtacatttatattggctcatgtc
caatatgaccgccatgttgacattgattattgactagttattaatagtaatcaattacggggtcattagttcatagc
ccatatatggagttccgcgttacataacttacggtaaatggcccgcctggctgaccgcccaacgacccccgcccatt
gacgtcaataatgacgtatgttcccatagtaacgccaatagggactttccattgacgtcaatgggtggagtatttac
ggtaaactgcccacttggcagtacatcaagtgtatcatatgccaagtccgcccctattgacgtcaatgacggtaaa
tggcccgcctggcattatgcccagtacatgaccttacgggactttcctacttggcagtacatctacgtattagtcat
cgctattaccatggtgatgcggttttggcagtacaccaatgggcgtggatagcggtttgactcacggggatttccaa
gtctccaccccattgacgtcaatgggagtttgttttggcaccaaaatcaacgggactttccaaaatgtcgtaataac
cccgccccgttgacgcaaatgggcggtaggcgtgtacggtgggaggtctatataagcagagctcgtttagtgaaccg
tcagatcgcctggagacgccatccacgctgttttgacctccatagaagacaccgggaccgatccagcctccgcggcc
gggaacggtgcattggaacgcggattcccccgtgccaagagtgacgtaagtaccgcctatagactctataggcacacc
cctttggctcttatgcatgctatactgttttttggcttggggcctatacaccccgcttccttatgctataggtgatg
gtatagcttagcctataggtgtgggttattgaccattattgaccactccctattggtgacgatactttccattact
aatccataacatggctctttgccacaactatctctattggctatatgccaatactctgtccttcagagactgacacg
gactctgtattttacaggatggggtcccatttattatttacaaattcacatatacaacaacgcgctccccccgtgcc
cgcagttttttattaaacatagcgtgggatctccacgcgaattctcgggtacgtgttccggacatgggctcttctccgg
tagcggcggagcttccacatccgagccctggtcccatgcctccagcggctcatggtcgctcggcagctccttgctcc
taacagtggaggccagacttaggcacagcacaatgcccaccaccaccagtgtgccgcacaaggccgtggcggtaggg
tatgtgtctgaaaatgagctcggagattgggctcgcaccgctgacgcagatggaagacttaaggcagcggcagaaga
agatgcaggcagctgagttgttgtattctgataagagtcagaggtaactcccgttgcggtgctgttaacggtggagg
gcagtgtagtctgagcagtactcgttgctgccgcgcgcgccaccagacataatagctgacagactaacagactgttc
cttttccatgggtcttttctgcagtcaccgtcgtcgacgccaccatgtgcagaaggcccgactgcggcttcagcttca
gccctggaccgtgatcctgctgtggtgctgcctgctgctcctatcgtgctcctcgccgccgtgtctgtggccccct
acagccgccgagaaggtgccagccgagtgccccgagctgaccagaagatgcctgctgggcgaggtgttcgagggcga
caagtacgagagctggctgcgccccctggtcaacgtgaccggcagagatggcccctgagccagctgatccggtaca
gacccgtgaccccgaggccgccaatagcgtgctgctggacgaggccttcctggatacctggccctgctgtacaac
aaccccgaccagctgagagccctgctgaccctgctgtccagcgacaccgccccccagatggatgacctgatgcgggg
ctacagcgagtgtgagatggcagccctgccgtgtacacctgcgtggacgacctgtgcagaggctacgacctgacca
gactgagctacggccggtccatcttcacagagcacgtgctgggcttcgagctggtgcccccagcctgttcaacgtg
gtggtggccatccggaacgaggccaccagaaccaacagagccgtgcggctgcctgtgtctacagccgctgcacctga
gggcatcacactgttctacggcctgtacaacgccgtgaaagagttctgcctccggcaccagctggatcccccctgc
tgagacacctggacaagtactacgccggcctgcccccagagctgaagcagaccagagtgaacctgcccgcccacagc
agatatggccctcaggccgtggacgccagatgataatctagaaagccatggatatcggatccactacgcgttagagc
tcgctgatcagcctcgactgtgccttctagttgccagccatctgttgtttgcccctcccccgtgccttccttgaccc
tggaaggtgccactccactgtcctttcctaataaaatgaggaaattgcatcgcattgtctgagtaggtgtcattct
attctggggggtggggtggggcaggacagcaaggggaggattgggaagacaatagcaggggggtgggcgaagaact
ccagcatgagatccccgcgctggaggatcatccagccggcgtcccggaaaacgattccgaagccaacctttcatag
aaggcggcggtggaatcgaaatctcgtgatggcaggttgggcgtcgcttggtcggtcatttcgaaccccagagtccc
gctcagaagaactcgtcaagaaggcgatagaaggcgatgcgctgcgaatcgggagcggcgataccgtaaagcacgag
gaagcggtcagccattcgccgccaagctcttcagcaatatcacgggtagccaacgctatgtcctgatagcggtccg
ccacacccagccggccacagtcgatgaatccagaaaagcggccattttccaccatgatattcggcaagcaggcatcg
ccatgggtcacgacgagatcctcgccgtcgggcatgcgcgccttgagcctggcgaacagttcggctggcgcgagccc
ctgatgctcttcgtccagatcatcctgatcgacaagaccggcttccatccgagtacgtgctcgctcgatgcgatgtt
tcgcttggtggtcgaatgggcaggtagccggatcaagcgtatgcagccgccgcattgcatcagccatgatggatact
ttctcggcaggagcaagtgagatgacaggagatcctgccccggcacttcgcccaatagcagccagtccctttccgcgc
ttcagtgacaacgtcgagcacagctgcgcaaggaacgcccgtcgtggccagccacgatagccgcgctgcctcgtcct
gcagttcattcagggcaccggacaggtcggtcttgacaaaagaaccgggcgcccctgcgctgacagccggaacacg
gcggcatcagagcagccgattgtctgttgtgcccagtcatagccgaatagcctctccaccccaagcggccggagaacc
tgcgtgcaatccatcttgttcaatcatgcgaaacgatcctcatcctgtctcttgatcagatcttgatccctgcgcc
atcagatccttggcggcaagaaagccatccagtttactttgcagggcttcccaaccttaccagagggcgccccagct
ggcaattccggttcgcttgctgtccataaaaccgcccagtctagctatcgccatgtaagcccactgcaagctacctg
ctttctctttgcgcttgcgttttcccttgtccagatagcccagtagctgacattcatccgggtcagcaccgtttct
gcggactggctttctacgtgttccgcttcctttagcagcccttgcgccctgagtgcttgcggcagcgtgaagctaat
tcatggttaaatttttgttaaatcagctcattttttaaccaataggccgaaatcggcaaaatcccttataaatcaaa
agaatagcccgagatagggttgagtgttgttccagtttggaacaagagtccactattaaagaacgtggactccaacg
```

SEQUENCE LISTING tcaaagggcgaaaaaccgtctatcagggcgatggccggatcagcttatgcggtgtgaaataccgcacagatgcgtaa
ggagaaaataccgcatcaggcgctcttccgcttcctcgctcactgactcgctgcgctcggtcgttcggctgcggcga
gcggtatcagctcactcaaaggcggtaatacggttatccacagaatcaggggataacgcaggaaagaacatgtgagc
aaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccct
ggaagctccctcgtgcgctctcctgttccgaccctgccgcttaccggatacctgtccgcctttctcccttcgggaag
cgtggcgctttctcatagctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagttcttgaa
gtggtggcctaactacggctacactagaaggacagtatttggtatctgcgctctgctgaagccagttaccttcggaa
aaagagttggtagctcttgatccggcaaacaaaccaccgctggtagcggtggtttttttgtttgcaagcagcagatt
acgcgcagaaaaaaggatctcaagaagatcctttgatcttttctactgaacggtgatccccaccggaattgcg (a construct encoding full-length pUL128)

SEQ ID NO: 26 gccgcggaatttcgactctaggccattgcatacgttgtatctatatcataatatgtacatttatattggctcatgtc
caatatgaccgccatgttgacattgattattgactagttattaatagtaatcaattacggggtcattagttcatagc
ccatatatggagttccgcgttacataacttacggtaaatggcccgcctggctgaccgcccaacgacccccgcccatt
gacgtcaataatgacgtatgttcccatagtaacgccaatagggactttccattgacgtcaatgggtggagtattta c
ggtaaactgcccacttggcagtacatcaagtgtatcatatgccaagtccgccccctattgacgtcaatgacggtaaa
tggcccgcctggcattatgcccagtacatgaccttacgggactttcctacttggcagtacatctacgtattagtcat
cgctattaccatggtgatgcggttttggcagtacaccaatgggcgtggatagcggtttgactcacggggatttccaa
gtctccaccccattgacgtcaatgggagtttgttttggcaccaaaatcaacgggactttccaaaatgtcgtaataac
cccgccccgttgacgcaaatgggcggtaggcgtgtacggtgggaggtctatataagcagagctcgtttagtgaaccg
tcagatcgcctggagacgccatccacgctgttttgacctccatagaagacaccgggaccgatccagcctccgcggcc
gggaacggtgcattggaacgcggattcccgtgccaagagtgacgtaagtaccgcctatagactctataggcacacc
cctttggctcttatgcatgctatactgttttggcttggggcctatacaccccgcttccttatgctatggtgatg
gtatagcttagcctataggtgtgggttattgaccattattgaccactccctattggtgacgatactttccattact
aatccataacatggctctttgccacaactatctctattggctatatgccaatactctgtccttcagagactgacacg
gactctgtattttacaggatggggtcccatttattatttacaaattcacatatacaacaacgccgtcccccgtgcc
cgcagttttattaaacatagcgtgggatctccacgcgaatctcgggtacgtgttccggacatgggctcttctccgg
tagcgggcggagcttccacatccgagccctgttcccatgcctccagcggctcatggtcgctcggcagctccttgctcc
taacagtggaggccagacttaggcacagcacaatgcccaccaccaccagtgtgccgcacaaggccgtggcggtaggg
tatgtgtctgaaaatgagctcggagattgggctcgcaccgctgacgcagatggaagacttaaggcagcggcagaaga
agatgcaggcagctgagttgttgtattctgataagagtcagaggtaactcccgttgcggtgctgttaacggtggagg
gcagtgtagtctgagcagtactcgttgctgccgcgcgcgccaccagacataatagctgacagactaacagactgttc
cttccatgggtcttttctgcagtcaccgtcgtcgacgccaccatgagccccaaggacctgaccccccttcctgacaa
ccctgtggctgctcctgggccatagcagagtgcctagagtgcgggccgaggaatgctgcgagttcatcaacgtgaac
cacccccccgagcggtgctacgacttcaagatgtgcaaccggttcaccgtggccctgagtgccccgacggcgaagt
gtgctacagccccgagaaaaccgccgagatccggggcatcgtgaccaccatgacccacagcctgacccggcaggtgg
tgcacaacaagctgaccagctgcaactacaacccctgtacctggaagccgacggccggatcagatgcggcaaagtg
aacgacaaggcccagtacctgctgggagccgccggaagcgtgccctaccggtggatcaacctggaatacgacaagat
caccggatcgtgggcctggaccagtacctggaaagcgtgaagaagccaaccgcgtggacgtgtgcagagccaaga
tgggctacatgctgcagtgataatctagaaagccatggatatcggatccactacgcgttagagctcgctgatcagcc
tcgactgtgccttctagttgccagccatctgttgtttgcccctcccccgtgccttccttgaccctggaaggtgccac
tcccactgtcctttcctaataaaatgaggaaattgcatcgcattgtctgagtaggtgtcattctattctgggggtg
gggtggggcaggacagcaaggggaggattgggaagacaatagcaggggggtgggcgaagaactccagcatgagatc
cccgcgctggaggatcatcagccggcggtcccggaaaacgattccgaagcccaacctttcatagaaggcggcggtgg
aatcgaaatctcgtgatggcaggttgggcgtcgcttggtcggtcatttcgaaccccagagtcccgctcagaagaact
cgtcaagaaggcgatagaaggcgatgcgctgcgaatcgggagcggcgataccgtaaagcacgaggaagcggtcagcc
cattcgccgccaagctcttcagcaatatcacgggtagccaacgctatgtcctgatagcggtccgccacacccagccg
gccacagtcgatgaatccagaaaagcggccattttccaccatgatattcggcaagcaggcatcgccatgggtcacga
cgagatcctcgccgtcgggcatgcgcgccttgagcctggcgaacagttcggctggcgcgagcccctgatgctcttcg
tccagatcatcctgatcgacaagaccggcttccatccgagtacgtgctcgctcgatgcgatgtttcgcttggtggtc
gaatgggcaggtagccggatcaagcgtatgcagccgccgcattgcatcagccatgatggatactttctcggcaggag
caaggtgagatgacaggagatcctgccccggcacttcgcccaatagcagccagtcccttcccgcttcagtgacaacg
tcgagcacagctgcgcaaggaacgcccgtcgtggccagccacgatagccgcgctgcctcgtcctgcagttcattcag
ggcaccggacaggtcggtcttgacaaaaagaaccgggcgcccctgcgctgacagccggaacacggcggcatcagagc
agccgattgtctgttgtgcccagtcatagccgaatagcctctccaccccaagcggccggagaacctgcgtgcaatcca
tcttgttcaatcatgcgaaacgatcctcatcctgtctcttgatcagatcttgatccctgcgccatcagatccttgg
cggcaagaaagccatccagtttactttgcagggcttcccaaccttaccagagggcgccccagctggcaattccggtt
cgcttgctgtccataaaaccgcccagtctagctatcgccatgtaagcccactgcaagctacctgctttctctttgcg
cttgcgttttcccttgtccagatagcccagtagctgacattcatccggggtcagcaccgtttctgcggactggcttt
ctacgtgttccgcttcctttagcagcccttgcgccctgagtgcttgcggcagcgtgaagctaattcatgttaaatt
tttgttaaatcagctcattttttaaccataggccgaaatcggcaaaatcccttataaatcaaaagaatagcccgag
ataggggttgagtgttgttccagtttggaacaagagtccactattaaagaacgtggactccaacgtcaaagggcgaaa
aaccgtctatcagggcgatggccggatcagcttatgcggtgtgaaataccgcacagatgcgtaaggagaaaataccg
catcaggcgctcttccgcttcctcgctcactgactcgctgcgctcggtcgttcggctgcggcgagcggtatcagctc
actcaaaggcggtaatacggttatccacagaatcaggggataacgcaggaaagaacatgtgagcaaaaggccagcaa
aaggccaggaaccgtaaaaaggccgcgttgctggcgtttttccataggctccgcccccctgacgagcatcacaaaaa
tcgacgctcaagtcaggtggcgaaacccgacaggactataaagataccaggcgtttccccctggaagctccctcg
tgcgctctcctgttccgaccctgccgcttaccggatacctgtccgcctttctcccttcgggaagcgtggcgctttct
catagctcacgctgtaggtatctcagttcggtgtaggtcgttcgctccaagctgggctgtgtgcacgaaccccccgt
tcagcccgaccgctgcgccttatccggtaactatcgtcttgagtccaacccggtaagacacgacttatcgccactgg

SEQUENCE LISTING cagcagccactggtaacaggattagcagagcgaggtatgtaggcggtgctacagagttcttgaagtggtggcctaac
tacggctacactagaaggacagtatttggtatctgcgctctgctgaagccagttaccttcggaaaaagagttggtag
ctcttgatccggcaaacaaaccaccgctggtagcggtggttttttttgtttgcaagcagcagattacgcgcagaaaaa
aaggatctcaagaagatcctttgatcttttctactgaacggtgatccccaccggaattgcg (a construct encoding full-length pUL130)

SEQ ID NO: 27 gccgcggaatttcgactctaggccattgcatacgttgtatctatatcataatatgtacatttatattggctcatgtc
caatatgaccgccatgttgacattgattattgactagttattaatagtaatcaattacggggtcattagttcatagc
ccatatatggagttccgcgttacataacttacggtaaatggcccgcctggctgaccgcccaacgaccccgcccatt
gacgtcaataatgacgtatgttcccatagtaacgccaatagggactttccattgacgtcaatgggtggagtattac
ggtaaactgcccacttggcagtacatcaagtgtatcatatgccaagtccgcccccctattgacgtcaatgacggtaaa
tggcccgcctggcattatgcccagtacatgaccttacgggactttcctacttggcagtacatctacgtattagtcat
cgctattaccatggtgatgcggttttggcagtacaccaatgggcgtggatagcggtttgactcacggggatttccaa
gtctccaccccattgacgtcaatgggagtttgttttggcaccaaaatcaacgggactttccaaaatgtcgtaataac
cccgccccgttgacgcaaatgggcggtaggcgtgtacggtgggaggtctatataagcagagctcgtttagtgaaccg
tcagatcgcctggagacgccatccacgctgttttgacctccataagaagacaccgggaccgatccagcctccgcggcc
gggaacggtgcattggaacgcggattcccgtgccaagagtgacgtaagtaccgcctatagactctataggcacacc
cctttggctcttatgcatgctatactgtttttggcttggggcctatacccccgcttccttatgctataggtgatg
gtatagcttagcctataggtgtgggttattgaccattattgaccacctccccctattggtgacgatactttccattact
aatccataacatggctctttgccacaactatctctattggctatatgccaatactctgtccttcagagactgacacg
gactctgtattttacaggatggggtcccatttattatttacaaattcacatatacaacaacgccgtcccccgtgcc
cgcagttttattaaacatagcgtgggatctccacgcgaatctcgggtacgtgttccggacatgggctcttctccgg
tagcggcggagcttccacatccgagccctggtcccatgcctccagcggctcatggtcgctcggcagctccttgctcc
taacagtggaggccagacttaggcacagcacaatgccaccaccaccagtgtgccgcacaaggccgtggcggtaggg
tatgtgtctgaaaatgagctcggagattgggctcgcaccgctgacgcagatggaagacttaaggcagcggcagaaga
agatgcaggcagctgagttgttgtattctgataagagtcagaggtaactcccgttgcggtgctgttaacggtggagg
gcagtgtagtctgagcagtactcgttgctgccgcgcgccaacagacataatagctgacagactaacagactgttc
ctttccatgggtcttttctgcagtcaccgtcgtcgacgccaccatgctgcggctgctgctgagacaccacttccact
gcctgctgctgtgtgccgtgtgggccaccccttgtctggccagcccttggagcaccctgaccgcaaccagaaccct
agccccccttggtccaagctgacctacagcaagcccacgacgccgccaccttctactgcccctttctgtacccag
ccctcccagaagcccctgcagttcagcggcttccagagagtgtccaccggccctgagtgccggaacgagaacactgt
acctgctgtacaaccgggagggccagacactggtggagcggagcagcacctgggtgaaaaaagtgatctggtatctg
agcggccggaaccagaccatcctgcagcggatgcccagaaccgccagcaagcccagcgacggcaacgtcagatcag
cgtggaggacgccaaaatcttcggcgcccacatggtgcccaagcagaccaagctgctgagattcgtggtcaacgacg
gcaccagatatcagatgtgcgtgatgaagctggaaagctgggccacgtgttccgggactactccgtgagcttccag
gtccggctgaccttcaccgaggccaacaaccagacctacaccttctgcaccccaccccaacctgatcgtgtgataatc
tagaaagcctagatcgattccactacgcgttagagctcgctgatcagccctcgactgtgccttctagttgccagc
catctgttgtttgccctccccgtgccttcttgaccctggaaggtgccactcccactgtcctttcctaataaaat
gaggaaattgcatcgcattgtctgagtaggtgtcattctattctgggggtggggtggggcaggacagcaagggga
ggattgggaagacaatagcaggggggtgggcgaagaactccagcatgcatgtccgcgctggaggatcatccagccg
gcgtcccggaaaacgattccgaagcccaacctttcatagaaggcggcggtggaatcgaaatctcgtgatgcaggtt
gggcgtcgcttggtcggtcatttcgaaccccagagtcccgctcagaagaactcgtcaagaaggcgatagaaggcgat
gcgctgcgaatcgggagcggcgataccgtaaagcacgaggaagcggtcagcccattcgccgccaagctcttcagcaa
tatcacgggtagccaacgctatgtcctgatagcggtccgccacacccagccggccacagtcgatgaatccagaaaag
cggccatttcaccatgatattcggcaagcaggcatcgccatgggtcacgacgagatcctcgccgtcgggcatgcg
cgccttgagcctggcgaacagttcggctggcgcgagcccctgatgctcttcgtccagatcatcctgatcgacaagac
cggcttccatccgagtacgtgctcgctcgatgcgatgtttcgcttggtggtcgaatgggcaggtagccggatcaagc
gtatgcagccgccgcattgcatcagccatgatggatactttctcggcaggagcaaggtgagatgacaggagatcctg
ccccggcacttcgcccaatagcagccagtcccttcccgcttcagtgacaacgtcgagcacagctgcgcaaggaacgc
ccgtcgtggccagccacgatagccgcgctgcctcgtcctgcagttcattcagggcaccggacaggtcggtcttgaca
aaaagaaccgggcgcccctgcgctgacagccggaacacggcggcatcagagcagccgattgtctgttgtgcccagtc
atagccgaatagcctctccacccaagcggccggagaacctgcgtgcaatccatcttgttcaatcatgcgaaacgatc
ctcatcctgtctcttgatcagatcttgatccctgcgccatcagatccttggcggcaagaaagccatccagtttact
ttgcagggcttcccaaccttaccagagggcgccccagctggcaattccggttcgcttgctgtccataaaaccgccca
gtctagctatcgccatgtaagcccactgcaagctacctgctttctctttgcgcttgcgttttcccttgtccagatag
cccagtagctgacattcatccggggtcagcaccgtttctgcggactggctttctacgtgttccgcttcctttagcag
cccttgcgccctgagtgcttgcggcagcgtgaagctaattcatggttaaattttttgttaaatcagctcattttttaa
ccaataggccgaaatcggcaaaatcccttataaatcaaaagaatagcccgagatagggttgagtgttgttccagttt
ggaacaagagtccactattaaagaacgtggactccaacgtcaaagggcgaaaaaccgtctatcagggcgatggccgg
atcagcttatgcggtgtgaaataccgcacagatgcgtaaggagaaaataccgcatcaggcgctcttccgcttcctcg
ctcactgactcgctgcgctcggtcgttcggctgcggcgagcggtatcagctcactcaaaggcggtaatacggttatc
cacagaatcaggggataacgcaggaaagaacatgtgagcaaaaggccagcaaaaggccaggaaccgtaaaaaggccg
cgttgctggcgtttttccataggctccgcccccctgacgagcatcacaaaaatcgacgctcaagtcagaggtggcga
aacccgacaggactataaagataccaggcgtttccccctggaagctccctcgtgcgctctcctgttccgaccctgcc
gcttaccggatacctgtccgcctttctcccttcgggaagcgtggcgctttctcatagctcacgctgtaggtatctca
gttcggtgtaggtcgttcgctccaagctgggctgtgtgcacgaaccccccgttcagcccgaccgctgcgccttatcc
ggtaactatcgtcttgagtccaacccggtaagacacgacttatcgccactggcagcagccactggtaacaggattag
cagagcgaggtatgtaggcggtgctacagagttcttgaagtggtggcctaactacggctacactagaaggacagtat
ttggtatctgcgctctgctgaagccagttaccttcggaaaaagagttggtagctcttgatccggcaaacaaaccacc
gctggtagcggtggtttttttgtttgcaagcagcagattacgcgcagaaaaaaaggatctcaagaagatcctttgat
cttttctactgaacggtgatccccaccggaattgcg (a construct encoding full-length pUL131A)

SEQ ID NO: 28 gccgcggaatttcgactctaggccattgcatacgttgtatctatatcataatatgtacatttatattggctcatgtc
caatatgaccgccatgttgacattgattattgactagttattaatagtaatcaattacggggtcattagttcatagc

SEQUENCE LISTING

```
ccatatatggagttccgcgttacataacttacggtaaatggcccgcctggctgaccgcccaacgaccccgcccatt
gacgtcaataatgacgtatgttcccatagtaacgccaatagggactttccattgacgtcaatgggtggagtatttac
ggtaaactgcccacttggcagtacatcaagtgtatcatatgccaagtatgccccccctattgacgtcaatgacggtaaa
tggcccgcctggcattatgcccagtacatgaccttacgggactttcctacttggcagtacatctacgtattagtcat
cgctattaccatggtgatgcggttttggcagtacaccaatgggcgtggatagcggtttgactcacggggatttccaa
gtctccaccccattgacgtcaatgggagtttgttttggcaccaaaatcaacgggactttccaaaatgtcgtaataac
cccgccccgttgacgcaaatgggcggtaggcgtgtacggtgggaggtctatataagcagagctcgtttagtgaaccg
tcagatcgcctggagacgccatccacgctgttttgacctccatagaagacaccgggaccgatccagcctccgcggcc
gggaacggtgcattggaacgcggattcccgtgccaagagtgacgtaagtaccgcctatagactctataggcacacc
cctttggctcttatgcatgctatactgtttttggcttgggcctatacaccccgcttcctatgctataggtgatg
gtatagcttagcctataggtgtgggttattgaccattattgaccactccctattggtgacgatacttccattact
aatccataacatggctctttgccacaactatctctattggctatatgccaactctgtccttcagagactgacacg
gactctgtattttacaggatggggtcccattttattattacaaattcacatatacaacaacgccgtccccgtgcc
cgcagtttttattaaacatagcgtgggatctccacgcgaatctcgggtacgtgttccggacatgggctcttctccgg
tagcggcggagcttccacatccgagccctggtccatgcctccagcggctcatggtcgctcggcagctccttgctcc
taacagtggaggccagacttaggcacagcacaatgcccaccaccaccagtgtgccgcacaaggccgtggcggtaggg
tatgtgtctgaaaatgagctcggagattgggctcgcaccgctgacgcagatggaagacttaaggcagcggcagaaga
agatgcaggcagctgagttgttgtattctgataagagtcagaggtaactcccgttgcggtgctgttaacggtggagg
gcagtgtagtctgagcagtactcgttgctgccgcgcgcgccaccagacataatagctgacagactaacagactgttc
ctttccatgggtcttttctgcagtcaccgtcgtcgacgccaccatgccgctgtgcagagtgtggctgtccgtgtgcc
tgtgtgccgtggtgctgggccagtgccagagagagacagccgagaagaacgactactaccggggtgccccactactgg
gatgcctgcagcagagccctgcccgaccagacccggtacaaatacgtggagcagctcgtggacctgaccctgaacta
ccactacgacgccagccacggcctggacaacttcgacgtgctgaagcggatcaacgtgaccgaggtgtccctgctga
tcagcgacttccggcggcagaacagaagaggcggcaccaacaagcaccttcaacgccgctggctctctgagcc
cctcacgccagatccctggaattcagcgtgcggctgttcgccaactgataatctagaaagccatggatatcggatcc
actacgcgttagagctcgctgatcagcctcgactgtgccttctagttgccagccatctgttgtttgcccctccccg
tgccttccttgaccctggaaggtgccactcccactgtcctttcctaataaaatgaggaaattgcatcgcattgtctg
agtaggtgtcattctattctggggggtttggggtggggcaggacagcaagggggaggacaatagcagggg
ggtgggcgaagaactccagcatgagatccccgcgctggaggatcatccagccggcgtcccgaaaacgattccgaag
cccaacctttcatagaaggcggcggtggaatcgaaatctcgtgatggcaggttgggcgtcgcttggtcggtcatttc
gaaccccagagtcccgctcagaagaactcgtcaagaaggcgatagaaggcgatgcgctgcgaatcgggagcggcgat
accgtaaagcacgaggaagcggtcagccgcattgccgccaagctcttcagcaatatcacgggtagccaacatgatgc
cctgatagcggtccgccacacccagccggccacagtcgatgaatccaccatgccactctgctatctcaccatgatattc
ggcaagcaggcatcgccatgggtcacgacgagatcctcgccgtcgggcatgcgcgccttgagcctggcgaacagttc
ggctggcgcgagcccctgatgctcttcgtccagatcatcctgatcgacaagaccggcttccatccgagtacgtgctc
gctcgatgcgatgtttcgcttggtggtcgaatgggcaggtagccggatcaagcgtatgcagccgccgcattgcatca
gccatgatggatactttctcggcaggagcaaggtgagatgacaggagatcctgccccggcacttcgcccaatagcag
ccagtcccttcccgcttcagtgacaacgtcgagcacagctgcgcaaggaacgcccgtcgtggccagccacgatagcc
gcgctgcctcgtcctgcagttcattcagggcaccggacaggtcggtcttgacaaaaagaaccgggcgcccctgcgct
gacagccggaacacggcggcatcagagcagccgattgtctgttgtgcccagtcatagccgaatagcctctccaccca
agcggccggagaacctgcgtgcaatccatcttgttcaatcatgcgaaacgatcctcatcctgtctcttgatcagatc
ttgatccctgcgccatcagatccttggcggcaagaaagccatccagtttactttgcagggcttcccaaccttacca
gagggcgccccagctggcaattccggttcgcttgctgtccataaaaccgcccagtctagctatcgccatgtaagccc
actgcaagctacctgctttctctttgcgcttgcgttttcccttgtccagatagcccagtagctgacattcatccggg
gtcagcaccgtttctgcggactggctttacgtgttccgctccttcagggcgccctgagtgcttgcggcagcgtggag
cagcgtgaagctaattcatggttaaattttgttaaatcagctcattttttaaccaataggccgaaatcggcaaaat
cccttataaatcaaagaatagcccgagataggtggtttggtagtttgccagttttgaacaagagtccactattaaga
acgtggactccaacgtcaaagggcgaaaaaccgtctatcagggcgatggcccgatcagcttatgcggtgtgaaatac
cgcacagatgcgtaaggagaaaataccgcatcaggcgctcttccgcttcctcgctcactgactcgctgcgctcggtc
gttcggctgcggcgagcggtatcagctcactcaaaggcggtaatacggttatccacagaatcaggggataacgcagg
aaagaacatgtgagcaaaaggccagcaaaaggccaggaaccgtaaaaaggccgcgttgctggcgtttttccatagga
ccgccccctgacgagcatcacaaaaatcgacgctcaagtcagaggtggcgaaacccgacaggactataaagatac
caggcgtttccccctggaagctccctcgtgcgctctcctgttccgaccctgccgcttaccggatacctgtccgcctt
tctcccttcgggaagcgtggcgctttctcatagctcacgctgtaggtatctcagttcggtgtaggtcgttcgctcca
agctgggctgtgtgcacgaaccccccgttcagcccgaccgctgcgccttatccggtaactatcgtcttgagtccaac
ccggtaagacacgacttatcgccactggcagcagccactggtaacaggattagcagagcgaggtatgtaggcggtgc
tacagagttcttgaagtggtggcctaactacggctacactagaaggacagtatttggtatctgcgctctgctgaagc
cagttaccttcggaaaaagagttggtagctcttgatccggcaaacaaaccaccgctggtagcggtggtttttttgtt
tgcaagcagcagattacgcgcagaaaaaaaggatctcaagaagatcctttgatcttttctactgaacggtgatcccc
accggaattgcg
```

(gH mature protein consisting of amino acid residues 24-715 of SEQ ID NO: 1)
SEQ ID NO: 29
RYGAEAVSEPLDKAFHLLLNTYGRPIRFLRENTTQCTYNSSLRNSTVVRENAISFNFFQSYNQYYVFHMPRCLFAGP
LAEQFLNQVDLTETLERYQQRLNTYALVSKDLASYRSFSQQLKAQDSLGEQPTTVPPPIDLSIPHVWMPPQTTPHGW
TESHTTSGLHRPHFNQTCILFDGHDLLFSTVTPCLHQGFYLIDELRYVKITLTEDFFVVTVSIDDDTPMLLIFGHLP
RVLFKAPYQRDNFILRQTEKHELLVLVKKDQLNRHSYLKDPDFLDAALDFNYLDLSALLRNSFHRYAVDVLKSGRCQ
MLDRRTVEMAFAYALALFAAARQEEAGAQVSVPRALDRQAALLQIQEFMITCLSQTPPRTTLLLYPTAVDLAKRALW
TPNQITDITSLVRLVYILSKQNQQHLIPQWALRQIADFALKLHKTHLASFLSAFARQELYLMGSLVHSMLVHTTERR
EIFIVETGLCSLAELSHFTQLLAHPHHEYLSDLYTPCSSSGRRDHSLERLTRLFPDATVPATVPAALSILSTMQPST
LETFPDLFCLPLGESFSALTVSEHVSYIVTNQYLIKGISYPVSTTVVGQSLIITQTDSQTKCELTRNMHTTHSITVA
LNISLENCAFCQSALLEYDDTQGVINIMYMHDSDDVLFALDPYNEVVSSPRTHYLMLLKNGTVLEVTDVVVDATD (gH mature protein comprising SEQ ID NOs: 29 and 5)
SEQ ID NO: 30
RYGAEAVSEPLDKAFHLLLNTYGRPIRFLRENTTQCTYNSSLRNSTVVRENAISFNFFQSYNQYYVFHMPRCLFAGP
LAEQFLNQVDLTETLERYQQRLNTYALVSKDLASYRSFSQQLKAQDSLGEQPTTVPPPIDLSIPHVWMPPQTTPHGW

SEQUENCE LISTING

```
TESHTTSGLHRPHFNQTCILFDGHDLLFSTVTPCLHQGFYLIDELRYVKITLTEDFFVVTVSIDDDTPMLLIFGHLP
RVLFKAPYQRDNFILRQTEKHELLVLVKKDQLNRHSYLKDPDFLDAALDFNYLDLSALLRNSFHRYAVDVLKSGRCQ
MLDRRTVEMAFAYALALFAAARQEEAGAQVSVPRALDRQAALLQIQEFMITCLSQTPPRTTLLLYPTAVDLAKRALW
TPNQITDITSLVRLVYILSKQNQQHLIPQWALRQIADFALKLHKTHLASFLSAFARQELYLMGSLVHSMLVHTTERR
EIFIVETGLCSLAELSHFTQLLAHPHHEYLSDLYTPCSSSGRRDHSLERLTRLFPDATVPATVPAALSILSTMQPST
LETFPDLFCLPLGESFSALTVSEHVSYIVTNQYLIKGISYPVSTTVVGQSLIITQTDSQTKCELTRNMHTTHSITVA
LNISLENCAFCQSALLEYDDTQGVINIMYMHDSDDVLFALDPYNEVVVSSPRTHYLMLLKNGTVLEVTDVVVDATDG
TKLGPEQKLISEEDLNSAVDHHHHHH (gL mature protein consisting of amino acid residues 31-278 of SEQ ID NO: 7)
                                                        SEQ ID NO: 31
AAVSVAPTAAEKVPAECPELTRRCLLGEVFEGDKYESWLRPLVNVTGRDGPLSQLIRYRPVTPEAANSVLLDEAFLD
TLALLYNNPDQLRALLTLLSSDTAPRWMTVMRGYSECGDGSPAVYTCVDDLCRGYDLTRLSYGRSIFTEHVLGFELV
PPSLFNVVVAIRNEATRTNRAVRLPVSTAAAPEGITLFYGLYNAVKEFCLRHQLDPPLLRHLDKYYAGLPPELKQTR
VNLPAHSRYGPQAVDAR (go mature protein consisting of amino acid residues 31-472 of SEQ ID NO: 10)
                                                        SEQ ID NO: 32
CNVLVNSRGTRRSWPYTVLSYRGKEILKKQKEDILKRLMSTSSDGYRFLMYPSQQKFHAIVISMDKFPQDYILAGPI
RNDSITHMWFDFYSTQLRKPAKYVYSEYNHTAHKITLRPPPCGTVPSMNCLSEMLNVSKRNDTGEKGCGNFTTFNPM
FFNVPRWNTKLYIGSNKVNVDSQTIYFLGLTALLLRYAQRNCTRSFYLVNAMSRNLFRVPKYINGTKLKNTMRKLKR
KQALVKEQPQKKNKKSQSTTTPYLSYTTSTAFNVTTNVTYSATAAVTRVATSTTGYRPDSNFMKSIMATQLRDLATW
VYTTLRYRNEPFCKPDRNRTAVSEFMKNTHVLIRNETPYTIYGTLDMSSLYYNETMSVENETASDNNETTPTSPSTR
FQRTFIDPLWDYLDSLLFLDKIRNFSLQLPAYGNLTPPEHRRAANLSTLNSLWWWSQ (pUL128 mature protein consisting of amino acid residues 28-171 of
SEQ ID NO: 14 and 15)
                                                        SEQ ID NO: 33
EECCEFINVNHPPERCYDFKMCNRFTVALRCPDGEVCYSPEKTAEIRGIVTTMTHSLTRQVVHNKLTSCNYNPLYLE
ADGRIRCGKVNDKAQYLLGAAGSVPYRWINLEYDKITRIVGLDQYLESVKKHKRLDVCRAKMGYMLQ (pUL130 mature protein consisting of amino acid residues 26-214 of
SEQ ID NO: 16)
                                                        SEQ ID NO: 34
SPWSTLTANQNPSPPWSKLTYSKPHDAATFYCPFLYPSPPRSPLQFSGFQRVSTGPECRNETLYLLYNREGQTLVER
SSTWVKKVIWYLSGRNQTILQRMPRTASKPSDGNVQISVEDAKIFGAHMVPKQTKLLRFVVNDGTRYQMCVMKLESW
AHVFRDYSVSFQVRLTFTEANNQTYTFCTHPNLIV (pUL131A mature protein consisting of amino acid residues 19-129 of
SEQ ID NO: 18 and SEQ ID NO: 19)
                                                        SEQ ID NO: 35
QCQRETAEKNDYYRVPHYWDACSRALPDQTRYKYVEQLVDLTLNYHYDASHGLDNFDVLKRINVTEVSLLISDFRRQ
NRRGGTNKRTTFNAAGSLAPHARSLEFSVRLFAN (gB mature protein consisting of amino acid residues 23-907 of SEQ ID NO: 21)
                                                        SEQ ID NO: 36
VSSSSTRGTSATHSHHSSHTTSAAHSRSGSVSQRVTSSQTVSHGVNETIYNTTLKYGDVVGVNTTKYPYRVCSMAQG
TDLIRFERNIVCTSMKPINEDLDEGIMVVYKRNIVAHTFKVRVYQKVLTFRRSYAYIHTTYLLGSNTEYVAPPMWEI
HHINSHSQCYSSYSRVIAGTVFVAYHRDSYENKTMQLMPDDYSNTHSTRYVTVKDQWHSRGSTWLYRETCNLNCMVT
ITTARSKYPYHFFATSTGDVVDISPFYNGTNRNASYFGENADKFFIFPNYTIVSDFGRPNSALETHRLVAFLERADS
VISWDIQDEKNVTCQLTFWEASERTIRSEAEDSYHFSSAKMTATFLSKKQEVNMSDSALDCVRDEAINKLQQIFNTS
YNQTYEKYGNVSVFETTGGLVVFWQGIKQKSLVELERLANRSSLNLTHNRTKRSTDGNNATHLSNMESVHNLVYAQL
QFTYDTLRGYINRALAQIAEAWCVDQRRTLEVFKELSKINPSAILSAIYNKPIAARFMGDVLGLASCVTINQTSVKV
LRDMNVKESPGRCYSRPVVIFNFANSSYVQYGQLGEDNEILLGNHRTEECQLPSLKIFIAGNSAYEYVDYLFKRMID
LSSISTVDSMIALDIDPLENTDFRVLELYSQKELRSSNVFDLEEIMREFNSYKQRVKYVEDKVVDPLPPYLKGLDDL
MSGLGAAGKAVGVAIGAVGGAVASVVEGVATFLKNPFGAFTIILVAIAVVIITYLIYTRQRRLCTQPLQNLFPYLVS
ADGTTVTSGSTKDTSLQAPPSYEESVYNSGRKGPGPPSSDASTAAPPYTNEQAYQMLLALARLDAEQRAQQNGTDSL
DGRTGTQDKGQKPNLLDRLRHRKNGYRHLKDSDEEENV
```

The invention claimed is:

1. A composition comprising a purified human Cytomegalovirus (HCMV) pentameric complex comprising: a pentamer-forming fragment of HCMV gH having a truncated transmembrane (TM) domain and a truncated ectodomain as compared to wild-type HCMV gH; HCMV gL or pentamer-forming fragment thereof; HCMV pUL128 or pentamer-forming fragment thereof; HCMV pUL130 or pentamer-forming fragment thereof; and HCMV pUL131A or pentamer-forming fragment thereof, wherein the truncated TM domain consists of an amino acid sequence having a deletion of the amino acids corresponding to residues 718 to 736 of wild-type sequence SEQ ID NO: 1, and wherein the truncated ectodomain consists of an amino acid sequence having a deletion of the amino acids corresponding to residues 716 and 717 of wild-type sequence SEQ ID NO: 1.

2. The composition of claim 1, wherein said gL, or pentamer-forming fragment thereof, comprises a sequence that is at least 80% identical to any one of SEQ ID NOs: 7-9 and 31.

3. The composition of claim 1, wherein said gL, or pentamer-forming fragment thereof, comprises a sequence selected from the group consisting of SEQ ID NOs: 7-9 and 31.

4. The composition of claim 1, wherein said pUL128, or pentamer-forming fragment thereof, comprises a sequence that is at least 80% identical to any one of SEQ ID NOs: 13-15 and 33.

5. The composition of claim 1, wherein said pUL128, or pentamer-forming fragment thereof, comprises a sequence selected from the group consisting of SEQ ID NOs: 13-15 and 33.

6. The composition of claim 1, wherein said pUL130, or pentamer-forming fragment thereof, comprises a sequence that is at least 80% identical to any one of SEQ ID NOs: 16, 17, and 34.

7. The composition of claim 1, wherein said pUL130, or pentamer-forming fragment thereof, comprises a sequence selected from the group consisting of SEQ ID NOs: 16, 17, and 34.

8. The composition of claim 1, wherein said pUL131A, or pentamer-forming fragment thereof, comprises a sequence that is at least 80% identical to any one of SEQ ID NOs: 18-20, and 35.

9. The composition of claim 1, wherein said pUL131A, or pentamer-forming fragment thereof, comprises a sequence selected from the group consisting of SEQ ID NOs: 18-20, and 35.

10. The composition of claim 1, that is a pharmaceutical comprising the purified HCMV pentameric complex and an adjuvant.

11. The pharmaceutical of claim 10, wherein the adjuvant comprises an aluminum salt, an oil-in-water emulsion, or a combination thereof.

12. The pharmaceutical of claim 11, wherein the adjuvant comprising an aluminum salt comprises aluminum hydroxide, aluminum oxyhydroxide, aluminum hydroxide adsorbed to a TLR7 agonist, or a combination thereof.

13. The pharmaceutical of claim 11, wherein the oil-in-water emulsion comprises MF59, AS03, or a combination thereof.

14. The composition of claim 1, wherein said pentamer-forming fragment of HCMV gH comprises a sequence that is at least 80% identical to any one of SEQ ID NOs: 4, 6, 29, and 30.

15. The composition of claim 14, wherein said pentamer-forming fragment of HCMV gH comprises a sequence selected from the group consisting of SEQ ID NOs: 4, 6, 29, and 30.

16. The composition of claim 15, wherein said pentamer-forming fragment of HCMV gH comprises the sequence SEQ ID NO: 6.

17. A purified human Cytomegalovirus (HCMV) pentameric complex comprising: a pentamer-forming fragment of HCMV gH having a truncated transmembrane (TM) domain and a truncated ectodomain as compared to wild-type HCMV gH; HCMV gL or pentamer-forming fragment thereof; HCMV pUL128 or pentamer-forming fragment thereof; HCMV pUL130 or pentamer-forming fragment thereof; and HCMV pUL131A or pentamer-forming fragment thereof, wherein the truncated TM domain consists of an amino acid sequence having a deletion of the amino acids corresponding to residues 718 to 736 of wild-type sequence SEQ ID NO: 1, and wherein the truncated ectodomain consists of an amino acid sequence having a deletion of the amino acids corresponding to residues 716 and 717 of wild-type sequence SEQ ID NO: 1.

18. The purified HCMV pentameric complex of claim 17, wherein said gL, or pentamer-forming fragment thereof, comprises a sequence that is at least 80% identical to any one of SEQ ID NOs: 7-9 and 31.

19. The purified HCMV pentameric complex of claim 17, wherein said pUL128, or pentamer-forming fragment thereof, comprises a sequence that is at least 80% identical to any one of SEQ ID NOs: 13-15 and 33.

20. The purified HCMV pentameric complex of claim 17, wherein said pUL130, or pentamer-forming fragment thereof, comprises a sequence that is at least 80% identical to any one of SEQ ID NOs: 16, 17, and 34.

21. The purified HCMV pentameric complex of claim 17, wherein said pUL131A, or pentamer-forming fragment thereof, comprises a sequence that is at least 80% identical to any one of SEQ ID NOs: 18-20, and 35.

22. The purified HCMV pentameric complex of claim 17, wherein said pentamer-forming fragment of HCMV gH comprises a sequence that is at least 80% identical to any one of SEQ ID NOs: 4, 6, 29, and 30.

23. The purified HCMV pentameric complex of claim 22, wherein said pentamer-forming fragment of HCMV gH comprises a sequence selected from the group consisting of SEQ ID NOs: 4, 6, 29, and 30.

24. The purified HCMV pentameric complex of claim 23, wherein said pentamer-forming fragment of HCMV gH comprises the sequence SEQ ID NO: 6.

25. The composition of claim 1, wherein said gL, or pentamer-forming fragment thereof, comprises a sequence that is at least 85% identical to any one of SEQ ID NOs: 7-9 and 31.

26. The composition of claim 1, wherein said gL, or pentamer-forming fragment thereof, comprises a sequence that is at least 90% identical to any one of SEQ ID NOs: 7-9 and 31.

27. The composition of claim 1, wherein said gL, or pentamer-forming fragment thereof, comprises a sequence that is at least 95% identical to any one of SEQ ID NOs: 7-9 and 31.

28. The composition of claim 1, wherein said pUL128, or pentamer-forming fragment thereof, comprises a sequence that is at least 85% identical to any one of SEQ ID NOs: 13-15 and 33.

29. The composition of claim 1, wherein said pUL128, or pentamer-forming fragment thereof, comprises a sequence that is at least 90% identical to any one of SEQ ID NOs: 13-15 and 33.

30. The composition of claim 1, wherein said pUL128, or pentamer-forming fragment thereof, comprises a sequence that is at least 95% identical to any one of SEQ ID NOs: 13-15 and 33.

31. The composition of claim 1, wherein said pUL130, or pentamer-forming fragment thereof, comprises a sequence that is at least 85% identical to any one of SEQ ID NOs: 16, 17, and 34.

32. The composition of claim 1, wherein said pUL130, or pentamer-forming fragment thereof, comprises a sequence that is at least 90% identical to any one of SEQ ID NOs: 16, 17, and 34.

33. The composition of claim 1, wherein said pUL130, or pentamer-forming fragment thereof, comprises a sequence that is at least 95% identical to any one of SEQ ID NOs: 16, 17, and 34.

34. The composition of claim 1, wherein said pUL131A, or pentamer-forming fragment thereof, comprises a sequence that is at least 85% identical to any one of SEQ ID NOs: 18-20, and 35.

35. The composition of claim 1, wherein said pUL131A, or pentamer-forming fragment thereof, comprises a sequence that is at least 90% identical to any one of SEQ ID NOs: 18-20, and 35.

36. The composition of claim 1, wherein said pUL131A, or pentamer-forming fragment thereof, comprises a sequence that is at least 95% identical to any one of SEQ ID NOs: 18-20, and 35.

37. The composition of claim 1, wherein said pentamer-forming fragment of HCMV gH comprises a sequence that is at least 85% identical to any one of SEQ ID NOs: 4, 6, 29, and 30.

38. The composition of claim 1, wherein said pentamer-forming fragment of HCMV gH comprises a sequence that is at least 90% identical to any one of SEQ ID NOs: 4, 6, 29, and 30.

39. The composition of claim 1, wherein said pentamer-forming fragment of HCMV gH comprises a sequence that is at least 95% identical to any one of SEQ ID NOs: 4, 6, 29, and 30.

40. The purified HCMV pentameric complex of claim 17, wherein said gL, or pentamer-forming fragment thereof, comprises a sequence that is at least 85% identical to any one of SEQ ID NOs: 7-9 and 31.

41. The purified HCMV pentameric complex of claim 17, wherein said gL, or pentamer-forming fragment thereof, comprises a sequence that is at least 90% identical to any one of SEQ ID NOs: 7-9 and 31.

42. The purified HCMV pentameric complex of claim 17, wherein said gL, or pentamer-forming fragment thereof, comprises a sequence that is at least 95% identical to any one of SEQ ID NOs: 7-9 and 31.

43. The purified HCMV pentameric complex of claim 17, wherein said pUL128, or pentamer-forming fragment thereof, comprises a sequence that is at least 85% identical to any one of SEQ ID NOs: 13-15 and 33.

44. The purified HCMV pentameric complex of claim 17, wherein said pUL128, or pentamer-forming fragment thereof, comprises a sequence that is at least 90% identical to any one of SEQ ID NOs: 13-15 and 33.

45. The purified HCMV pentameric complex of claim 17, wherein said pUL128, or pentamer-forming fragment thereof, comprises a sequence that is at least 95% identical to any one of SEQ ID NOs: 13-15 and 33.

46. The purified HCMV pentameric complex of claim 17, wherein said pUL130, or pentamer-forming fragment thereof, comprises a sequence that is at least 85% identical to any one of SEQ ID NOs: 16, 17, and 34.

47. The purified HCMV pentameric complex of claim 17, wherein said pUL130, or pentamer-forming fragment thereof, comprises a sequence that is at least 90% identical to any one of SEQ ID NOs: 16, 17, and 34.

48. The purified HCMV pentameric complex of claim 17, wherein said pUL130, or pentamer-forming fragment thereof, comprises a sequence that is at least 95% identical to any one of SEQ ID NOs: 16, 17, and 34.

49. The purified HCMV pentameric complex of claim 17, wherein said pUL131A, or pentamer-forming fragment thereof, comprises a sequence that is at least 85% identical to any one of SEQ ID NOs: 18-20, and 35.

50. The purified HCMV pentameric complex of claim 17, wherein said pUL131A, or pentamer-forming fragment thereof, comprises a sequence that is at least 90% identical to any one of SEQ ID NOs: 18-20, and 35.

51. The purified HCMV pentameric complex of claim 17, wherein said pUL131A, or pentamer-forming fragment thereof, comprises a sequence that is at least 95% identical to any one of SEQ ID NOs: 18-20, and 35.

52. The purified HCMV pentameric complex of claim 17, wherein said pentamer-forming fragment of HCMV gH comprises a sequence that is at least 85% identical to any one of SEQ ID NOs: 4, 6, 29, and 30.

53. The purified HCMV pentameric complex of claim 17, wherein said pentamer-forming fragment of HCMV gH comprises a sequence that is at least 90% identical to any one of SEQ ID NOs: 4, 6, 29, and 30.

54. The purified HCMV pentameric complex of claim 17, wherein said pentamer-forming fragment of HCMV gH comprises a sequence that is at least 95% identical to any one of SEQ ID NOs: 4, 6, 29, and 30.

* * * * *